US011969462B2

(12) United States Patent
Bendjama et al.

(10) Patent No.: US 11,969,462 B2
(45) Date of Patent: Apr. 30, 2024

(54) PERSONALIZED VACCINE

(71) Applicant: Transgene, Illkirch-Graffenstaden (FR)

(72) Inventors: Kaïdre Bendjama, Illkirch-Graffenstaden (FR); Nathalie Silvestre, Ergersheim (FR); Jean-Baptiste Marchand, Obernai (FR); Benoît Grellier, Strasbourg (FR)

(73) Assignee: Transgene, Illkirch-Graffenstaden (FR)

( * ) Notice: Subject to any disclaimer, the term of this patent is extended or adjusted under 35 U.S.C. 154(b) by 563 days.

(21) Appl. No.: 16/625,239

(22) PCT Filed: Jun. 21, 2018

(86) PCT No.: PCT/EP2018/066668
§ 371 (c)(1),
(2) Date: Dec. 20, 2019

(87) PCT Pub. No.: WO2018/234506
PCT Pub. Date: Dec. 27, 2018

(65) Prior Publication Data
US 2020/0138923 A1 May 7, 2020

(30) Foreign Application Priority Data

Jun. 21, 2017 (EP) .................................... 17305760
Apr. 23, 2018 (EP) .................................... 18305496

(51) Int. Cl.
*A61K 39/00* (2006.01)
*C12N 7/00* (2006.01)
*C12N 15/63* (2006.01)
*C12Q 1/6886* (2018.01)

(52) U.S. Cl.
CPC ............ *A61K 39/0011* (2013.01); *C12N 7/00* (2013.01); *C12N 15/63* (2013.01); *C12Q 1/6886* (2013.01); *A61K 2039/5256* (2013.01); *A61K 2039/585* (2013.01); *C12N 2710/24134* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | |
|---|---|---|
| 5,250,534 A | 10/1993 | Bell et al. |
| 5,972,597 A | 10/1999 | Paoletti et al. |
| 6,440,422 B1 | 8/2002 | Sutter et al. |
| 6,469,012 B1 | 10/2002 | Ellis et al. |
| 6,998,252 B1 | 2/2006 | Moss et al. |
| 7,108,844 B2 | 9/2006 | Carpentier |
| 7,700,569 B1 | 4/2010 | Carpentier |
| 2011/0293637 A1* | 12/2011 | Hacohen .......... G01N 33/57492 424/277.1 |
| 2014/0296081 A1* | 10/2014 | Diehn .................. C12Q 1/6806 506/8 |
| 2015/0140041 A1* | 5/2015 | Vitiello .............. A61K 39/0011 424/277.1 |
| 2017/0199961 A1* | 7/2017 | Yelensky ................ G16H 20/10 |
| 2019/0030147 A1* | 1/2019 | Artomov ................ A61K 39/39 |
| 2019/0060428 A1* | 2/2019 | Fritsch ............... A61K 39/0011 |

FOREIGN PATENT DOCUMENTS

| | | | |
|---|---|---|---|
| EP | 0 463 756 B1 | 4/1995 | |
| EP | 1 162 982 B1 | 2/2005 | |
| EP | 2 199 400 A1 | 6/2010 | |
| EP | 2199400 A1 * | 6/2010 | ............. C12N 15/86 |
| WO | WO 97/02355 A1 | 1/1997 | |
| WO | WO 99/03885 A1 | 1/1999 | |
| WO | WO 2003/008533 A3 | 1/2003 | |
| WO | WO 2007/147528 A1 | 12/2007 | |
| WO | WO-2007147528 A1 * | 12/2007 | ............. A61K 35/76 |
| WO | WO 2008/092854 A3 | 8/2008 | |
| WO | WO 2008/138533 A1 | 11/2008 | |

(Continued)

OTHER PUBLICATIONS

Chen et al (Fusion protein linkers: Property, design and functionality, Advanced Drug Delivery Reviews, vol. 65, Oct. 2013), (Year: 2013).*
Yuan et al (Efficiently Editing the Vaccinia Virus Genome by Using the CRISPR-Cas9 System, Journal of Virology, vol. 89, Apr. 3, 2015). (Year: 2015).*
Chowell et al (PNAS, 2015, E1754-E1762), teach (Year: 2015).*
Acres et al., *Clinical development of MVA-based therapeutic cancer vaccines*, Expert Reviews 7(7) Vaccines 889-893 (2008).
Anderson et al., *Next Generation DNA Sequencing and the Future of Genomic Medicine*, 1(1) Genes 38-69 (2010).

(Continued)

*Primary Examiner* — Sean E Aeder
*Assistant Examiner* — Sarah A Alsomairy
(74) *Attorney, Agent, or Firm* — Panitch Schwarze Belisario & Nadel LLP

(57) ABSTRACT

The present invention generally relates to a personalized cancer vaccine comprising a recombinant poxvirus encoding one or more neopeptide(s) or a composition comprising such a recombinant poxvirus and a pharmaceutically acceptable vehicle as well as the use of the personalized cancer vaccine for treating a cancerous subject in need thereof. A specific embodiment is directed to a method of providing such a vaccine or composition comprising an identification step comprising a) extracting the DNA from a tumor sample and a non-tumor sample, b) selecting target regions, c) sequencing the target regions from the extracted DNAs and d) identifying one or more tumor-specific mutation(s) by comparing the DNA sequences obtained from the tumor and non-tumor samples. Embodiments also include a method of treating cancer or preventing its relapse comprising administration of such a personalized cancer vaccine. The invention is of very special interest in the field of personalized immunotherapy.

18 Claims, 9 Drawing Sheets
Specification includes a Sequence Listing.

(56) References Cited

FOREIGN PATENT DOCUMENTS

| | | | |
|---|---|---|---|
| WO | WO 2008/138649 A3 | 11/2008 | |
| WO | WO 2009/065546 A1 | 5/2009 | |
| WO | WO 2009/065547 A3 | 5/2009 | |
| WO | WO 2009/100521 A1 | 8/2009 | |
| WO | WO 2010/130753 A1 | 11/2010 | |
| WO | WO 2012/159754 A3 | 11/2012 | |
| WO | WO 2013/022764 A1 | 2/2013 | |
| WO | WO-2014168874 A2 * | 10/2014 | ......... A61K 39/0011 |
| WO | WO 2015/085233 A1 | 6/2015 | |
| WO | WO-2015085233 A1 * | 6/2015 | ........... A61K 31/194 |
| WO | WO 2015/175334 A3 | 11/2015 | |
| WO | WO 2015/175340 A1 | 11/2015 | |
| WO | WO 2016/187508 A3 | 11/2016 | |
| WO | WO 2016/191545 A1 | 12/2016 | |
| WO | WO 2016/207859 A1 | 12/2016 | |
| WO | WO 2014/168874 A2 | 9/2018 | |

OTHER PUBLICATIONS

Andreatta et al., *accurate pan-specific prediction of peptide-MHC class II binding affinity with improved binding core identification*, 67(0) Immunogenetics 641-650 (Nov. 2015).

Antoine et al., *The Complete Genomic Sequence of the Modified Vaccinia Ankara Strain: Comparison with Other Orthopoxviruses*, 244(2) Virology 365-396 (1998).

Bainbridge et al., *Whole exome capture in solution with 3 Gbp of data*, 11(R62) Genome Biology 1-8 (2010).

Biswas et al., *Evaluation of methods for measuring amino acid hydrophobicities and interactions*, 1000(1-2) Journal of Chromatography 637-655 (2003).

Boegel et al., *In Silico HLA Typing Using Standard RNA-Seq Sequence Reads*, 1310 Methods in Molecular Biology 247-258 (2015).

Carpentier et al., *CpG-Oligonucleotides for Cancer Immunotherapy: Review of the Literature and Potential Applications in Malignant Glioma*, 8 Frontiers in Bioscience 115-127 (Jan. 1, 2003).

Carpentier et al., *Phase 1 trial of a CpG oligodeoxynucleotide for patients with recurrent glioblastoma*, 8(1) Neuro-Oncology 60-66 (Jan. 2006).

Carroll et al., *Host Range and Cytopathogenicity of the Highly Attenuated MVA Strain of Vaccinia Virus: Propagation and Generation of Recombinant Viruses in a Nonhuman Mammalian Cell Line*, 238(2) Virology 198-211 (1997).

Chakrabarti et al., *Compact, Synthetic, Vaccinia Virus Early/Late Promoter for Protein Expression*, 23(6) BioTechniques 1094-1097 (Dec. 1997).

Chu et al., *RNA Sequencing: Platform Selection, Experimental Design, and Data Interpretation*, 22(4) Nucleic Acid Therapeutics 271-274 (2012).

Claudepierre et al., *Yeast Virus-Derived Stimulator of the Innate Immune System Augments the Efficacy of Virus Vector-Based Immunotherapy*, 88(10) Journal of Virology 5242-5255 (May 2014).

Cock et al., *The Sanger FASTQ file format for sequences with quality scores, and the Solexa/Illumina FASTQ Variants*, 38(6) Nucleic Acids Research 1767-1771 (2010).

D'Alise et al., *NKTR-214 2017SITC Poster-P434—Nektar Therapeutics: Great Apes Adenoviral vaccine encoding neoantigens synergizes with immunomodulator (NKTR-214) to cure established tumors in mice* (Nov. 11, 2017) (1 page).

Danecek et al., *The variant call format and VCFtools*, 27(15) Bioinformatics 2156-2158 (2011).

Edgar et al., *Error filtering, pair assembly and error correction for next-generation sequencing reads*, 31(21) Bioinformatics 3476-3482 (2015).

Erbs et al., *Modified vaccinia virus Ankara as a vector for suicide gene therapy*, 15(1) Cancer Gene Therapy 18-28 (2008).

Farsaci et al., *Chapter 5/Design, development, and translation of poxvirus-based vaccines for cancer, Cancer Vaccines: From Research to Clinical Practice* 56-77 (2011).

Fend et al., *Intravenous Injection of MVA Virus Targets CD8+ Lymphocytes to Tumors to Control Tumor Growth upon Combinatorial Treatment with a TLR9 Agonist*, 2(12) Cancer Immunology Research 1-12 (Dec. 2014).

Gulley et al., *A Pilot Study to Evaluate the Safety and Clinical Outcomes of Vaccination with Recombinant CEA-MUC-1-TRICOM (PANVAC) Poxviral-based Vaccines in Patients with Metastatic Carcinoma*, 14(10) Clin Cancer Res. 3060-3069 (May 15, 2008).

Guse et al., *Oncolytic vaccinia virus for the treatment of cancer*, 11(5) Expert Opinion On Biological Therapy 595-608 (2011).

Hammond et al., *A synthetic vaccinia virus promoter with enhanced early and late activity*, 66(1) Journal of Virological Methods 135-138 (1997).

Hundal et al., *pVAC-Seq: A genome-guided in silico approach to identifying tumor neoantigens*, 8(11) Genome Medicine 1-11 (2016).

Husseini et al., *Vectorized gene therapy of liver tumors: proof-of-concept of TG4023 (MVA-FCU1) in combination with flucytosine*, 28(1) Annals of Oncology 169-174 (2017).

Kreiter et al., *Mutant MHC class II epitopes drive therapeutic immune responses to cancer*, 520 Nature 692-696 (Apr. 30, 2015).

Krogh et al., *Predicting Transmembrane Protein Topology with a Hidden Markov Model: Application to Complete Genomes*, 305(3) Journal of Molecular Biology 567-580 (2001).

Kumar et al., *A Poxvirus Bidirectional Promoter Element with Early/Late and Late Functions*, 179(1) Virology 151-158 (1990).

Kyte et al., *A Simple Method for Displaying the Hydropathic Character of a Protein*, 157(1) Journal of Molecular Biology 105-132 (1982).

Li et al., *Automated inference of molecular mechanisms of disease from amino acid substitutions*, 25(21) Bioinformatics 2744-2750 (2009).

Meyer et al., *Mapping of deletions in the genome of the highly attenuated vaccinia virus MVA and their influence on virulence*, 72 Journal of General Virology 1031-1038 (1991).

Moodie et al., *Response definition criteria for ELISPOT assays revisited*, 59(1) Cancer Immunol Immunother 1489-1501 (2010).

Moodie et al., *Statistical positivity criteria for the analysis of ELISpot assay data in HIV-1 vaccine trials*, 315 (1-2) Journal of Immunological Methods 121-132 (2006).

Ng et al., *Targeted Capture and Massively Parallel Sequencing of Twelve Human Exomes*, 461 Nature 272-276 (Sep. 10, 2009).

Nielsen et al., *Genotype and SNP calling from next-generation sequencing data*, 12(6) Nature Reviews Genetics 443-451 (Jun. 2011).

Nielsen et al., *MHC Class II epitope predictive algorithms*, 130(3) Immunology 319-328 (2010).

Plotkin, *Correlates of Vaccine-Induced Immunity*, 47(3) Clinical Infectious Diseases 401-109 (Aug. 2008).

Quoix et al., *Therapeutic vaccination with TG4010 and first-line chemotherapy in advanced non-small-cell lung cancer: a controlled phase 2B trial*, 12(12) The Lancet Oncology 1125-1133 (Nov. 2011).

Relman, *Learning to Appreciate Our Differences*, 198 The Journal of Infectious Diseases 4-5 (Jul. 1, 2008).

Rock et al., *Proteases in MHC class I presentation and cross-presentation*, 184(1) The Journal of Immunology 9-15 (Jan. 1, 2010).

Rose et al., *Hydrogen Bonding, Hydrophobicity, Packing, and Protein Folding*, 22 Annual Review of Biophysics and Biomolecular Structure 381-415 (1993).

Sutter et al., *Nonreplicating vaccinia vector efficiently expresses recombinant genes*, 89(22) PNAS USA 10847-10851 (1992).

Sweet et al., *Correlation of Sequence Hydrophobicities Measures Similarity in Three-Dimensional Protein Structure*, 171(4) Journal of Molecular Biology 479-488 (1983).

Wang et al., *RNA-Seq: a revolutionary tool for transcriptomics*, 10(1) Nature Reviews Genetics 57-63 (Jan. 2009).

Yuan et al., *Efficiently Editing the Vaccinia Virus Genome by Using the CRISPR-Cas9 System*, 89(9) Journal of Virology 5176-5179 (May 2015).

Yuan et al., *CRISPR-Cas9 as a Powerful Tool for Efficient Creation of Oncolytic Viruses*, 8(3) Viruses 1-10 (2016).

(56) References Cited

OTHER PUBLICATIONS

Delord et al., *Phase 1 studies of personalized neoantigen vaccine TG4050 in ovarian carcinoma (OvC) and head and neck squamous cell carcinoma (HSNCC)*, American Society of Clinical Oncology Annual Meeting poster (Jun. 2022).

Duraiswamy et al., *Therapeutic LMP1 polyepitope vaccine for EBV-associated Hodgkin disease and nasopharyngeal carcinoma*, 15 Blood 3150-3156 (Apr. 15, 2003).

Mateo et al., *An HLA-A2 Polyepitope Vaccine for Melanoma Immunotherapy*, 163 J. Immunology 4058-4063 (1999).

Transgene Press Release: *Transgene Presented Additional Phase I Data with TG4050 (myvac® platform) at ASCO 2022* (Jun. 6, 2022).

Transgene Press Release, Transgene and NEC Present New Data on TG4050, an Individualized Cancer Vaccine, Showing it Induces Specific Immune Responses against Head and Neck Carcinoma at ASCO 2023 (Jun. 6, 2023).

Ottensmeir et al., *Safety and Immunogenicity of TG4050: a personalized cancer vaccine in head and neck carcinoma* Transgene (2023).

\* cited by examiner

Figure 1

MVATG19022 p11k7.5 | GS | FCU1 | GS | β-Gal | GS | E1 HPV16 | GS | E7 HPV16 | GS | MUC1 | GS | Flag

MVATG19023 p11k7.5 | SR | GS | FCU1 | GS | β-Gal | GS | E1 HPV16 | GS | E7 HPV16 | GS | MUC1 | GS | Flag

Figure 3

Pentatope 1

MGSGSGSGSGSYRGANLHEETLAGPWARLLERLFKQLGSGSGSGSGSGYISRVTAGKDSYIALVDKNIMGYIAGSGSGSGSGSAGTQCEYWASRALDSEHSIGSMI
QLPQGSGSGSGSGSEGDPCLRSSDCIDEFCCARHPWTKICKGSGSGSGSGSVTSIPSVSNALNWKEFSFIQSTLGYVAGSGSGSGSGSDYKDDDDK

Pentatope 2

MGSGSGSGSGSPLLPFYPPDEALEIGLELNSSALPPTEGSGSGSGSGSVILPQAPSGPSYATYLQPAQAQMLTPPGSGSGSGSGSDKPLRRNNSYTSYIMAICGMPLDSF
RAGSGSGSGSGSEVIQTSKYYMRDVIAIESAWLLELAPHGSGSGSGSGSEHIHRAGGLFVADAIQVGFGRIGKHFWGSGSGSGSGSEQKLISEEDL

Figure 7

GSG (Gly-Ser-Gly)

```
GSG_1  :  GGAAGCGGT
GSG_2  :  GGATCTGGT
GSG_3  :  GGATCGGGA
GSG_4  :  GGTAGTGGC
GSG_5  :  GGTTCTGGG
GSG_6  :  GGTTCCGGT
GSG_7  :  GGTTCGGGT
GSG_8  :  GGCTCAGGA
GSG_9  :  GGCTCTGGA
GSG_10 :  GGCAGCGGA
GSG_11 :  GGCAGTGGT
GSG_12 :  GGGAGTGGG
GSG_13 :  GGGTCTGGC
GSG_14 :  GGGTCAGGG
GSG_15 :  GGGTCCGGA
```

GTS (Gly-Thr-Ser)

```
GTS_2  :  GGAACTTCG
GTS_3  :  GGAACGTCC
GTS_4  :  GGTACAAGT
GTS_5  :  GGTACGAGC
GTS_6  :  GGTACCTCT
GTS_7  :  GGTACTAGT
GTS_8  :  GGGACCAGT
GTS_10 :  GGGACTTCA
GTS_11 :  GGCACCAGC
GTS_12 :  GGCACGTCG
```

GAS (Gly-Ala-Ser)

```
GAS_1  :  GGTGCGAGC
GAS_3  :  GGAGCGTCC
GAS_4  :  GGAGCCTCG
GAS_6  :  GGTGCATCA
GAS_7  :  GGTGCTTCT
```

Figure 8

| MVA | Cassette | | | Linker | % white plaques | PCR | | |
|---|---|---|---|---|---|---|---|---|
| | | 1 | 2 | 3 | | | Recombinant mCherry neg | Recombinant mCherry pos | Parental |
| TG19258 | Nb neo | 10 | 10 | 7 | no | 4.9 | 0 | 0 | 13 |
| | TM | 0 | 0 | 0 | | | | | |
| | Hydro | -0.36 | -0.08 | 0.151 | | | | | |
| TG19267 | Nb neo | 10 | 10 | 7 | 3aa | 13.3 | 5 | 2 | 2 |
| | TM | 0 | 0 | 0 | | | | | |
| | Hydro | -0.39 | -0.09 | 0.08 | | | | | |
| TG19290 | Nb neo | 10 | 10 | 10 news | no | 3.8 | 3 | 3 | 0 |
| | TM | 0 | 0 | 0 | | | | | |
| | Hydro | -0.36 | -0.08 | -0.52 | | | | | |
| TG19291 | Nb neo | 10 | 10 | 10 news | 3aa | 4.7 | 3 | 4 | 0 |
| | TM | 0 | 0 | 0 | | | | | |
| | Hydro | -0.39 | -0.09 | -0.52 | | | | | |
| TG19293 | Nb neo | 10 | 10 | - | 3aa | 16 | 1 | 9 | 0 |
| | TM | 0 | 0 | - | | | | | |
| | Hydro | -0.39 | -0.09 | - | | | | | |
| TG19298 | Nb neo | - | 10 | 10 news | 3aa | 16.3 | 8 | 3 | 0 |
| | TM | - | 0 | 0 | | | | | |
| | Hydro | - | -0.09 | -0.52 | | | | | |

PERSONALIZED VACCINE

CROSS-REFERENCE TO RELATED APPLICATIONS

This application is a U.S. National Stage Application pursuant to 35 U.S.C. § 371 of International Patent Application PCT/2018/066668, filed on Jun. 21, 2018, and published as WO 2018/234506 on Dec. 27, 2018, which claims priority to European Patent Application 18305496.14, filed on Apr. 23, 2018, and European Patent Application 17305760.5, filed on Jun. 21, 2017, all of which are incorporated herein by reference in their entireties for all purposes.

TECHNICAL FIELD OF THE INVENTION

The present invention generally relates to a personalized cancer vaccine comprising a recombinant poxvirus encoding one or more neopeptide(s) or a composition comprising such a recombinant poxvirus and a pharmaceutically acceptable vehicle as well as the use of said personalized cancer vaccine for treating a cancerous subject in need thereof. A specific embodiment is directed to a method of providing such a vaccine or composition comprising an identification step comprising a) extracting the DNA from a tumor sample and a non-tumor sample, b) selecting target regions, preferably the entire coding regions of the genome (exome), c) sequencing said target regions (e.g. the exome) from said extracted DNAs and d) identifying one or more tumor-specific mutation(s) by comparing the DNA sequences obtained from said tumor and non-tumor samples. Embodiments also include a method of treating cancer or preventing its relapse comprising administration of such a personalized cancer vaccine. The invention is of very special interest in the field of personalized immunotherapy, specifically for stimulating T cell immune response.

BACKGROUND

During the last decades, numerous therapeutic vaccines expressing tumor antigens have been generated with the goal of stimulating innate and specific immune responses against tumor antigens. However, the most commonly identified tumor-associated antigens (eg. MUC-1, WT1, PSA, CEA) are selectively overexpressed in the tumor but can have residual expression in non-tumor cells. Thus, efficacy of this traditional approach is expected to be limited by self-tolerance against such "self" antigens.

Moreover, the traditional paradigm to deliver the same set of cancer antigens to everyone in the population ignores individual variability in disease risk and immunologic responses. Importantly, it could not be ignored that humans respond differently to vaccines and the host's immune response significantly varies in a population (Reiman, 2008, J Infect Dis. 198(1):4-5; Plotkin, 2008, Clin Infect Dis. 47(3):401-9). With the recent introduction of immune checkpoint blockers in the clinic, it has indeed become clear to the medical staff that some treatments are effective for some patients but not for others.

Advances in immunology, genetics, molecular biology and bioinformatics have paved the way to more personalized approaches. Technological breakthroughs in the field of genome sequencing (e.g. Next Generation Sequencing (NGS)) has now made it possible to sequence the entire genome or exome (coding regions of the genome) of tumor at an unprecedented speed and cost. Molecular characterization of tumors demonstrated that during the process of carcinogenesis and proliferation of cancer cells, mutations occur as a consequence of high rates of proliferations, deficient repair mechanisms and clonal selection. Accumulation of mutations in the tumor genome generally leads to expression of aberrant protein species that are specific to cancerous tissue. Those are referred to as neoantigens. In contrast to the most common tumor-associated antigens, tumor neoantigens are solely present in tumor cells but not in normal cells and do not induce deletion of their antigen-specific T cells in the thymus. Thus, it is expected that they induce strong immune responses without bearing the risk for self-tolerance and autoimmune reactions against self-proteins. Therefore, tumor neoantigens may be ideal targets for designing therapeutic vaccines specifically adapted to the tumor although their adoption in routine care requires overcoming a number of scientific and technical challenges. In particular, most cancer mutations are the result of stochastic phenomenon and are specific to each patient.

The selection of an appropriate vaccine platform is a major factor for its success in clinical setting. Several technological platforms are currently envisioned for the development of neoantigen directed vaccines, including bacteria (such as the Listeria-based ADXS-Neo vaccine developed by Advaxis; WO2016/207859; WO2016/191545), viral vector (such as the lentiviral system ZVex of Immune Design), nucleic acid vaccines (e.g. acid mRNA-based vaccine encapsuled in nanoparticles as developed by Biontech; Kreiter et al., 2015, Nature 520 692-6; WO2012/159754, a DNA encoding for a vaccinal complex developed by Vaccibody) and adjuvanted peptides (WO2016/187508). Representative examples of peptide vaccines include, e.g. polyICLC (Polyinosinic-polycytidyl Acid)-stabilized peptides currently developed by NEON Therapeutics in bladder cancers, glioblastomas and non-small cell lung cancers (NSCLC) in combination with Nivolumab; gp96 (96 kDa heat shock protein)-adjuvanted tumor neoantigens developed by Agenus; and liposome-encapsulated peptides of the University of Connecticut School of Medicine). Another recent alternative is the use of dendritic cells (DC) as a vector after in vitro exposure to the antigen before administration to the patient. DC are pulsed with peptides or with tumor lysates (e.g. activated DC vaccines Sipuleucel-T commercialized by Dendreon, DC loaded with patient tumor exomes developed by Exocyte Therapeutics; DC vaccine developed by OncoTherapeutics Science and Tella Inc).

Nevertheless, most initiatives in the field must meet major challenges before delivering its promises. Among other topics, successful translation is subordinated to the achievement of an effective manufacturing process to ensure prompt delivery of clinically sufficient amounts to the bedside of the patient because identification of the tumor mutations, design of the neopeptides incorporating such mutations, manufacturing and testing of the personalized vaccine is concomitant to disease progression.

Thus, there is a need to develop a streamlined and time-intensive process permitting the identification of neoantigens for each patient's tumor and the manufacture of the corresponding personalized therapy with the standards established for drug manufacture.

Recombinant MVA (for Modified Virus Ankara) has served as an effective vector in previous attempts to develop cancer vaccines (Acres and Bonnefoy, 2008, Expert Review of Vaccines 7, 889-93). Vaccinia based vaccines have achieved results when given as a monotherapy or in combination with chemotherapy, radiotherapy or immune checkpoint inhibitor (Farsaci et al., 2011, In Cancer Vaccines:

From Research to Clinical Practice, Ed Bat; CRC Press, pp 56-77; WO2015/175340; WO2015/175334). For instance, TG4010 (or MVATG9931 with its research name), a MVA-based cancer vaccine coding for MUC1 tumor-associated antigen and human interleukin 2 (IL-2), demonstrated efficacy in combination with first-line standard of care chemotherapy in advanced metastatic NSCLC (Quoix et al., 2011, The Lancet Oncology 12(12): 1125-33). Antigen-specific tumor control by MVATG9931 in the prophylactic RMA-MUC1 model clearly depends on transient de novo expression of MUC1 and $CD8^+$ and $CD4^+$ T cells. Other poxviruses, and in particular vaccinia viruses and fowlpox viruses, have also been used as anticancer vectors (Gulley et al., 2008, Clin Cancer Res 14(10): 3060-9).

However, the ability of MVA or other poxviruses to induce a strong immune response against cancer neoantigens has not been tested and remains to be established. In addition, known processes for producing recombinant MVAs rely on homologous recombination, which has a low efficiency, and are thus quite lengthy.

The inventors however found that a recombinant MVA is indeed able to induce immune responses against several cancer neoantigens, and that a personalized MVA encoding several neopeptides may be generated rapidly.

The disclosure meets the aforementioned need by providing for MVA-based cancer vaccines expressing fusion of anti-tumor neopeptides as well as a manufacturing process that has been specifically designed for maximizing generation of recombinant MVA and improving scalability and time to complete the process.

This technical problem is solved by the provision of the embodiments as defined in the claims.

Other and further aspects, features and advantages of the present invention will be apparent from the following description of the presently preferred embodiments of the invention. These embodiments are given for the purpose of disclosure.

BRIEF SUMMARY OF THE INVENTION

The present invention relates generally to a personalized cancer vaccine comprising a recombinant poxvirus encoding one or more neopeptide(s).

In one aspect, the recombinant poxvirus is a vaccinia virus, preferably a replication-defective vaccinia virus such as a MVA.

In another aspect, each of said one or more neopeptide(s) encoded by the recombinant poxvirus comprises at least one tumor-specific mutation with a preference for at least 60% of said neopeptides comprise a missense or a frameshift mutation. Desirably, the one or more neopeptide(s) has a length from 16 to 90 amino acid residues, preferably from 17 to 85 amino acid residues and more preferably from 18 to 80 amino acid residues. In preferred embodiments, the neopeptides comprising a missense mutation have a length from 18 to 29 residues and the neopeptides comprising a frameshift mutation have a length from to 80 amino acid residues. At least 80%, of neopeptides having a missense mutation carry the substituted amino acid in central position. In a preferred embodiment, several and preferably all neopeptides are expressed by the recombinant poxvirus in the form of one or more fusion(s). The recombinant poxvirus may further encode one or more therapeutic genes, preferably selected from the group consisting of suicide and immunostimulatory genes.

In a further aspect, the present invention also provides a process for preparing said personalized cancer comprising a step of identifying one or more neopeptide(s) suitable for being encoded by the personalized cancer vaccine wherein said one or more neopeptide(s) comprise(s) at least one tumor-specific mutation(s). A preferred process comprises an identification step comprising the following sub-steps a) to d): a) extracting the DNA from a tumor sample and a non-tumor sample, b) selecting target regions, preferably the entire coding regions of the genome (exome), c) sequencing said target regions (e.g. the exome) from said extracted DNAs and d) identifying one or more tumor-specific mutation(s) by comparing the DNA sequences obtained from said tumor and non-tumor samples. Such a process may further comprise at least one of the following additional sub-steps e) to g): e) ranking potential neopeptide(s) by their levels of expression in the tumor, either at the mRNA transcriptional level, or at the protein translation level; f) selecting non-self-expressed tumor-specific mutation(s); g) predicting the immune potential of the neoepitope(s) comprised in said neopeptide(s).

Further to the identification step, the process may also comprise a step of generating said recombinant poxvirus. Preferably, said neopeptide-encoding nucleic acid molecules (s) to be inserted in the genome of the recombinant poxvirus is/are arranged in one or more expression cassette(s) under the control of suitable regulatory elements permitting expression in the subject. Preferably, said step of generating the recombinant poxvirus uses a parental poxvirus comprising a fluorescent reporter gene cloned at the site of insertion that is selected for the neopeptide-encoding nucleic acid molecule(s) or expression cassette(s). In a preferred embodiment, said step of generating said recombinant poxvirus comprises a step of cleavage by an endonuclease able to generate at least one double strand break in said fluorescent reporter nucleotide sequence but in which said endonuclease does not cleave the poxviral genome. Said process may also comprise a manufacturing step, wherein said manufacturing step comprises an amplification step in a suitable producer cell to a suitable scale, a step of recovery of the produced recombinant poxvirus from the cell culture and an optional step of purification of the recovered recombinant poxvirus.

In still a further aspect, the personalized cancer vaccine is for use in a subject in need thereof for treating a cancer or preventing its relapse in a subject. Said cancer is preferably a solid tumor, and particularly, a brain or a lung cancer. In a preferred embodiment, the personalized cancer vaccine is administered in conjunction with one or more additional anti-cancer therapy/ies which have utility in the treatment of cancer.

BRIEF DESCRIPTION OF THE DRAWINGS

FIG. 1 illustrates the design of the expression cassette encoded by MVATG19022 and MVATG19023. "GS" represents 10 amino acids linkers, "Flag" the Flag tag and "SR" is the acronym for a signal peptide obtained from the rabies glycoprotein. FCU1, b-Gal, E16HPV16, E76HPV16 and MCU1 represents 27 amino acid long peptides obtained from these antigens.

FIG. 3 illustrates the amino acid sequences of the first and the second CT26 pentatope fusions expressed by MVATG19030.

FIG. 7 illustrates degenerated nucleotide sequences of 9 nucleotides encoding GSG, GTS or GAS linkers.

FIG. 8 illustrates the percentage of white plaques recovered and the number of recombinant (mCherry neg and mCherry positive) or parental (i.e. not recombinant) viruses identified by PCR following transfection of CEF cells by the plasmids indicated according to the number of fusion cassettes carried by said construct (1, 2 or 3), the number of neopeptides comprised in each fusion (Nb neo), the presence of TM segment or not TM, the hydropathy score calculated for each fusion (Hydro) and the presence and the length of linkers for each construct.

DETAILED DESCRIPTION OF THE INVENTION

General Definitions

Figure 2A:
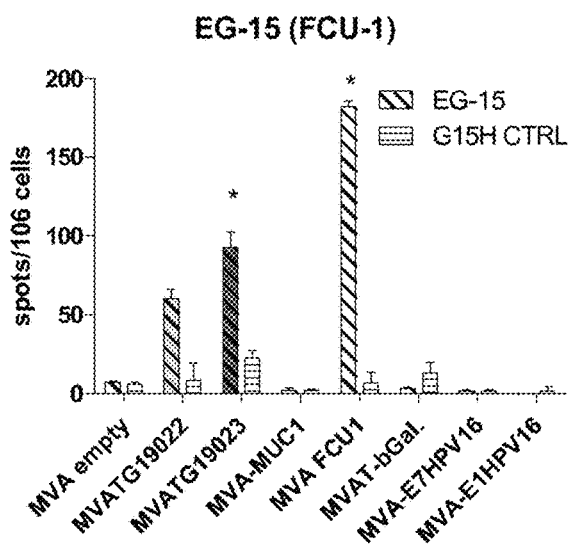
FIGS. 2 A-E illustrate ELISpot following immunization of C57bl/6 mice (5 mice per group) with peptide-encoding MVATG19022 and MVATG19023 vectors as compared to MVA vectors encoding whole antigens, respectively MUC1 (MVA-MUC1), FCU1 (MVA-FCU1), b-galactosidase (MVA-bGal), HPV-16 E7 (MVA-E7HPV16) and HPV-16 E1 (MVA-E1HPV16). Stimulation was made with either a peptide specific for each expressed antigen/peptide (respectively FCU1-specific EG15 (A), MUC1-specific L15L3 (B), E7-specific R9F (C), E1-specific 18L(D) and b-Gal-specific 18V 5E)) or with an irrelevant peptide ("CTRL" for control).
Figure 2B:
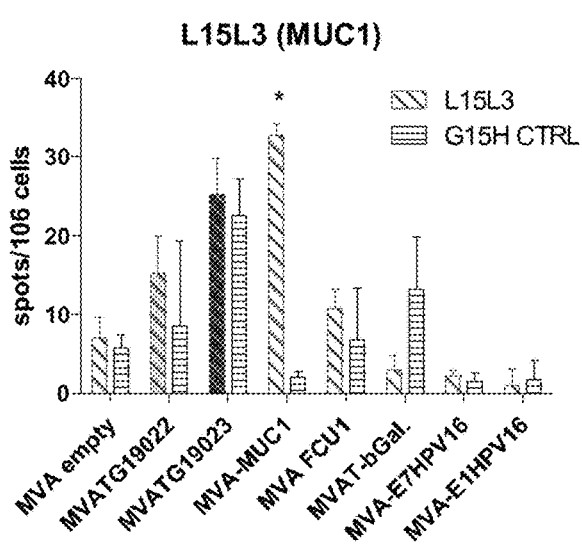

Unless defined otherwise, all technical and scientific terms used herein have the same meaning as commonly understood by one of ordinary skill in the art to which the invention pertains.

The term "a" and "an" refers to "one" or to "more than one" of the grammatical object of the article (i.e., at least one including 2, 3, 4, 5, etc) unless the context clearly dictates otherwise.

The term "and/or" wherever used herein includes the meaning of "and", "or" and "all or any other combination of the elements connected by said term".

The terms "such as", "e.g.", as used herein are for illustrative purposes and thus non-limiting.

The term "about" or "approximately" is used herein to indicate that value or range given herein is not critical and can vary within 10%, preferably within 8%, and more preferably within 5% of the given value or range so as to include the inherent variation of error for a device or a method being employed to determine such a value or range, or the variation that exists among the tested subjects.

As used herein, when used to define products, compositions and methods, the term "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are open-ended and do not exclude additional, unrecited elements or method steps. "Consisting essentially of" means excluding other components or steps of any essential significance. "Consisting of" means excluding more than trace elements of other components or steps.

The terms "polypeptide", "peptide" and "protein" are used interchangeably to refer to polymers of amino acid residues comprising at least nine amino acids covalently linked by peptide bonds. The polymer can be linear, branched or cyclic and may comprise naturally occurring and/or amino acid analogs and it may be interrupted by non-amino acids. No limitation is placed on the maximum number of amino acids comprised in a polypeptide. As a general indication, the term refers to both short polymers (typically designated in the art as peptide) and to longer polymers (typically designated in the art as polypeptide or protein). This term encompasses native polypeptides, modified polypeptides (also designated derivatives, analogs, variants or mutants), polypeptide fragments, polypeptide multimers (e.g. dimers), recombinant polypeptides, fusion polypeptides among others.

Within the context of the present invention, the terms "nucleic acid", "nucleic acid molecule", "polynucleotide", "nucleic acid sequence" and "nucleotide sequence" are used interchangeably and define a polymer of at least 9 nucleotide residues in either deoxyribonucleic acid (DNA) or ribonucleic acid (RNA) or mixed polyribo-polydeoxyribonucleotides. These terms encompass single or double-stranded, linear or circular, natural or synthetic, unmodified or modified versions thereof (e.g. genetically modified polynucleotides; optimized polynucleotides), sense or antisense polynucleotides, chimeric mixture (e.g. RNA-DNA hybrids). Exemplary DNA nucleic acids include without limitation, complementary DNA (cDNA), genomic DNA, plasmid DNA, vectors, viral DNA (e.g. viral genomes, viral vectors), oligonucleotides, probes, primers, coding DNA, non-coding DNA, or any fragment thereof etc. Exemplary RNA nucleic acids include, without limitation, messenger RNA (mRNA), precursor messenger RNA (pre-mRNA), coding RNA, non-coding RNA, etc. Nucleic acid sequences described herein may be synthesized by standard methods known in the art, e.g., by use of an automated DNA synthesizer (such as those that are commercially available from Biosearch, Applied Biosystems, etc.) or obtained from a naturally occurring source (e.g. a genome, cDNA, etc.) or an artificial source (such as a commercially available library, a plasmid, etc.) using molecular biology techniques well known in the art (e.g. cloning, PCR, etc).

Within the context of the present invention, a percent identity is determined on the basis of an optimal global alignment of sequences to be compared, i.e., on an optimal alignment of the sequences taken in their entirety over their entire length using any algorithm well-known to a person skilled in the art, such as the algorithm of Needleman and Wunsch (1970). This sequence comparison may be performed using any software well-known to a person skilled in the art, for example the Needle software by using the "Gap open" parameter equal to 10.0, the "Gap extend" parameter equal to 0.5, a "Blosum 62" matrix, the "End gap penalty" parameter to false, the "End gap open" parameter to 10, and the "End gap extend" parameter to 0.5. The Needle software is for example available at https://www.ebi.ac.uk/Tools/psa/emboss_needle/.

The terms "virus", 'viral particle", "viral vector" and virion" are used interchangeably and are to be understood broadly as meaning a vehicle comprising at least one element of a wild-type virus genome that may be packaged into a viral particle. The term encompasses the viral genome and the virus particles.

The term "obtained from", "originating" or "originate" is used to identify the original source of a component (e.g. a neoepitope, neopeptide, neoantigen, a nucleic acid molecule, a virus; etc.) or the original source of a sample (e.g. a subject or a group of subjects) but is not meant to limit the method by which the component/sample is made which can be, for example, by chemical synthesis or recombinant means.

As used herein, the term "isolated" refers to a component (e.g. a polypeptide, nucleic acid molecule, vector, etc.), that is removed from its natural environment (i.e. separated from at least one other component(s) with which it is naturally associated or found in nature). More specifically, it refers to a component that is purified (partially or substantially). For example, a nucleic acid molecule is isolated when it is separated of sequences normally associated with it in nature (e.g. dissociated from a chromosome or a genome) but it can be associated with heterologous sequences (e.g. within a recombinant vector). A synthetic component is isolated by nature.

The term "subject" generally refers to a vertebrate organism for whom any of the product or methods disclosed herein is needed or may be beneficial. Typically, the organism is a mammal, particularly a mammal selected from the group consisting of domestic animals, farm animals, sport animals, and primates (human and non-human). The terms "subject" and "patient" may be used interchangeably when referring to a human organism and covers male and female as well as a fetuses, newborn, infant, young adult, adult and elderly.

As used herein, the term "tumor" may be used interchangeably with any of the terms "cancer", "malignancy", "neoplasm" and encompasses any disease or pathological condition resulting from uncontrolled cell growth and spread. These terms are meant to include any type of tissue, organ or cell, any stage of malignancy (e.g. from a prelesion to stage IV). Typically, tumors, especially malignant tumors, show partial or complete lack of structural organization and functional coordination as compared to normal tissue and generally show a propensity to invade surrounding tissues (spreading) and/or metastasize to farther sites. The present invention is preferably designed for the treatment of solid tumors as described herein.

A "neoplastic cell", "cancer cell" or "tumor cell" can be used interchangeably to refer to a cell that divides at an abnormal (i.e. increased) rate.

The term "treatment" (and any form of treatment such as "treating", "treat", etc.,) as used herein refers to prophylaxis and/or therapy. Typically, «prophylaxis» refers to prevention, e.g. to prevent, delay the onset or decrease the severity of the first occurrence or relapse of at least one clinical or biochemical symptom (size of tumor, expression level of associated biomarker, stage progression . . . ) whereas therapy refers to a pathological condition with the purpose to improve at least one clinical or biochemical symptom (size of tumor, expression level of associated biomarker . . . ), to slow down or control the progression of the targeted pathological condition, symptom(s) thereof, or a state secondary to the pathological condition in the subject treated in accordance with the present invention.

The term "administering" (or any form of administration such as "administered", etc.,) as used herein refers to the delivery to a subject of a component (e.g. at least a neopeptide-encoding poxvirus) according to the modalities described herein.

Personalized Cancer Vaccine

In a first aspect, the present invention relates to a personalized cancer vaccine comprising a recombinant poxvirus encoding one or more neopeptide(s).

"Personalized" as applied herein to characterize the cancer vaccine of the invention refers to either the individual level (a specific subject) or a subpopulation level (a small group of persons sharing a common feature, e.g. having a specific disease, a specific phenotypic feature, or taking the same drug or showing the same deficiency e.g. in the immune system).

Poxvirus

As used herein the term "poxvirus" refers to a virus belonging to the Poxviridae family with a preference for the Chordopoxvirinae subfamily directed to vertebrate host which includes several genus such as *Orthopoxvirus, Capripoxvirus, Avipoxvirus, Parapoxvirus, Leporipoxvirus* and *Suipoxvirus*. *Orthopoxviruses* are preferred in the context of the present invention as well as the *Avipoxviruses* including *Canarypoxvirus* (e.g. ALVAC) and Fowlpoxvirus (e.g. the FP9 vector). In a preferred embodiment, the cancer vaccine comprises a poxviral vector belonging to the Orthopoxvirus genus and even more preferably to the vaccinia virus (VV) species. Any vaccinia virus strain can be used in the context of the present invention including, without limitation, Western Reserve (WR), Copenhagen (Cop), Lister, LIVP, Wyeth, Tashkent, Tian Tan, Brighton, Ankara, MVA (Modified vaccinia virus Ankara), LC16M8, LC16M0 strains, etc., with a specific preference for WR, Copenhagen, Wyeth and MVA vaccinia virus. Sequences of the genome of various Poxviridae, are available in the art in specialized databanks such as Genbank (e.g. accession numbers NC_006998, M35027, NC_005309, U94848 provide sequences of WR, Copenhagen, Canarypoxvirus and MVA genomes).

Another appropriate embodiment is directed to a cancer vaccine comprising a poxviral vector belonging to the Parapoxvirus genus. Like other members of the Poxviridae family, parapoxvirus are relatively large and enveloped double-stranded DNA viruses with ovoid geometries that can infect vertebrates including a wide selection of mammals and humans. Parapoxviruses have a unique spiral coat that distinguishes them from other poxviruses. Such a genus encompasses a series of different species including Parapoxvirus ovis (ORFV), pseudocowpox virus (PCPV) and bovine papular stomatitis virus and different strains thereof (e.g. ORFV 01701, NZ2, NZ7 and OV-SA00 strains and bovine popular stomatitis virus BV-AR02 strain) that may have morphological, structural and/or genetic differences each other. In the context of the present invention, preference is given to a PCPV species. PCPV possesses a genome which is a linear and double-stranded segment of DNA, typically of 130-150 kilobases.

In the context of the present invention, one may use either a wild-type strain as well as any derivative thereof (i.e. a poxvirus that is modified compared to the wild-type strain, e.g. by truncation, deletion, substitution, and/or insertion of one or more nucleotide(s) contiguous or not within the viral genome). Modification(s) can be within endogenous viral genes (e.g. coding and/or regulatory sequences) and/or within intergenic regions. Moreover, modification(s) can be silent or not (e.g. resulting in a modified viral gene product). Modification(s) can be made in a number of ways known to those skilled in the art using conventional molecular biology techniques. The present invention includes oncolytic (e.g. engineered to replicate better or selectively in tumor cells) as well as replication-defective poxviruses.

Preferably, the modifications encompassed by the present invention affect, for example, virulence, toxicity, pathogenicity or replication of the virus compared to a virus without such modifications. Exemplary modifications aimed at altering viral genes are preferably involved in DNA metabolism, host virulence or IFN pathway (see e.g. Guse et al., 2011, Expert Opinion Biol. Ther. 11(5):595-608). A particularly suitable gene to be disrupted is the thymidine kinase (TK)-encoding gene (locus J2R; Genbank accession number AAA48082). The TK enzyme is involved in the synthesis of deoxyribonucleotides. TK is needed for viral replication in normal cells as these cells have generally low concentration of nucleotides whereas it is dispensable in dividing cells which contain high nucleotide concentration. Further, inactivation of the TK gene is known to increase selectivity to tumor cells. Alternatively to or in combination with, the poxvirus for use herein may be modified by altering at least one gene or both genes encoding viral ribonucleotide reductase. The viral enzyme is similar in subunit structure to the mammalian enzyme, being composed of two heterologous subunits, designed R1 and R2 encoded respectively by the I4L and F4L locus. Sequences for the I4L and F4L genes and their locations in the genome of various poxvirus are available in public databases. Other suitable modifications include those altering the deoxyuridine triphosphatase (F2L), the viral hemagglutinin (A56R); the serine protease inhibitor (B13R/B14R) and the complement 4b binding protein (C3L). The gene nomenclature used herein is that of Copenhagen Vaccinia strain. It is also used herein for the homologous genes of other poxviridae unless otherwise indicated and correspondence between Copenhagen and other vaccinia strains is available to the skilled person. For illustrative purposes, vaccinia viruses (VV) defective for TK, TK- and F2L and TK- and I4L are described in the literature (see e.g. WO2009/065547 and WO2009/065546).

In a preferred embodiment, the poxvirus comprised in the cancer vaccine of the invention is a replication-defective poxvirus, and preferably a replication defective vaccinia virus, which means that it cannot replicate to any significant extent in human cells. The poxviral vector can be rendered replication-defective by partial or total deletion or inactivation of regions critical to viral replication and the impairment or defectiveness of replication functions can be evaluated by conventional means, such as by measuring DNA synthesis and/or viral titer in non-permissive cells.

A particularly appropriate poxviral vector for use in the context of the present invention is MVA due to its highly-attenuated phenotype (Mayr et al., 1975, Infection 3: 6-14; Sutter and Moss, 1992, Proc. Natl. Acad. Sci. USA 89: 10847-51) and a more pronounced IFN-type 1 response generated upon infection compared to non-attenuated poxvirus. For illustrative purposes, MVA has been generated through serial passages in chicken embryo fibroblasts. Sequence analysis of its genome showed that it has lost the pathogenicity of its parental virus, the Chorioallantois Vaccinia virus Ankara, through alterations of its genome. (Antoine et al., 1998, Virol. 244: 365-96 and Genbank accession number U94848). MVA has been used safely and effectively for small pox vaccination in more than a hundred thousand individuals. Replicative potential of the virus in human cells is also defective but not in chicken embryo cells. Various cellular systems are available in the art to produce large quantities of the virus, notably in egg-based manufacturing processes (e.g. WO2007/147528).

The term "recombinant" refers to a poxvirus comprising inserted in its genome at least one exogenous nucleic acid molecule (e.g. one or more nucleic acid molecules encoding neopeptides) as described hereinafter.

Type and Number of Neopeptides

For sake of clarity, an "antigen" generally refers to a substance (e.g. a polypeptide) capable of raising a humoral or a specific T cell response (or both) against that antigen, including a CD4+ (e.g., Th1, Th2 and/or Th17) and/or a CD8+ T cell response (e.g., a CTL response). A vast variety of direct or indirect biological assays are available in the art to evaluate the immunogenic nature of an antigen either in vivo (animal or human being) or in vitro (e.g. in a biological sample) as described herein.

To be detectable by the immune system, antigens are processed, and this processing requires antigen fragmentation into peptides, association of peptides with MHC (major histocompatibility complex; HLA for "Human Leucocyte Antigen» in humans) and presentation of peptide-MHC complex at cell surface where they can be recognized by a T cell through the T cell receptor (TCR). These antigen-derived peptides include a minimal immune determinant (i.e. an epitope). There are two types of MHC molecules: MHC class I and MHC class II. MHC class I molecules are present at the surface of all nucleated cells of mammalian subjects and peptide/MHC class I complexes trigger $CD8^+$ CTL activation. In contrast, MHC class II molecules are normally present only at the surface of specialized antigen-presenting cells, such as dendritic cells, mononuclear phagocytes, some endothelial cells, thymic epithelial cells, and B cells and peptide presentation though MHC class II molecules generally drives a CD4+ T cell response. Epitopes for presentation through MHC class I molecules are generally at least 8 amino acids long, preferably 8, 9 or 10 amino acids whereas MHC-class II epitopes are usually longer (e.g. at least 13 amino acid residues (Rock et al., 2010, J. Immunol. 184(1): 9-15). A large number of prediction algorithms exists in the art for in silico prediction of MHC class I and class II binding (see e.g. Nielsen et al., 2010, Immunology 130(3): 319-28). For illustrative purposes, one may cite SVMHC, NetMHCII, Tepitope/propped, syfpeithi, Epitollkit, etc.

The term "neoantigen" as used herein refers to an antigen that has emerged during the carcinogenesis process in a cancer cell. In a preferred embodiment, a neoantigen comprises one or more non-silent mutation(s) of amino acid residue(s) with respect to a corresponding wild-type antigen. Typically, a non-silent mutation occurs at the nucleotide level and translates in a change at the amino acid level. In another preferred embodiment, the neoantigen is found in cancer cells or tissues obtained from a patient but not found in a sample of normal cells or tissues obtained from a patient or a healthy individual.

The term "neopeptide" refers to a fragment of a neoantigen comprising a neoepitope, as well as flanking sequence (s) on one or both side(s) of the neoepitope. The flanking sequences are those of the neoantigen from which the neoepitope is taken. A neopeptide thus corresponds to a fragment of a neoantigen that is longer than the neoepitope itself that is presented by MHC molecules. In the neopeptide, the neoepitope is thus present and surrounded (on either or both side(s)) by a flanking sequence(s) naturally present in its normal environment. Except in rare cases when the neopeptide is also present in another self-protein, the neopeptide will in most cases (and may be selected to, see below) be of nonself-nature. Due to this non-self-nature, it is expected that such neopeptide(s) will be recognized by the tumor specific T lymphocytes.

The term "neoepitope" as used herein refers to a minimal immune determinant of a neoantigen that contributes to MHC-dependent T cell recognition (or that is presented by MHC molecules at the surface of cells of the subject) and comprising at least one of the non-silent mutation(s) identified in said neoantigen according to the modalities described herein.

The term "mutation" relates to at least one sequence difference between a test sequence and a reference sequence.

In one embodiment, each of the one or more neopeptide(s) encoded by the recombinant poxvirus is specific for the patient's tumor and comprises at least one tumor-specific mutation from the set of mutations described herein. In the context of the present invention, a "tumor-specific mutation" relates to a mutation that is generated along neoplastic transformation and/or progression of the cancer cell. Typically, a tumor-specific mutation is preferably present in the DNA contained in a cancer cell (e.g. the tumor sample) but absent in the DNA contained in a non-cancerous cell (e.g. the non-tumor sample). Although occurring at the nucleotide level, in the context of the present invention, a tumor-specific mutation is non-silent and translates in a change at the amino acid level.

Several types of tumor-specific mutations are encompassed by the present invention, including missense mutations, deletions, insertions, frameshift mutations, and mutations in splicing site. A "missense" mutation results from the substitution of one nucleotide with another nucleotide within a specific codon that affects the encoded amino acid sequence, thus resulting in one amino acid change. Another way to affect a protein sequence, is an insertion or a deletion of one or more nucleotide(s) (e.g. a piece of DNA) which changes the number of nucleotides in a nucleic acid molecule. Insertion and deletion mutations may result in change of the reading frame (a so-called frame shift mutation) but not necessarily (e.g. the insertion or deletion of 3 nucleotides will result in the addition or suppression of a codon). The almost entire polypeptide may be changed if the mutation occurs early in the nucleotide sequence. A frameshift mutation may also result in the generation of a stop codon that is translated into a stop signal and the resulting protein will then be truncated (deleted of its portion downstream the de novo generated stop codon). A missense mutation may also be located in the splicing sites of the mRNA leading to an aberrant splicing and therefore to aberrant protein sequence. The term "splicing" relates to the editing of the nascent precursor messenger RNA (pre-mRNA) transcript. After splicing, introns are removed and exons are joined together (ligated). The term "splicing site" relates to short conserved sequences located at the ends of introns that are crucial for intron recognition and for the accuracy of the splicing reactions.

The present invention encompasses neopeptides originating from all protein classes, such as enzymes, receptors, transcription factors, etc. Although any type of mutations may be present, however, the tumor-specific mutation is preferably missense or frameshift. Advantageously, at least 60%, desirably at least 65%, preferably at least 70%, more preferably, at least 75%, at least 80% (e.g. 81%, 82%, 83%, 84%, 85%, 86%, 87%, 88%, 89%, 90%, 91%, etc), at least 85% (e.g. 85%, 86%, 87%, 88%, 89%, 90%, 91%, etc), at least 90% (e.g. 90%, 91%, 92%, 93%, 94%, 95%, 96%, 97%, 98%, 99%, or even 100%), at least 91%, at least 92%, at least 93%, at least 94%, at least 95%, at least 96%, at least 97%, at least 98%, at least 99%, or even 100% of the neopeptides for use herein comprise a missense or frameshift mutation. Among missense and frameshift mutations, missense mutations are more frequent. In certain embodiments, at least 60%, desirably at least 65%, preferably at least 70%, more preferably, at least 75% and even more preferably at least 80% (e.g. 81%, 82%, 83%, 84%, 85%, 86%, 87%, 88%, 89%, 90%, 91%, etc), at least 85% (e.g. 85%, 86%, 87%, 88%, 89%, 90%, 91%, etc), at least 90% (e.g. 90%, 91%, 92%, 93%, 94%, 95%, 96%, 97%, 98%, 99%, or even 100%), at least 91%, at least 92%, at least 93%, at least 94%, at least 95%, at least 96%, at least 97%, at least 98%, at least 99%, or even 100% of the neopeptides for use herein comprise a missense mutation. However, if frameshift mutations are identified, it is also preferred that one or more of the neopeptide(s) encoded by the recombinant poxvirus comprise a frameshift mutation. For instance, for 10 neopeptides encoded by the recombinant poxvirus, preferably at least 6, at least 7, at least 8, at least 9 or even 10 of the neopeptides are missense or frameshift mutations, and more preferably at least 6, at least 7, at least 8, at least 9 or even 10 of the neopeptides are missense mutations. Similarly, for 30 neopeptides encoded by the recombinant poxvirus, preferably at least 18, at least 19, at least 20, at least 21, at least 22, at least 23, at least 24, at least 25, at least 26, at least 27, at least 28, at least 29 or even 30 of the neopeptides are missense or frameshift mutations, and more preferably at least 18, at least 19, at least 20, at least 21, at least 22, at least 23, at least 24, at least 25, at least 26, at least 27, at least 28, at least 29 or even 30 of the neopeptides are missense mutations. Those skilled in the art will easily adapt these examples to poxviruses encoding other numbers of neopeptides.

The length of the neopeptides encoded by the recombinant poxvirus is generally comprised between 13 amino acid residues to about 151 amino acid residues but of course the length can vary from one neopeptide to another. Advantageously, each of the neopeptide(s) for use herein has a length from 15 to 101 amino acid residues, desirably from 16 to 90 amino acid residues, preferably from 17 to 85 amino acid residues and more preferably from 18 to 80 amino acid residues. Advantageously, at least 70% of the neopeptides for use herein have an odd number of amino acids, since, in the case of a single missense mutation, this permits to insert it in the center of the neopeptide, with the same number of flanking amino acids on either side of the mutated amino acid. Of course, the neopeptide's length may also be dependent of the type of mutation. For illustrative but not limitative purposes, neopeptides comprising a missense mutation preferably have a length from 18 to 29 residues whereas those comprising a frameshift mutation preferably have a length from 30 to 80 amino acid residues. In the context of the present invention, at least 60%, preferably at least 70% and more preferably at least 80%, at least 85%, at least 90%, at least 91%, at least 92%, at least 93%, at least 94%, at least 95%, at least 96%, at least 97%, at least 98%, at least 99%, or even 100% of the neopeptides encoded by the poxvirus cancer vaccine of the invention preferably have a length from 18 to 29 residues. Particular preference is given to individual neopeptides of 19, 21, 26, 27 or 29 residues. In a particularly preferred embodiment, at least 60%, preferably at least 70% and more preferably at least 80%, at least 85%, at least 90%, at least 91%, at least 92%, at least 93%, at least 94%, at least 95%, at least 96%, at least 97%, at least 98%, at least 99%, or even 100% of the neopeptides encoded by the poxvirus cancer vaccine of the invention comprise a missense mutation and have a length from 18 to 29 residues, in particular 19, 21, 26, 27 or 29 residues.

Concerning the position of the mutation, the present invention contemplates any position within the neopeptide. Central position is however particularly preferred for a missense mutation. By "central position" it is meant that the mutated amino acid is exactly positioned in the middle of the neopeptide (in case the neopeptide has an odd number of amino acids) or at one of the two central position (in case the neopeptide has an even number of amino acids), or at any of the 2 to 5 amino acids on each side of the exact central position, depending of the neopeptide length. Desirably, at least 80%, preferably at least 85%, more preferably at least 90%, at least 91%, at least 92%, at least 93%, at least 94%, at least 95%, at least 96%, at least 97%, at least 98%, at least 99%, or even 100% of neopeptides having a missense mutation, carry the substituted amino acid in central position as defined above. Specifically preferred are neopeptides of 19, 21, 27 or 29 amino acids (even more preferably 27 or 29 amino acids) bearing the missense mutation in exact central position (e.g. at position for a 19mer neopeptide, at position 11 for a 21mer neopeptide, at position 14 for a 27mer neopeptide and at position 15 for a 29mer neopeptide).

The mutation may however, at least in some of the neopeptides, be located close to N-terminus or C-terminus, especially for a frameshift mutation or when the missense mutation occurs at or close to the N or C-terminus of the neoantigen.

Some embodiments also contemplate expression of neopeptides by the recombinant poxvirus in the form of one or more fusion(s). The term "fusion" as used herein refers to the combination of two or more neopeptides in a single polypeptide chain. The fusion can be direct (i.e. without any additional amino acid residues in between) or through a linker to improve accessibility of the neopeptides. Further to series of unique neopeptides expressed individually, the present invention thus also encompasses recombinant poxvirus expressing several neopeptides in the form of fusion(s) and some others individually. Alternatively, all neopeptides expressed by the poxviral vector are clustered in one or more fusion(s).

Certain embodiments contemplate the presence of a signal peptide at the N-terminus of the encoded neoepitope(s) (or fusion thereof) to enhance the processing through ER (endoplasmic reticulum)- and/or secretion. Briefly, signal peptides usually comprise 15 to 35 essentially hydrophobic amino acids, are inserted at the N-terminus of the polypeptide downstream of the codon for initiation of translation and are then removed by a specific ER-located endopeptidase to give the mature polypeptide. Membrane anchorage may also be used to improve MHC class I and/or MHC class II presentation of the encoded neopeptides (or fusion thereof) by further incorporating a membrane-anchoring sequence. Trans-membrane peptides are highly hydrophobic in nature and serve to anchor the polypeptides within cell membrane. They are preferably inserted within the C-terminal part of the polypeptide, preferably immediately upstream of the stop codon. Appropriate trans-membrane and/or signal peptides are known in the art. They may be obtained from cellular or viral polypeptides such as those of immunoglobulins, tissue plasminogen activator, insulin, rabies glycoprotein, the HIV virus envelope glycoprotein or the measles virus F protein or may be synthetic. Preferred signal peptides and membrane-anchoring sequences are described in WO2008/138649, with a preference for those originating from the rabies or the measles F glycoprotein. If more than a signal peptide and/or trans-membrane sequence is to be used in the recombinant poxvirus, one may choose ones of different origin or degenerate the homologous sequences that show a high degree of sequence identity (e.g. above 75%) so as to limit homologous recombination events that might deteriorate the production process.

Alternatively to or in combination with the previous embodiment, the present invention contemplates the presence of one or more linker(s) (also called spacer), especially in neopeptides fusion. Typically, linkers are 1 to 30 amino acids long peptides composed of amino acid residues such as glycine, serine, threonine, asparagine, alanine and/or proline. Preferred linkers in the context of this invention comprise 2 to 15 amino acids, with a preference for 3, 5, or 10 amino acids, mainly glycine and serine (e.g. GSG, GSGSG (SEQ ID NO: 66), SGSGS (SEQ ID NO: 67), GSGSGSGSGS (SEQ ID NO: 68)) or glycine, serine and threonine (e.g. GSTSG (SEQ ID NO: 69), SGTGS (SEQ ID NO: 70)) or glycine, serine, and threonine and/or alanine (e.g. GAS, GTS). Preferred linkers of 3 amino acids notably include linkers of sequences GSG, GAS, and GTS. It is within the reach of the skilled person to assess the need to include a linker or not between two fused neopeptides.

In a preferred embodiment, neopeptides are arranged in fusion(s) with linkers in between each neopeptide (e.g. between neopeptide 1 and neopeptide 2, between neopeptide 2 and neopeptide 3, etc,) and, optionally, at the N terminus of the first neopeptide and/or at the C terminus of the last neopeptide. When several linkers are to be used within one construct, one may vary the amino acid sequence or the codon nucleic sequence to decrease the percentage of identity at the nucleic level (e.g. to less than 77% identity, desirably less than 75%, less than 70%, preferably less than 60%, less than 50% and even more preferably less than 35% especially for linkers of 10 amino acids) and thus limit recombination events during the production process. In preferred embodiments, the linkers nucleic sequences comprised in one recombinant poxvirus are designed (by changing amino acid sequence or codon nucleic sequence) so as that portions of nucleic sequence identical between any two of the linkers are reduced to a maximum of 8 contiguous nucleotides (e.g. preferably a maximum of 7 and more preferably a maximum of 6 contiguous nucleotides), thus contributing to reduce the nucleic sequence identity as described above and thus to limit undesirable recombination events during the production process. As illustrated in the examples section, short linkers of 2 to 5 amino acid residues (e.g. 2, 3, 4 or 5 amino acids) are advantageous especially when the recombinant poxvirus encodes 10 or more neopeptides. Three amino acid linkers such as GSG, GAS and/or GTS are particular preferred in the context of the invention to separate neopeptides from each other. Exemplary nucleotide sequences encoding 3 amino acid linkers are given in FIG. 7 to be used individually or in combination in neopeptides fusion(s) as described herein. For illustrative purpose, 15 GSG-encoding nucleotide sequences have been generated and degenerated by taking advantage of the codon degeneracy (4 codons possible for G and 6 for S) to reduce the risk of homologous recombination in the recombinant poxvirus that may occur between stretches of identical or similar sequences. On the same line, 10 and 5 degenerated nucleotide sequences encoding GTS and GAS linkers respectively are provided in FIG. 7.

Certain embodiments of the present invention contemplate the presence of a tag in order to facilitate the detection of the expression of the neopeptides (or fusion(s) thereof) or of infected host cells expressing such neopeptides or fusion thereof. Tag peptides can be detected by immunodetection assays using anti-tag antibodies. A vast variety of tag peptides can be used in the context of the invention including without limitation PK tag, FLAG tag (DYKDDDK; SEQ ID NO: 6), MYC tag (EQKLISEEDL SEQ ID NO: 11), polyhistidine tag (usually a stretch of 5 to 10 histidine residues;), HA tag (YPYDVPDYA; SEQ ID NO: 18), HSV tag (QPELAPEDPED; SEQ ID NO: 19) and VSV Tag (YTDIEMNRLGK; SEQ ID NO: 20). The tag peptide may be independently positioned at the N-terminus of the neopeptide or fusion thereof (tag-polypeptide) or alternatively at its C-terminus (polypeptide-tag) or alternatively internally.

The number of neopeptides that can be encoded by the recombinant poxvirus is not limiting depending on the type of expression selected (individual expression, expression in short or large fusions as described hereinafter) and the type of poxvirus. For illustrative purposes, 1 to 50 neopeptides may be expressed by the recombinant poxvirus, more preferably from 5 to 45 and even more preferably from 6 to 35 with a preference for 10 to 30 neopeptides.

In preferred embodiments, several and preferably all neopeptides are expressed by the recombinant poxvirus in the form of one or more fusion(s). Preferably, the poxvirus comprised in the personalized cancer vaccine of the invention encodes 1 to 5 fusions of 2 or more neopeptides, preferably 1 to 4 fusions of 2 or more neopeptides and more preferably 1 to 3 fusions of 2 or more neopeptides, with a specific preference for 2 or 3 fusions of 2 or more neopeptides. More preferably, each fusion comprises 2 to 15 neopeptides, preferably, 3 to 12 neopeptides, more preferably 4 to 11 neopeptides, and even more preferably, 5 to 10 neopeptides (e.g. 5, 6, 7, 8, 9 or 10). The number of neopeptides may vary from one fusion to another fusion encoded by the recombinant poxvirus. However, in a particularly preferred embodiment, the poxvirus comprised in the personalized cancer vaccine of the invention encodes 2 or 3 fusions of 5 to 10 neopeptides.

In the context of the present invention, each fusion may be designed differently from the other(s) and may distinguish one another by the presence, and/or the sequence and/or the number and/or the positioning of elements such as peptide signals, linkers, tags, etc. According to a preferred embodiment, each fusion however comprises a) a signal peptide at its N terminus, b) linkers at the N-terminus of the first neopeptide, between each neopeptides and at the C-terminus of the last neopeptide and c) a tag at its C-terminus.
Prediction of the Presence of TM (Transmembrane) Segment(s) in the Neopeptides and fusion(s) thereof In one embodiment, the amino acid sequence of the one or more neoepitope(s) or fusion(s) thereof encoded by the recombinant poxvirus does not comprise any potential transmembrane segment. A TM segment can be defined as being a short hydrophobic alpha helix of approximately 20 residues (e.g. 18 to 30 residues with a preference for 19 to 21 residues). Several prediction tools can be used to predict the probability that a given sequence (e.g. a particular neopeptide or a fusion of neopeptides) comprises a TM segment or not, such as TMHMM (for Transmembrane Hidden Markov Model; Krogh et al., 2001, J. Mol. Biol. 305: 567-80) and DAS (Dense Alignment Surface). For example, DAS-TM filter algorithm provides a high precision hydrophobicity profile for the query from which the location of the potential transmembrane segments can be obtained.

In a preferred embodiment, at least 80% (e.g. at least 85%, at least 90%, at least 95%, at least 98% and even 100%) of the neopeptides encoded by the poxvirus comprised in the personalized cancer vaccine of the present invention do not comprise potential TM segment(s) (intra peptide TM). In this context, neopeptides which are predicted to comprise a TM segment are preferably not selected.

Even more preferably, prediction of the presence of TM segment is also applied to each neopeptide fusion. It has been indeed observed that TM segment may be generated by the junction of 2 particular neopeptides (inter peptide TM). In this case, modifying the order of neopeptides in the fusion is an option to eliminate the presence of TM. For instance, if a TM segment results from the fusion of neopeptide 1 at the N-terminus of neopeptide 2, inverting the neopeptides (fusion of neopeptide 2 at the N-terminus of neopeptide 1) may eliminate the risk of having a TM segment. Another option may be the addition of an appropriate linker between the 2 fused neopeptides.
Prediction of the Hydrophobicity and Hydropathy Scores of the Neopeptides and Fusion(s) Thereof In one embodiment, the amino acid sequence of the one or more neoepitope(s) or fusion(s) thereof encoded by the recombinant poxvirus is hydrophilic in nature. The hydrophilic or hydrophobic nature of a given sequence can be easily determined by a number of methods and algorithms available in the art. It is within the reach of the man skilled in the art to calculate the hydrophobicity score and/or the hydropathy score of a specific sequence. For instance, these scores can be determined using the Kyte-Doolittle method (Kyte and Doolittle, 1982, J. Mol. Biol. 157: 105-32) or any other suitable method (e.g. Rose et al., 1993, Ann. Rev. Biomol. Struc. 22: 381-415; Kallol et al., 2003, J. Chromat. 1000: 637-55; Sweet et al., 1983, J. Mol. Biol. 171: 479-88; among many others) or algorithm (e.g. ExPASy Prot Scale Protein; Protein Hydrophobicity Plots developed by Colorado state or the World of Bioinformatics, etc). In a general manner, the hydrophobicity score of a given sequence is determined by the sum of the hydrophobicity/hydrophilicity value of each amino acid residue which is summarized in the following Table 1.

| Amino Acid | One Letter Code | Hydrophobicity/ hydrophilicity value |
|---|---|---|
| Isoleucine | I | 4.5 |
| Valine | V | 4.2 |
| Leucine | L | 3.8 |
| Phenylalanine | F | 2.8 |
| Cysteine | C | 2.5 |
| Methionine | M | 1.9 |
| Alanine | A | 1.8 |
| Glycine | G | −0.4 |
| Threonine | T | −0.7 |
| Serine | S | −0.8 |
| Tryptophan | W | −0.9 |
| Tyrosine | Y | −1.3 |
| Proline | P | −1.6 |
| Histidine | H | −3.2 |
| Glutamic acid | E | −3.5 |
| Glutamine | Q | −3.5 |
| Aspartic acid | D | −3.5 |
| Asparagine | N | −3.5 |
| Lysine | K | −3.9 |
| Arginine | R | −4.5 |

As illustrated in Table 1, I, V, L, F, C, M and A amino acids display a positive hydrophobicity score (e.g. 4.5 for I) correlating with the hydrophobic nature of these residues whereas G, T, S, W, Y, P, H, E, Q, D, N, K and R display a negative hydrophobicity score (e.g. −4.5 for R) correlating with their hydrophilic nature.

The hydrophobicity score of a given neopeptide is determined by the sum of the hydrophobicity/hydrophilicity value of each amino acid residue comprised in said neopeptide and hydropathy score is calculated by dividing the hydrophobicity score determined for said neopeptide by the number of residues present in this peptide. The hydrophobicity score of a given neopeptide fusion corresponds to the sum of the hydrophobicity scores determined for each neopeptide comprised in said fusion. The hydropathy score of a given neopeptide fusion is calculated by dividing the hydrophobicity score determined for said neopeptide fusion by the number of residues present in this neopeptide fusion.

In a preferred embodiment, at least 60% of the neopeptides encoded by the recombinant poxvirus comprised in the personalized cancer vaccine of the present invention displays a negative hydrophobicity score and/or a hydropathy score equal or below 0.1 (e.g. 0.1, 0.09, 0.08, etc or even a negative score e.g. −0.019, −1.5, etc). On the same line, each fusion encoded by the recombinant poxvirus for use herein preferably scores negatively for hydrophobicity and/or equal or below 0.1 for hydropathy. "At least 60%" encompasses at least 65%, at least 70%, at least 75%, at least 80%, at least 85%, at least 90%, at least 95%, at least 98% and even 100%.

For illustrative purpose, a neopeptide of sequence GQSLPMTHSLKLSKTNRTLFLLGVTKY (SEQ ID NO: 58) has a negative hydrophobicity score of −3,6 (addition of −0.4 for G, −3.5 for Q, −0.8 for S, +3.8 for L, etc) and a hydropathy score of −0.13 (−3.6/29). Thus, this peptide will be suitable for being expressed by the recombinant poxvirus comprised in the personalized cancer vaccine of the present invention. In contrast, the neopeptide GLMGIVVGTVFIIRGLRSVGASRHQGL (SEQ ID NO: 59) scores positively for hydrophobicity (23.3) and has a hydropathy score of 0.86. Thus, this peptide is not appropriate for being expressed by the recombinant poxvirus comprised in the personalized cancer vaccine of the present invention unless the other neopeptides comprised in the fusion compensate allowing to lower the global score of the fusion to the appropriate threshold described herein.

In a particularly preferred embodiment, the recombinant poxvirus comprised in the personalized cancer vaccine of the invention encodes 2 or 3 fusions, wherein:
  each fusion comprises 5 to 10 neopeptides; has linkers, preferably 3 amino acid long, at the N-terminus of the first neopeptide of said fusion and between each neopeptide (e.g. one or more of those shown in FIG. 7);
  each fusion comprises a signal peptide at the N-terminus of said fusion;
  each fusion optionally comprises a tag sequence at the C-terminus of said fusion; and
  each fusion:
    displays a global negative hydrophobicity score and/or a global hydropathy score equal or below 0.1, and
    does not comprise any potential TM segment.

Identification of the Neoantigens and the Neopeptides to be Encoded by the Personalized Cancer Vaccine The development of a personalized cancer vaccine requires the identification and selection of neopeptides on a patient by patient basis.

Accordingly, the present invention relates to a process for preparing a personalized cancer vaccine comprising a step of identifying one or more neopeptide(s) suitable for being encoded by the recombinant poxvirus wherein each of said neopeptides comprises at least one tumor-specific mutation.

For this purpose, a tumor biological sample is obtained from the subject to be treated as well as a non-tumor biological sample. The term "biological sample" as used herein refers to a sample obtained from a subject which can be taken or collected in vivo. In the context of the invention, the biological sample(s) taken or collected from the subject contains DNA, and preferably also contains mRNA or proteins.

In one embodiment, the biological sample is obtained from a body fluid or from a tissue sample. Exemplary body fluid samples include, but are not limited to, blood, serum, plasma, urine, stool, cerebral spinal liquid and bronchial liquid as well as any derivative thereof (e.g. partially purified blood, PBMCs). Tissue samples can be, but are not limited to, organs, tissues, fractions and cells isolated from a mammal from any origin or cell type (e.g. samples comprising oral, gastrointestinal, skin, lung, head, etc., tissue-). Exemplary tissue samples include, e.g. cell lysate, cell cultures, tissues, fresh frozen tissues, cytological material (e.g. cervical smear, vaginal swab, bronchial brushings, pleural fluids, coloscopy, etc.,), tissues obtained after surgical tumor removal as well as tissue biopsies. In the context of the present invention, the biological sample may be in suspension or solution or still be affixed to a solid support (e.g. slides, beads, chips or nanoparticles). The present invention also encompasses "purified" or semi "purified" biological samples, e.g. isolated RNA, cDNA, isolated protein, etc.

In one and preferred embodiment, the tumor sample is a tumor biopsy, preferably comprising more than 20% of tumor cells. It may be prepared in any manner, including but not limited to dissociated tissue specimens, such as fine needle aspirates or fresh solid tumors (which can be enzymatically digested) or a microtome section of a biopsy. In another embodiment, the tumor sample is a cytological material (e.g. cervical or vaginal swab).

In still another embodiment, the non-tumor sample is obtained from a biological fluid (e.g. blood with or without PBMC isolation), a cytological material (e.g. buccal swab), a biopsy (e.g. a biopsy of a healthy tissue) or a piece of surgical resection containing non-tumor cells. The non-tumor sample can be taken or collected from the same patient or from a reference healthy subject or group of subjects.

In the case where the tumor and non-tumor samples originate from the same sampling, the skilled person knows how to recognize and separate tumor cells from non-tumor cells (e.g. by immunohistology).

In one embodiment, the identification step comprises:
  a) extracting the DNA from said tumor sample and said non-tumor sample,
  b) selecting target regions, preferably the entire coding regions of the genome (exome),
  c) sequencing said target regions (e.g. the exome) from said extracted DNAs and
  d) identifying one or more tumor-specific mutation(s) by comparing the DNA sequences obtained from said tumor and non-tumor samples.

The term "exome" refers to the part of the genome formed by exons (i.e. the sequences which when transcribed remain within mRNA after introns removal by RNA splicing). For illustrative purpose, the exome of the human genome consists of about 180,000 exons corresponding to about 1% of the total genome. Techniques for exome sequencing are well known in the art (Anderson and Schrijver, 2010, Genes 1(1): 38-69). Generally, methods involve a two stage approaches: first a targeted capture of coding sequences using array-based hybridization (commercially available from Agilent technologies) or liquid-based hybridization (commercially available as NimbleGen from Roche; Bainbridge et al., 2010, Genome Biol. 11:R62); the capture stage is followed by a sequencing step (Ng S. B. et al, 2009, Nature 461: 272-6). Numerous technical approaches have been made commercially available for the sequencing of DNA sequences, including pyrosequencing (commercially available as Roche 454), dye sequencing (commercially available through Illumina), digital sequencing (commercially available as IonTorrent sequencing) among others.

While the step of identifying tumor-specific mutations is mandatory, further optional filtering may be used to select optimal neopeptides to be encoded by the personalized recombinant poxvirus and/or to combine them in suitable neopeptide fusions. Indeed, many tumor specific mutations may accumulate during transformation and cancer progression and some may have better potential for stimulating the immune system of the subject to be treated against his cancer. When additional filtering is used, the identification step preferably comprises, in addition to sub-steps a) to d) described above, at least one of the following additional sub-steps e) to i):

e) ranking potential neopeptide(s) by their levels of expression in the tumor (or the levels of expression of the corresponding neoantigens), either at the mRNA transcriptional level, or at the protein translation level;

f) selecting non-self-expressed tumor-specific mutation(s);

g) predicting the immune potential of the neoepitope(s) comprised in the neopeptide(s), either by in silico prediction or by immunogenicity biological tests;

h) predicting the presence of potential TM segment(s) in neoepitopes themselves (intra peptide TM) and/or in neopeptide fusions comprising several neopeptides (inter peptide TM at fusion areas, i.e. areas covering the C-terminus of a first neopeptide and the N-terminus of a second neopeptide, and optionally a linker between the first and second neopeptides);

i) ranking potential neopeptide(s) and/or neopeptide fusion(s) by their degree of hydrophobicity and in particular, selecting neopeptide(s) and/or neopeptide fusion(s) so that said neopeptide(s) and/or neopeptide fusion(s) display(s) a negative global hydrophobicity score and/or a global hydropathy score equal or below 0.1.

As mentioned above, at least one of additional sub-steps e) to i) may be present in the identification step. Several of additional sub-steps e) to i) may be present. In particular, in a preferred embodiment, the identification step further comprises, in addition to sub-steps a) to d) described above, sub-steps e) and f) above (these sub-steps are described in more details below), and optionally also:

sub-step g) (which is also described in more details below),
sub-step h) (which is also described in more details below),
sub-step i) (which is also described in more details below), or
any combination of sub-steps g), h) and i) (e.g. sub-steps g) and h), sub-steps g) and i), sub-steps h) and i), or sub-steps g), h) and i)).

Sub-Step e):

Additional filtering can be added by ranking the neoantigens by their levels of expression in the tumor. Thus, in a preferred embodiment, the identification step further comprises a sub-step e) of selecting the neopeptides that are at least expressed, and preferably highly expressed, in the tumor. The expression may be detected or quantified at the mRNA or protein level. In one embodiment, neopeptides may be selected based on the detection that they are at least transcribed, and preferably highly transcribed in the tumor, i.e. an expressed tumor-specific mutation that is found in the RNA tumor sample and occurs in an ORF (when translated); (RefSeq transcript or Genbank). For illustrative purposes, said expressed tumor-specific mutation(s) is/are typically identified by sequencing the complementary DNA (cDNA) generated from the RNA extracted from said tumor biological sample obtained from the patient, i.e. the transcriptome. As used herein, the transcriptome refers to the full range of messenger RNA (mRNA) expressed by an organism. Techniques for transcriptome sequencing are well known in the art (e.g. Chu and Corey, 2012, Nucleic Acid Ther. 22: 271-4; Wang et al., 2009, Nat Rev Genet. 10(1): 57-63). Preferably, the mRNA encoding the mutated neoantigen is abundantly expressed in the RNA extracted from the tumor sample. While it is not possible to give a preferred absolute value of expression for selection of the neopeptides, the selection is rather relative, potential neopeptides expression being detected/quantified and ranked by order of priority. Those skilled in the art know how to compare expression level of various candidate neopeptides in the tumor of the subject to be treated and rank them by decreasing expression level, highly expressed neopeptides being ranked first, up to non-expressed neopeptides, at the end of the list.

Alternatively to or in combination with mRNA expression, the selection of neopeptides may be performed based on the expression level of the peptide resulting from a tumor-specific mutation using well described proteomic technologies such as western blot, immunoassays, mass spectrometry. Here also, the selection is rather relative, potential neopeptides expression being detected/quantified and ranked by order of priority. This is also easy to those skilled in the art.

Sub-Step f):

Alternatively to or in combination with sub-step e), an additional filtering can also be added by including a step of selecting non-self neopeptides, meaning a neopeptide that is not present as such in the subject proteome. Indeed, while the presence of a tumor-specific mutation ensures that the same peptide is not present in the corresponding wild-type protein expressed in healthy cells of the subject, sub-step f) aims at checking that the same peptide is not part of another protein expressed in healthy cells of the subject. For illustrative purpose, the polypeptide that is identified as being mutated is dissected into a plurality of minimal immune determinants (e.g. 9 mers overlapping by one amino acid) and aligned with blastp (Altschul et al., 1990, J. Mol. Biol. 215(3):403-10) against the host's proteome (e.g. the human proteome for a human subject) corresponding to the proteins that are expressed in the host. Mutated epitopes not shared with host proteins are then selected. In other terms, self-epitopes (i.e. present in the proteome) are eliminated to avoid autoimmunity problems and risk of immune tolerance against a self-peptide that may decrease immune response. As mentioned before, sub-step f) may preferably be combined with sub-step e), thus resulting in the selection of (highly) expressed non-self neopeptides.

Sub-Step g):

Alternatively to or in combination with sub-step e), sub-step f) and the combination of sub-steps e) and f), additional filtering may still be added by predicting the immune potential of the selected neopeptides. Such a selection based on immune potential may be performed either by in silico prediction and/or with bioanalytic approaches (e.g. by immunogenicity biological tests). In silico predictors are built using machine learning algorithms such as artificial neural networks (ANN) or support vector machines (SVM) and trained to identify highly immunogenic sequences. The algorithm is then used to classify epitopes for their affinity for HLA class I and/or class II protein as an index of their potential presentation. For illustrative purposes, this further and optional step may include a step of HLA typing and prediction of the MHC class II binding (dissecting the mutated antigen into a plurality of peptides/epitopes (usually 8-10 mers for class I binding and 10-20 mers for class II binding overlapping by one amino acid) using training algorithm such as seq2HLA (Boegel et al., 2015, Methods Mol Biol 1310: 247-51), NetMHCIIpan (Andreatta et al., 2015, Immunogenetics 67(11-12): 641-50) and IEDB consensus binding prediction. For illustrative purpose, the mutated peptides having a low score are preferably selected. In other terms, such peptides are predicted to have a better MHC class binding score and thus a better probability to generate a T cell response.

Alternatively, or in addition to in silico prediction of immune potential, immunogenic neopeptides may be identified by appropriate bioanalytic tests well known in the art such as mass spectrometry, cytokine release assays (e.g. IFNγ ELIspot in appropriate animal model), MHC class I or class II binding assays to identify MHC restricted mutations, flow cytometry immunofluorescence staining, histochemistry, etc.

As mentioned above, sub-step g) may preferably be combined with sub-step e), sub-step f) or both sub-steps e) and f), more preferably with both sub-steps e) and f), then resulting in the selection of (highly) expressed non-self and immunogenic neopeptides.

Sub-Step h):

Alternatively, to or in combination with sub-step e), sub-step f), or sub-step g) or any combination thereof (e.g. sub-steps e) and f) or sub-steps f) and g) or sub-steps e) and g), or sub-steps e), f) and g), additional filtering may still be added by predicting the presence of a potential TM segment in the selected neopeptides (intra peptide TM) or in the resulting neopeptide fusion(s) (inter peptide TM). As described above, it is preferred that the selected neopeptides as well as the resulting neopeptide fusion(s) do not comprise TM segment to facilitate the generation of the recombinant poxvirus and appropriate presentation of the neoepitopes to the immune system. As mentioned above, several prediction tools can be used to predict the presence of a TM segment in a given peptide, such as TMHMM (Krogh et al., 2001, J. Mol. Biol. 305: 567-80) and DAS (Dense Alignment Surface). In case of prediction of inter peptide TM at the junction of two neopeptides, inversing the neopeptides may be an option to eliminate the presence of TM. Another option may be the addition of an appropriate linker between the 2 neopeptides.

Sub-Step i):

Alternatively to or in combination with sub-step e), sub-step f), sub-step g) or sub-step h) or any combination thereof (e.g. sub-steps e) and f) or sub-steps f) and g) or sub-steps e) and g), sub-steps g) and h) or sub-steps e), f) and g or sub-steps e), f), g) and h), additional filtering may still be added by ranking the neopeptide(s) and/or neopeptide fusion (s) according to their degree of hydrophobicity or hydrophilicity. Indeed, while the neopeptide fusion(s) can tolerate the presence of one or more short stretch(s) of hydrophobic amino acid residues, it is preferred that at least 60% of the selected neopeptides be hydrophilic in nature as described above to ensure that the resulting neopeptide fusion has a global negative hydrophobicity score and/or a global hydropathy score below 0.1. Such a prediction may be performed by conventional methods and algorithms known in the art such as those cited above (e.g. Kyte and Doolittle, 1982, J. Mol. Biol. 157: 105-32 or ExPAsy Prot Scale Protein algorithm).

Generation of the Recombinant Poxvirus

Further to the identification step, the process for preparing a personalized cancer vaccine according to the present invention may comprise a step of generating the recombinant poxvirus. Typically, such a step comprises the generation of a synthetic nucleic acid encoding the selected neopeptide(s) as described herein (e.g. arrangement in one or more fusion(s) optionally with peptide signal, linkers, tag, etc), the generation of the neopeptide-expressing recombinant poxvirus and the manufacturing of said recombinant poxvirus.

Generation of the Synthetic Nucleic Acid Molecule(s)

Nucleic acid molecule(s) is designed to encode the selected neopeptide(s), with a preference for an arrangement in one or more fusion(s), optionally with linkers, tags and peptide signals as described herein. It is preferably generated by chemical synthesis in automatized process (e.g. assembled from overlapping synthetic oligonucleotides or direct synthesis of a synthetic gene).

In certain embodiments, it might be advantageous to optimize the nucleic acid sequence(s) for providing high level expression in a particular subject. Briefly, the nucleic acid molecule(s) can be designed with the goal of improving expression through codon optimization, the non-selection of non-optimal codons for a given host organism and/or elimination of AT- or GC-rich sequence stretches which are expected to negatively influence expression. The sequence TTTTTNT is also avoided as it is a poxvirus early transcription termination signal.

Expression of the Synthetic Nucleic Acid Molecule(s)

In accordance with the present invention, the neopeptides-encoding nucleic acid molecules(s) to be inserted in the genome of the recombinant poxvirus is/are operably linked to suitable regulatory elements. In the context of the invention, the neopeptide-encoding nucleic acid molecules(s) may be arranged in one or more expression cassette(s). Typically, an "expression cassette" comprises a nucleic acid molecule encoding one or more neopeptide(s) under the control of suitable regulatory elements permitting expression in the subject.

As used herein, the term "regulatory elements" refers to any element that allows, contributes or modulates the expression of neopeptide(s), including replication, duplication, transcription, splicing, translation, stability and/or transport process. As used herein, "operably linked" means that the elements being linked are arranged so that they function in concert for their intended purposes.

It will be appreciated by those skilled in the art that the choice of the regulatory elements can depend on such factors as the neopeptides themselves, the poxvirus itself, the subject to be treated, the level of expression desired, etc. The promoter is of special importance. In the context of the invention, it can be constitutive directing expression in many types of cells or specific to certain cells or types of cells (e.g. tumor-specific regulatory sequences) or regulated in response to specific events or exogenous factors (e.g. by temperature, nutrient additive, hormone, etc) or according to the phase of a viral cycle (e.g. late or early). One may also use promoters that are repressed during the production step in response to specific events or exogenous factors, in order to optimize virus production and circumvent potential toxicity of the expressed polypeptide(s). Those skilled in the art will appreciate that, further to the promoter, the regulatory elements may further comprise additional elements for proper initiation, regulation and/or termination of transcription (e.g. polyA transcription termination sequences), mRNA transport, processing and stability, translation (e.g. an initiator Met, tripartite leader sequences, IRES ribosome binding sites, signal peptides, etc.).

Vaccinia virus promoters are particularly adapted for expression in recombinant poxviruses. Representative examples include, without limitation, the vaccinia 7.5K, H5R, 11K7.5 (Erbs et al., 2008, Cancer Gene Ther. 15(1): 18-28), TK, p28, p11, B2R, A35R and K1L promoters, synthetic promoters such as those described in Chakrabarti et al. (1997, Biotechniques 23: 1094-7; Hammond et al, 1997, J. Virol Methods 66: 135-8; and Kumar and Boyle, 1990, Virology 179: 151-8) as well as early/late chimeric promoters.

When the recombinant poxvirus comprises several expression cassettes encoding one or more neopeptide(s), expression may be controlled by the same or distinct regulatory elements (e.g. promoter). Preferably, the recombinant poxvirus comprises one to expression cassette(s), more preferably each for expression of a neopeptide fusion as described herein. A particularly preferred embodiment is directed to a recombinant MVA comprising one to three cassettes, each for expression of a fusion of 1 to 10 neopeptides under the transcriptional control of a vaccinia promoter selected from the group consisting of p11k7.5, pH5R and pB2R.

In an alternative embodiment, if the number of expression cassettes complicates the construction of the recombinant poxvirus (above 3 for example), one may proceed via a system comprising more than a unique recombinant poxvirus, meaning that the personalized cancer vaccine comprises more than one recombinant poxvirus (e.g. 2 or 3) expressing neopeptides.

Insertion of the Neopeptide-Encoding Nucleic Acid Molecule(s) of the Recombinant Poxvirus The nucleic acid molecule(s) or expression cassette(s) encoding the one or more neopeptide(s) for use herein is/are inserted into the genome of a parental poxvirus to generate said recombinant poxvirus. The neopeptide-encoding nucleic acid sequence(s)/expression cassette(s) may be inserted in any location within the poxvirus genome, e.g. within a viral gene, an intergenic region, in a non-essential gene or region or in place of viral sequences. Preference is given to insertion within the poxviral genome in a non-essential locus. Thymidine kinase gene is particularly appropriate for insertion in Copenhagen and Western Reserve vaccinia virus and deletion II or III for insertion in MVA vector (WO97/02355; Meyer et al., 1991, J. Gen. Virol. 72: 1031-8). Preferably, when the poxvirus is MVA, insertion of the neopeptide-encoding nucleic acid molecule(s) or expression cassette(s) is made within MVA's deletion III. When the recombinant poxvirus comprises several cassettes as described above, they may be inserted in the viral genome at the same or distinct location. Preference is given to insertion of all expression cassettes at the same location, especially in TK locus for a recombinant vaccinia virus and in deletion III for a recombinant MVA.

The general conditions for constructing recombinant poxviruses are well known in the art (see for example WO2007/147528; WO2010/130753; WO03/008533; U.S. Pat. Nos. 6,998,252; ,972,597 and 6,440,422). Typically, the nucleic acid molecule(s)/expression cassette(s) to be inserted is/are cloned in a transfer plasmid surrounded by two recombination arms, corresponding to stretches of poxviral sequences homologous (e.g. 90-100% identical) to those present in the parental genome on both sides of the insertion site. The length of the recombination arms may vary within the transfer plasmid. Desirably, each of the recombination arms comprises at least 150 bp, preferably at least 200 bp, more preferably, at least 300 bp, even more preferably from 300 to 600 bp with a specific preference for 350 to 500 bp (e.g. approximately 350 bp or 500 bp) or for 300 to 400 bp of homologous poxvirus sequences. The parental poxvirus may be a wild-type poxvirus or a modified one (e.g. attenuated, tumor-specific, etc.,) as described above in connection with the term "poxvirus". Insertion is then performed by homologous recombination between the stretch of homologous sequences present both in the parental genome and the linearized transfer plasmid, requiring transfection of permissive cells with the linearized transfer plasmid and infection with the parental poxvirus.

In certain embodiments of the process of the present invention, the step of generating the recombinant poxvirus encompasses the use of a parental poxvirus comprising a reporter gene and, notably, a fluorescent reporter gene, cloned at the site of insertion that is selected for the neopeptide-encoding nucleic acid molecule(s)/expression cassette(s). Preferably, the reporter gene is placed under the transcriptional control of a promoter allowing its expression within the permissive cells, e.g. a vaccinia promoter. This embodiment facilitates the selection of the recombinant poxvirus with respect to the parental poxvirus. Representative examples of fluorescent reporters that can be used in the context of the present invention include, without limitation, GFP (Green Fluorescent Protein), eGFP (Enhanced Green Fluorescent Protein), AmCyan 1 fluorescent protein and mCherry. For instance, when relying on mCherry (a monomeric fluorescent protein that originates from a Discosoma mushroom with peak absorption/emission at 587 nm and 610 nm), the recombinant viruses having inserted the neopeptide-encoding nucleic acid molecule(s) or expression cassette(s) in place of the mCherry-encoding sequences, will give rise to white plaques whereas the parental viruses retaining the mCherry expression cassette will give rise to red plaques The selection of the recombinant poxvirus may be by direct visualization (white plaques) or may also be facilitated by sorting means such as FACS after labelling with an APC (Allophycocyanin)-tagged anti-vaccinia virus antibody. A vast number of anti-vaccinia antibodies is available from commercial sources. Usually, one recombinant is obtained for 50 to 100 parental and the whole process from the insertion step to the generation of the recombinant poxvirus takes to 6 weeks.

A preferred embodiment of this invention is directed to a step of generating recombinant poxvirus allowing to increase homologous recombination efficacy by a factor of at least 10 and to decrease the time necessary to generate the recombinant poxvirus by a factor of at least 1.. As in the process described above, the nucleic acid(s) or expression cassette(s) to be inserted into a poxviral genome is/are cloned into a transfer plasmid step surrounded by recombination arms and the parental virus comprises a reporter gene (e.g. a fluorescent reporter) cloned at the site of insertion under the control of a suitable promoter. Preferably, said parental virus is a MVA comprising inserted into deletion III a reporter gene (in particular the mCherry gene) under the control of a poxvirus promoter. However, the step of generating the recombinant poxvirus comprises a further step of cleavage by an endonuclease able to generate at least one double strand break in the reporter (e.g. mCherry) nucleotide sequence but in which said endonuclease does not cleave the poxviral genome. The suitable endonuclease is preferably selected from the group consisting of zinc finger nucleases (ZFNs), transcription activator-like effector nucleases (TALENs), clustered regularly interspaced short palindromic repeats (CRISPR)/Cas9 nucleases and restriction enzymes with unique cleavage within the fluorescent reporter gene. The use of the CRISPR/CAS9 system for virus editing is described in the art (Yuan et al., 2015, J. Virol 89, 5176-9; Yuan et al., 2016, Viruses 8, 72, doi:10.3390) requiring the use of a plasmid encoding a Cas9 without a nuclear localization signal as well as a suitable guide RNA. In this consideration, further to infection with the parental virus, the permissive cells may be transfected with the transfer plasmid, the Cas9-expressing plasmid and one or more plasmid (s) encoding the guide RNA (e.g. mCherry-targeted guide RNA). The selection of recombinant poxvirus is then performed visually (direct isolation of white plaques corresponding to the recombinant whereas colored plaques correspond to the parental and the color depends on the reporter gene) or using conventional sorting means (FACS optionally after a labelling step with appropriate antibodies as described above). With this process, one recombinant is obtained for 1 to 10 parental and the whole process from the insertion step to the generation of the recombinant poxvirus takes approximately 3-4 weeks. In a preferred embodiment, the step of generating the recombinant poxvirus takes at most 4 weeks, preferably at most 3 weeks, with a ratio of recombinant versus parental comprised between 2 (2 for 1) to 0.1 (1 for 10), preferably between 2 (2 for 1) to 0.05 (1 for 20). In specific embodiments, the ratio recombinant/parental is 1 or above 1, especially when the two recombination arms are approximately 350 bp long.

A particularly preferred embodiment is directed to a process permitting the generation of a recombinant poxvirus (e.g. vaccinia virus, and more preferably MVA) comprising one to three expression cassettes inserted within the vaccinia TK locus or the MVA deletion III, each encoding a fusion of 3 to 10 neopeptides placed under the transcriptional control of a vaccinia promoter selected from the group consisting of p11k7., p7.K, pHR and pB2R, preferably from the group consisting of p11k7., pHR and pB2R (preferably each fusion is under the transcriptional control of a distinct promoter). The present invention also relates to a personalized cancer vaccine comprising such a recombinant poxvirus.

Manufacturing of the Recombinant Poxvirus

Once generated, the recombinant poxvirus for use herein may be produced/amplified using conventional techniques. Therefore, the process of the present invention may further, comprise a step of manufacturing said recombinant poxvirus. In a preferred embodiment, said manufacturing step comprises an amplification step in a suitable producer cell to a suitable scale, a step of recovery of the produced recombinant poxvirus from the cell culture and an optional step of purification of the recovered recombinant poxvirus.

The amplification step includes cultivation of a producer (e.g. permissive) host cell, the infection of the cultured producer host cells, and cultivation of the infected host cell under suitable conditions so as to allow the production of the recombinant poxvirus (e.g. infectious viral particles).

The choice of the producer cell depends on the type of recombinant poxvirus to be amplified. MVA is strictly host-restricted and is typically amplified on avian cells, either primary avian cells (such as chicken embryo fibroblasts (CEF) prepared from chicken embryos obtained from fertilized eggs) or immortalized avian cell lines. Representative examples of suitable avian cell lines for MVA production include without limitation the *Cairina moschata* cell lines immortalized with a duck TERT gene (see e.g. WO2007/077256, WO2009/004016, WO2010/130756 and WO2012/001075); avian cell lines immortalized with a combination of viral and/or cellular genes (see e.g. WO2005/042728); spontaneously immortalized cells (e.g. the chicken DF1 cell line disclosed in U.S. Pat. No. ,879, 924); or immortalized cells which derive from embryonic cells by progressive severance from growth factors and feeder layer (e.g. Ebx chicken cell lines disclosed in WO2005/007840 and WO2008/129058 such as Eb66 described in Olivier et al., 2010, mAbs 2(4): 405-15).

For other vaccinia virus or other poxvirus strains, in addition to avian primary cells (such as CEF) and avian cell lines, many other non-avian cell lines are available for production, including human cell lines such as HeLa (ATCC-CRM-CCL-2™ or ATCC-CCL-2.2™) MRC-, HEK-293; hamster cell lines such as BHK-21 (ATCC CCL-10), and Vero cells. In a preferred embodiment, non-MVA vaccinia virus are amplified in HeLa cells (see e.g. WO2010/130753).

Producer cells are preferably cultured in a medium free of animal- or human-derived products, using a chemically defined medium with no product of animal or human origin. In particular, while growth factors may be present, they are preferably recombinantly produced and not purified from animal material. An appropriate animal-free medium may be easily selected by those skilled in the art depending on selected producer cells. Such media are commercially available. In particular, when CEFs are used as producer cells, they may be cultivated in VP-SFM cell culture medium (Invitrogen). Producer cells are preferably cultivated at a temperature comprised between 30° C. and 38° C. (more preferably at around 37° C.) for between 1 and 8 days (preferably for 1 to days for CEF and 2 to 7 days for immortalized cells) before infection. If needed, several passages of 1 to 8 days may be made in order to increase the total number of cells. For example, after isolation of a white plaque, amplification of the recombinant neoepitope-expressing poxvirus (e.g. MVA) can be carried out first in 6 to 12 well cell culture plaques before being transferred in flasks to obtain the desired virus quantity.

Infection of producer cells by the recombinant poxvirus is made under appropriate conditions (in particular using an appropriate multiplicity of infection (MOI)) to permit productive infection of producer cells. Suitable MOI to be used for amplifying poxviruses are typically between 0.001 and 1 (more preferably about 0.05). Infection step is also preferably performed in a medium (which may be the same as or different from the medium used for culture of producer cells) free from animal- or human-derived products, using a chemically defined medium with no product of animal or human origin. The infection step usually lasts between one and six days, more preferably between two and four days and most preferably about 72 hours.

The infected producer cells are then cultured under appropriate conditions well known to those skilled in the art until progeny viral vector (e.g. infectious virus particles) is produced. Culture of infected producer cells is also preferably performed in a medium (which may be the same as or different from the medium used for culture of producer cells and/or for infection step) free of animal- or human-derived products (using a chemically defined medium with no product of animal or human origin) at a temperature between 30° C. and 37° C., for 1 to days.

The poxviral particles can be collected from the culture supernatant and/or the producer cells. The cell culture supernatant and the producer cells can be pooled or collected separately Recovery from producer cells (and optionally also from culture supernatant) may require a step allowing the disruption of the producer cell membrane to allow the liberation of the vector. Various techniques are available to those skilled in the art, including but not limited to: freeze/thaw, hypotonic lysis, sonication, microfluidization, or high-speed homogenization. According to a preferred embodiment, the step of recovery the produced recombinant poxvirus comprises a lysis step wherein the producer cell membrane is disrupted, preferably by using a high-speed homogenizer. High speed homogenizers are commercially available from Silverson Machines Inc (East Longmeadow, USA) or Ika-Labotechnik (Staufen, Germany). According to particularly preferred embodiment, said High Speed homogeneizer is a SILVERSON L4R.

The poxviral particles may then be further purified, using purification steps well known in the art. Various purification steps can be envisaged, including clarification, enzymatic treatment (e.g. endonuclease, protease, etc), chromatographic and filtration steps. Appropriate methods are described in the art (e.g. WO2007/147528; WO2008/138533, WO2009/100521, WO2010/130753, WO2013/022764). In a preferred embodiment, the purification step comprises a tangential flow filtration (TFF) step that can be used to separate the virus from other biomolecules, to concentrate and/or desalt the virus suspension. Various TFF systems and devices are available in the art depending on the volume to be filtered including, without limitation, Spectrumlabs, Pall Corp, PendoTech and New Pellicon among others.

In a preferred embodiment, said manufacturing step reaches the production of at least $10^9$ pfu, desirably at least $\times 10^9$ pfu and preferably approximately $10^{10}$ pfu or more for a personalized cancer vaccine to be distributed in suitable doses for testing and treatment of the patient (from which originates the tumor sample).

Armed Recombinant Poxviruses

Certain embodiments of this invention also encompass recombinant poxviruses which, further to the neopeptides-encoding nucleic acid molecule(s), comprise additional therapeutic gene(s) inserted in the viral genome, e.g. for enhancing the anti-tumor response. A vast number of therapeutic genes may be envisaged, especially those encoding polypeptides capable of potentiating anti-tumor efficacy of the virus or reinforcing the host's immunity. They can be of human origin or not (e.g. of bacterial, yeast or viral origin) and be a native gene, a fragment or a functional analogue thereof (obtained from the latter by mutation, deletion, substitution and/or addition of one or more nucleotides). Such an analogue preferably has a nucleotide sequence having a degree of identity of at least 70%, advantageously of at least 80%, preferably of at least 90%, and most preferably of at least 95% with the nucleic acid sequence of the native gene. Preferred therapeutic genes are selected from the group consisting of suicide and immunostimulatory genes.

Immunostimulatory Therapeutic Genes

Immunostimulatory therapeutic genes encode polypeptides able to stimulate the immune system or effector cells, in a specific or no-specific way. Examples of suitable immunostimulatory proteins in the context of the invention include without limitation cytokines, with a specific preference for interleukins (e.g. IL-2, IL-6, IL-12, IL-15, IL-24), chemokines (e.g. CXCL10, CXCL9, CXCL11), interferons (e.g. IFNγ, IFNalpha), tumor necrosis factor (TNF), colony-stimulating factors (e.g. GM-CSF, G-CSF, M-CSF . . . ), APC (for Antigen Presenting Cell)-exposed proteins (e.g. B7.1, B7.2 and the like), growth factors (Transforming Growth Factor TGF, Fibroblast Growth Factor FGF, Vascular Endothelial Growth Factors VEGF, and the like), major histocompatibility complex (MHC) components of class I or II, apoptosis inducers or inhibitors (e.g. Bax, Bcl2, BclX . . . ), cytostatic agents (p21, p16, Rb . . . ), immunotoxins, blockers of immune escape mechanisms such as immune checkpoint inhibitors (said inhibitor can be blocking peptides, antibodies or related biological species such as single domain antibodies or antibody fragments), cGAS and the like.

Suicide Genes

The term "suicide gene" refers to a gene coding for a protein able to convert a drug precursor into a cytoxic drug. Representative examples of suitable suicide genes include but, are not limited to, thymidine kinase (TK), thymidylate kinase, cytosine deaminase (CDase) and uracil phosphoribosyl transferase (UPRTase).

CDase and UPRTase are present in prokaryotes and lower eukaryotes (but not in mammals). CDase is involved in the pyrimidine metabolic pathway by which exogenous cytosine is transformed into uracil by means of a hydrolytic deamination. CDase also deaminates an analogue of cytosine, i.e. -fluorocytosine (-FC) prodrug, thereby forming -fluorouracil (-FU), a compound which is highly cytotoxic when it is converted by UPRTase into -fluoro-UMP (-FUMP). The gene sequences and encoded enzymes are publicly available, e.g. in specialized data banks (SWISSPROT EMBL, Genbank, Medline and the like). Particularly preferred are the yeast UPRTase and CDase, in particular those encoded by the *Saccharomyces. cerevisiae* (FUR1 gene; Kern et al., 1990, Gene 88: 149-57). Of particular interest is the FCU1 suicide gene encoding a fusion of *S. cerevisia* CDase and a truncated UPRTase deleted of its 35 first residues (FCY1::FUR1[Delta] 105 fusion) which amino acid sequence is described in the sequence identifier SEQ ID NO: 1 of WO2009/065546).

The therapeutic gene for use herein can independently be generated by a number of ways known to those skilled in the art (e.g. cloning, PCR amplification, DNA shuffling, chemical synthesis) and from any available source (e.g. biologic materials described in the art such as cDNA, genomic libraries, viral genomes or any prior art vector known to include it) using sequence data available to the skilled person and the sequence information provided herein, and then suitably inserted in the recombinant poxvirus either at the same location as the neoepitope-encoding nucleic acid molecule(s) (e.g. in deletion III of MVA) or at another location by conventional molecular biology techniques.

Pharmaceutical Composition

In one embodiment, the personalized cancer vaccine of the present invention is in the form of a composition comprising a therapeutically effective amount of the recombinant poxvirus described herein (or obtained accordingly to the process described herein) and a pharmaceutically acceptable vehicle.

The term "pharmaceutically acceptable vehicle" is intended to include any and all carriers, solvents, diluents, excipients, adjuvants, dispersion media, coatings, antibacterial and antifungal agents, absorption agents and the like compatible with administration in mammals and in particular human subjects.

A "therapeutically effective amount" corresponds to the amount of the recombinant poxvirus required to produce in a subject treated in accordance with the present invention an observable improvement of his clinical status including at least one of those mentioned hereinafter.

Such a therapeutically effective amount may vary depending upon a variety of factors, including but not limited to the characteristics of the poxvirus (including type of virus, bioavailability and doses), the severity and the course of the disease (cancer grade for example), the subject himself (including age, sex, clinical history, general physical condition, etc.), the nature of the pharmaceutically acceptable carrier or excipient in the virus formulation, and the treatment modalities (route of administration, frequency of administration, type of concurrent medication, etc.,). The appropriate dosage of poxvirus may be routinely determined and adapted by a practitioner in the light of the relevant circumstances, for example by monitoring a subject's response to administration of the virus and adjusting the dosage accordingly (for additional guidance, see Remington; The Science and Practice of Pharmacy; Gennaro ed., Pharmaceutical Press, London, UK; e.g. 22nd Edition or subsequent ones).

For illustrative purposes, a suitable therapeutically effective amount for individual doses may vary from approximately $10^5$ to approximately $10^{13}$ vp (viral particles), iu (infectious unit) or pfu (plaque-forming units) depending on the poxvirus and the quantitative technique used. As a general guidance, individual doses from approximately $10^6$ pfu to approximately $10^{11}$ pfu are particularly appropriate in the context of the present invention, more preferably from approximately $10^7$ pfu to approximately $5 \times 10^9$ pfu; even more preferably doses of approximately $5 \times 10^7$ pfu to approximately $10^9$ pfu (e.g. from $5 \times 10^7$ to $6 \times 10^8$, from $6 \times 10^7$ to $5 \times 10^8$, from $7 \times 10^7$ to $4 \times 10^8$, from $8 \times 10^7$ to $3 \times 10^8$, from $9 \times 10^7$ to $2 \times 10^8$ pfu) are convenient for human use, with a preference for individual doses comprising approximately $10^3$ of recombinant poxvirus. Individual doses may be reduced by a factor of 2 to 20 for local administration(s) such as intratumoral injection. The quantity of virus present in a sample can be determined by routine titration techniques, e.g. by counting the number of plaques following infection of permissive cells (e.g. BHK-21 or CEF), immunostaining (e.g. using anti-virus antibodies; Caroll et al., 1997, Virology 238: 198-211), by measuring the A260 absorbance (vp titers), by quantitative immunofluorescence (iu titers) or by qPCR using specific viral primers and probes.

Various formulations can be envisaged in the context of the invention, either liquid or freeze-dried to ensure virus stability under the conditions of manufacture and long-term storage (i.e. for at least 6 months) at freezing (e.g. −70° C., −20° C.), refrigerated (e.g. 4° C.) or ambient (e.g. 20-25° C.) temperature. The recombinant poxvirus is advantageously placed in a diluent appropriate for human or animal use. Representative examples of suitable diluent include sterile water, physiological saline (e.g. sodium chloride), Ringer's solution, glucose, trehalose or saccharose solutions, Hank's solution, and other aqueous physiologically balanced salt solutions.

Desirably, the personalized cancer vaccine composition is suitably buffered for human use. Buffers such as TRIS (tris(hydroxymethyl)methylamine), TRIS-HCl (tris(hydroxymethyl)methylamine-HCl), HEPES (4-2-hydroxyethyl-1-piperazineethanesulfonic acid), phosphate buffer (e.g. PBS; mixture of $Na_2HPO_4$ and $KH_2PO_4$; mixture of $Na_2HPO_4$ and $NaH_2PO_4$), TEA (triethanolamine), EPPS (N-(2-Hydroxyethyl)-piperazine-N'-3-propanesulfonic acid), TRICINE (N-[Tris(hydroxymethyl)-methyl]-glycine) and bicarbonate buffers are particularly appropriate for maintaining a physiological or slightly basic pH (e.g. from approximately pH 7 to approximately pH 9). The buffer (e.g. TRIS-HCl) is preferably present at a concentration of 10 to 50 mM.

It might be beneficial to also include a monovalent salt so as to ensure an appropriate osmotic pressure. Said monovalent salt may notably be selected from NaCl and KCl, preferably said monovalent salt is NaCl, notably in a concentration of 10 to 500 mM.

If needed, the cancer vaccine composition may also include a cryoprotectant so as to facilitate storage at low temperature. Suitable cryoprotectants include without limitation sucrose, trehalose, maltose, lactose, mannitol, sorbitol and glycerol, for example at a concentration varying from 0.5 to 20% (weight in g/volume in L, referred to as w/v) and preferably from 5 to 15% (w/v), with a preference for about 10%. The presence of high molecular weight polymers such as dextran or polyvinylpyrrolidone (PVP) is particularly suited for lyophilized formulations to protect the recombinant poxvirus during the vacuum drying and freeze-drying steps (see e.g., WO03/053463; WO2006/0850082; WO2007/056847; WO2008/114021, WO2014/053571).

For illustrative purpose, buffered formulations including NaCl and/or sugar are particularly adapted to the preservation of poxviruses (e.g. Tris 10 mM pH 8 with saccharose 5% (W/V), Sodium glutamate 10 mM, and NaCl 50 mM; or phosphate-buffered saline with glycerol (10%) and NaCl).

Therapeutic Uses and Method of Treatment

The personalized cancer vaccine and process of the present invention are particularly suited for the treatment of cancers and, notably, metastatic ones and those with high risk of relapse. Therefore, the present invention also provides the personalized cancer vaccine (e.g. the poxvirus composition) for use for treating a cancer or preventing its relapse in a subject as well as the use of the personalized cancer vaccine for such therapeutic purposes. The present invention also relates to the personalized cancer vaccine or composition thereof described herein for the manufacture of a medicament for treating a cancer or preventing its relapse.

In another aspect, the present invention also relates to a method of treatment comprising administering the personalized cancer vaccine composition in a subject in need thereof in an amount sufficient for treating a cancer or preventing its relapse in said subject.

Representative examples of cancers that may be treated in the context of the present invention include bone cancer, liver cancer, pancreatic cancer, stomach cancer, colon cancer, cancer of the esophagus, oro-pharyngeal cancer, lung cancer, cancer of the head or neck, skin cancer, melanoma, uterine cancer, cervix cancer, ovarian cancer, breast cancer, rectal cancer, cancer of the anal region, prostate cancer, lymphoma, cancer of the endocrine system, cancer of the thyroid gland, sarcoma of soft tissue, chronic or acute leukemias, cancer of the bladder, renal cancer, neoplasm of the central nervous system (CNS), glioma, etc. The present invention is particularly appropriate for the treatment of solid tumors. It is also particularly useful for treatment of advanced cancers, including metastatic solid cancers or cancers associated with high risk of relapse. Preferred cancers for being treated according to the modalities described herein include brain cancer, such as for example astrocytomas, embryonal tumors, germ cell tumors, central nervous system atypical teratoid/rhabdoid tumor, craniopharyngioma, ependymoma, glioma and glioblastoma as well as head and neck cancer. Other type of cancers for being treated according to the modalities described herein are lung cancers, and particularly NSCLC with a specific preference for adenocarcinoma, squamous cell carcinoma and large cell carcinoma. Another suitable cancer to be treated with the personalized cancer vaccine of the invention is ovarian cancer.

The beneficial effects provided by the use of or method using the personalized cancer vaccine of the present invention can be evidenced by an observable improvement of the clinical status over the baseline status or over the expected status if not treated according to the modalities described herein. An improvement of the clinical status can be easily assessed by any relevant clinical measurement typically used by physicians or other skilled healthcare staff. In the context of the invention, the therapeutic benefit can be transient (for one or a couple of months after cessation of administration) or sustained (for several months or years). As the natural course of clinical status which may vary considerably from a subject to another, it is not required that the therapeutic benefit be observed in each subject treated but in a significant number of subjects (e.g. statistically significant differences between two groups can be determined by any statistical test known in the art, such as a Tukey parametric test, the Kruskal-Wallis test the U test according to Mann and Whitney, the Student's t-test, the Wilcoxon test, etc).

In particular embodiments, such therapeutic benefits can be correlated with one or more of the followings: inhibiting or slowing tumor growth, proliferation and metastasis, preventing or delaying tumor invasion (spread of tumor cells in neighboring tissues), reducing the tumor lesion number; reducing the tumor size, reducing the number or extent of metastases, providing a prolonged overall survival rate (OS), increasing progression free survival (PFS), increasing the length of remission, stabilizing (i.e. not worsening) the state of disease, preventing the recurrence of disease, providing a better response to another treatment and in particular another immunotherapy, improving quality of life and/or inducing an anti-tumor response (e.g. non-specific (innate) and/or specific such as a cytotoxic T cell response) in the subject treated in accordance with the present invention.

Appropriate measurements are performed routinely in medical laboratories and hospitals available to assess a clinical benefit such as blood tests, analysis of biological fluids and biopsies as well as medical imaging techniques and a large number of kits are available commercially. They can be performed before the administration (baseline) and at various time points during treatment and after cessation of the treatment.

Administration of the Personalized Cancer Vaccine or Composition Thereof

Any of the conventional administration routes are applicable with a preference for parenteral routes. Parenteral routes are intended for administration as an injection or infusion and encompass systemic as well as local routes. Particularly suitable administration routes include, without limitation, intravenous (into a vein), intravascular (into a blood vessel), intra-arterial (into an artery), intradermal (into the dermis), subcutaneous (under the skin), intramuscular (into muscle), intraperitoneal (into the peritoneum), intracerebral (into the brain) and intratumoral (into a tumor or its close vicinity) routes as well as scarification. Infusions typically are given by intravenous route or intratumoral (in a large tumor). Mucosal administrations are also contemplated by the present invention and include, without limitation, oral/alimentary, intranasal, intratracheal, nasopharyngeal, intrapulmonary, intravaginal or intra-rectal route. Topical administrations applied directly to the skin or the surface of tissues (e.g. eye drops; ear drops, etc.,). Inhalation may also be envisaged especially when the tumor to be treated is in the respiratory tract and lungs. The personalized cancer vaccine or composition thereof is preferably administered to the patient by intravenous, subcutaneous, intramuscular or intratumoral injections.

Administrations may use standard needles and syringes or any device available in the art capable of facilitating or improving delivery including for example catheters, electric syringe, Quadrafuse injection needles, needle-free injection devices (e.g. Biojector TM device), infusion pumps, sprays etc. Electroporation may also be implemented to facilitate intramuscular administration. Topical administration can also be performed using transdermal means (e.g. patch, microneedles and the like).

The personalized cancer vaccine can be administered in a single dose or more desirably in multiple doses over an extended period of time. In the context of the present invention, it is possible to proceed via sequential cycles of administrations that are repeated after a rest period. Intervals between each virus administration can be from several hours to 6 months (e.g. 24 h, 48 h, 72 h, a week, 2 weeks, 3 weeks, a month, 2 months, etc.,). Intervals can also be regular or not. The doses may vary for each administration within the range described above. For illustrative purpose, a preferred therapeutic scheme involves one to 10 (e.g. 2, 3, 4, 5, 6, 7, 8, 9, 10) administrations of $10^7$ to $5 \times 10^9$ pfu of a recombinant MVA at approximately 1 or 2 weeks interval until a clinical benefit is observed and every 1 to 6 months after.

Combination Therapies

In further embodiments of the method and therapeutic uses described herein, the personalized cancer vaccine may be administered in conjunction with one or more additional anti-cancer therapy/ies which have utility in the treatment of the aforementioned cancers. In particular, the additional anticancer therapy/ies is/are selected from the group consisting of surgery, radiotherapy, chemotherapy, cryotherapy, hormonal therapy, toxin therapy, immunotherapy and cytokine therapy. Such additional anticancer therapy/ies is/are administered to the subject in accordance with standard practice before, after, essentially simultaneously or in an interspersed manner with the personalized cancer vaccine of the present invention.

In specific embodiments, the method or use according to the invention may be carried out in conjunction with surgery. For example, the personalized cancer vaccine may be administered after partial or total surgical resection of the tumor (e.g. by local application within the excised zone, for example).

In other embodiments, the method according to the invention can be used in association with radiotherapy. Those skilled in the art can readily formulate appropriate radiation therapy protocols and parameters (see for example Perez and Brady, 1992, Principles and Practice of Radiation Oncology, 2nd Ed. JB Lippincott Co; using appropriate adaptations and modifications as will be readily apparent to those skilled in the field). The types of radiation that may be used in cancer treatment are well known in the art and include electron beams, high-energy photons from a linear accelerator or from radioactive sources such as cobalt or cesium, protons, and neutrons. Dosage ranges for radioisotopes vary widely, and depend on the half-life of the isotope, the strength and type of radiation emitted, and the uptake by the neoplastic cells. Regular X-rays doses for prolonged periods of time (3 to 6 weeks), or high single doses are contemplated by the present invention.

In certain embodiments of the invention, the personalized cancer vaccine may be used in conjunction with chemotherapy currently available for treating cancer. Representative examples of suitable chemotherapy agents include, without limitation, alkylating agents, topoisomerase I inhibitors, topoisomerase II inhibitors, parp inhibitors, platinum derivatives, inhibitors of tyrosine kinase receptors, cyclophosphamides, antimetabolites, DNA damaging agents and antimitotic agents.

In further embodiments, the personalized cancer vaccine may be used in conjunction with immunotherapeutics such as anti-neoplastic antibodies as well as siRNA and antisense polynucleotides. Representative examples include among others monoclonal antibodies blocking specific immune checkpoints such as anti-PD-1, anti-PD-L1, anti-CTLA-4, anti-LAG3, etc (e.g. Ipilimumab, tremelimumab pembrolizumab, nivolumab, pidilizumab, AMP-224MEDI4736, MPDL3280A, BMS-936559, etc.,), monoclonal antibodies blocking Epidermal Growth Factor Receptor (in particular cetuximab, panitumumab, zalutumumab, nimotuzumab, matuzumab, trastuzumab (Herceptin™), etc.,) and monoclonal antibodies blocking Vascular Endothelial Growth Factor (in particular bevacizumab and ranibizumab).

In additional embodiments, the personalized cancer vaccine may be used in conjunction with adjuvant. Representative examples of suitable adjuvants include, without limitation, TLR3 ligands (Claudepierre et al., 2014, J. Virol. 88(10): 5242-55), TLR9 ligands (e.g. CpGs such as ODN1826 (Fend et al., 2014, Cancer Immunol. Res. 2, 1163-74) and Litenimod (Li28) (Carpentier et al., 2003, Frontiers in Bioscience 8, e115-127; Carpentier et al., 2006, Neuro-Oncology 8(1): 60-6; EP 1 162 982; U.S. Pat. Nos. 7,700,569 and 7,108,844) and PDE5 inhibitors such as sildenafil (U.S. Pat. Nos. 5,250,534, 6,469,012 and EP 463 756).

In a preferred embodiment, the method of the invention increases survival time in the treated subject as compared to without treatment, e.g. by at least 3 months. Alternatively, the method of the invention generates a T cell response against said tumor (CD4+ and/or CD8+ T cell response).

The administrations of the personalized cancer vaccine and the one or more additional anti-cancer therapy may be in intervals, ranging from minutes to weeks. For example, one may provide the subject with the recombinant poxvirus and the additional anti-cancer therapy sequentially or in an interspersed way but concomitant administrations of both therapies within the same period of time are also contemplated. The course of treatment may be routinely determined by a practitioner and various protocols are encompassed by the present invention. For example, 1 to 10 administrations of the personalized cancer vaccine may be carried out after surgery and chimio/radiotherapy. Moreover, after a course of treatment, it is contemplated that there is a period of time during which no anti-cancer treatment is administered before repetition of treatment cycle(s).

All of the above cited disclosures of patents, publications and database entries are specifically incorporated herein by reference in their entirety. Other features, objects, and advantages of the invention will be apparent from the description and drawings and from the claims. The following examples are incorporated to demonstrate preferred embodiments of the invention. However, in light of the present disclosure, those skilled in the art should appreciate that changes can be made in the specific embodiments that are disclosed without departing from the spirit and scope of the invention.

EXAMPLES

Materials and Methods

The constructions described below are carried out according to the general genetic engineered and molecular cloning techniques detailed in Maniatis et al. (1989, Laboratory Manual, Cold Spring Harbor Laboratory Press, Cold Spring Harbor NY or subsequent editions) or according to the manufacturer's recommendations when a commercial kit is used. PCR amplification techniques are known to the person skilled in the art (see for example PCR protocols—A guide to methods and applications, 1990, published by Innis, Gelfand, Sninsky and White, Academic Press).

Generation of Recombinant MVA

Vaccinia promoters and synthetic genes coding for the different fusions of neoepitopes were synthesized by Geneart (Regensburg, Germany). The sequences were optimized for human codon usage and a Kozak sequence (ACC) was added before the ATG starting codon. Moreover, some motives were excluded: TTTTTNT, GGGGG, CCCCC which are deleterious for expression in poxvirus vector.

Generation of Multiepitope Constructs: MVATG19022 and MVATG19023

MVATG19022 contains an expression cassette encoding for a fusion of 5 peptides originating from five different antigens: FCU1, b-gal, MUC1, HPV-16 E7 and HPV-16 E1. All peptides are 27 mers comprising a C57bl/6 T cell epitope. More specifically, the pentatope fusion comprises from 5' to 3' a FCU1 peptide (SEQ ID NO: 1), a b-Gal peptide (SEQ ID NO: 2), a HPV-16 E1 peptide (SEQ ID NO: 3), a HPV-16 E7 peptide (SEQ ID NO: 4) and a MUC1 peptide (SEQ ID NO: 5) with 10 mer GS linkers present at the N-terminus of the fusion, between the peptides and after the last peptide for optimal processing of the fusion polypeptide and epitope presentation. In order to facilitate detection, a tag sequence was added at the C-terminus of the fusion, Flag tag (DYKDDDDK; SEQ ID NO: 6). The pentatope fusion (SEQ ID NO: 7) was placed under the control of p11K7.5 promoter (SEQ ID NO: 8).

MVATG19023 contains an expression cassette encoding for the same pentatope fusion in which a signal peptide obtained from the rabies glycoprotein (SEQ ID NO: 9) was added at the N-terminus. The modified pentatope fusion (SEQ ID NO: 10) was placed under the control of p11K7.5 promoter (SEQ ID NO: 8).

DNA fragments corresponding to each of the pentatope fusion and surrounded by around 30 bp of sequences homologous to the vaccinia transfer plasmid were generated by synthetic way. The GeneArt® Strings™ DNA fragments were inserted by In-Fusion cloning (In-Fusion HD cloning kit, Clontech) in the vaccinia transfer plasmid pTG18626 digested by NotI and BgllII, resulting respectively in pTG19022 and pTG19023.

The MVA transfer plasmid, pTG18626, is designed to permit insertion of the nucleotide sequence to be transferred by homologous recombination in deletion III of the MVA genome. It originates from the plasmid pUC18 into which were cloned the flanking sequences (BRG3 and BRD3) surrounding the MVA deletion III (Sutter and Moss, 1992, Proc. Natl. Acad. Sci. USA 89:10847).

The homologous recombination was performed using a parental MVA containing gene encoding for the mCherry fluorescent protein into its deletion III (MVA mCherry). The advantage of MVA mCherry is to differentiate cells that are infected by the recombinant virus which have successfully integrated the expression cassette from the ones that are infected by the initial starting MVA mCherry virus (parental virus). Indeed, mCherry gene is removed in case of successful recombination of the expression cassette within deletion III and the viral plaques appear as white.

Although recombination is a relatively frequent event in vaccinia virus only 1-5% of the recombinant plaques contain the inserted DNA. Therefore, in order to increase the efficacy of homologous recombination a further step of cleavage by an endonuclease was added. For example, the CRISPR-CAS9 system may be used to specifically generate double-strand breaks in the mCherry gene in MVA, and, thus, to increase the efficiency of selection of recombinant MVA (e.g. usually 10-50% of the viral plaques contain the expression cassette). Given that MVA replicates in the cytoplasm, it is recommended to provide the Cas9 enzyme without NLS (nuclear localization signal) (pCas9 plasmid) as described in Yuan et al. (2015, J. Virol. doi:10.1128), together with pgRNA containing a gRNA specific to mCherry sequence.

Generation of MVATG19022 was performed by homologous recombination in primary chicken embryos fibroblasts (CEF). CEF were isolated from 11 or 12 day-old embryonated SPF eggs (Charles River) and were cultivated in culture medium supplemented with Glutamine 4 mM and containing gentamycin at a final concentration of 40 mg/L. CEF were cultivated at 37° C., 5% $CO_2$ for 24 or 48 h before MVA infection. $10^8$ CEF cells were infected at MOI 0.02 with the parental mCherry-encoding MVA for 2 hours in another culture medium supplemented with 2 mM L-glutamine and containing gentamycin at a final concentration of 40 mg/L. Infected cells were trypsinized and $10^7$ cells were transfected by nucleofection with 2 µg of pTG19022, (according to Amaxa Nucelofector technology) and, if needed, with pCAS9 and pgRNA. The transfected cells were transferred in a 6-well plate and incubated for 2 days at 37° C. Infected and transfected cells were harvested and used for plaque isolation. Serial dilutions were used to infect CEF monolayers during 30 minutes at room temperature. $2 \times 10^7$ cells CEF platted in 60 mm culture dishes were infected with 500 µL of each dilution. After 30 minutes, a layer of 5 mL of culture medium containing 1% agarose was overlaid on monolayer cells. Culture dishes were subsequently incubated at 37° C. in 5% $CO_2$ atmosphere during 96 h. Plaque detection by microscopic examination was facilitated by superposing a new layer (5 mL) of culture medium containing 1% agarose and 0.008% neutral red. Selected white plaques were picked and placed in 500 µL of PBS and frozen at −20° C. Viral amplification was performed by using the frozen plaques to infect CEF monolayer cells during 30 minutes at room temperature in 6-well cell culture plate. After 30 minutes, 2 ml of culture medium were added and the infected cells were incubated at 37° C. in 5% $CO_2$ atmosphere. After 72 h the whole content of the dish was harvested (amplification 1). Optionally, a second step of amplification may be done in F175 flasks. In this case, 100 µL of amplified plaques was diluted in 10 mL of PBS and used to infect fresh CEF in two culture flasks (F175 containing about $7 \times 10^7$ cells), during 30 minutes at room temperature. 20 mL of culture medium were added and infected cells were incubated at 37° C. in 5% $CO_2$ atmosphere during 72 h. The amplification 2 was then harvested. The presence of the expression cassette and absence of contamination by parental MVA was verified by PCR. All this process could be done in only three weeks.

MVATG19022 may also be produced at a larger scale for preclinical experiments using several F500 flasks. CEF are first cultured in a suitable medium supplemented with glutamine 4 mM and containing gentamycin at a final concentration of 40 mg/L and were incubated during 48 h before infection, at 37° C. 5% $CO_2$ Cells were then infected with the amplification 2 bulk as described above. Viral amplification was performed at 37° C. or lower (e.g. 34-35° C.) 5% $CO_2$ for 72 h to 96 h. Infected cells and medium were then pelleted and frozen. The crude harvest was disrupted using High Speed homogeneizer (SILVERSON L4R) and submitted to a purification process (e.g. as described in WO2007/147528). Briefly, the lysed viral preparation can be clarified by filtration, and purified by a tangential flow filtration (TFF) step. Purified virus was resuspended in a suitable virus formulation buffer (e.g. 5% (w/v) Saccharose, 50 mM NaCl, 10 mM Tris/HCl, 10 mM Sodium Glutamate, pH8).

Generation of MVATG19023 virus was performed in CEF by homologous recombination and produced as described above.

Generation of CT26 Neopeptides Constructs: MVATG19030 and MVATG19038

MVATG19030 contains two expression cassettes encoding each a fusion of five CT26 neopeptides (pentatopes) which sequences are described in Kreiter et al. (2015, Nature, 520: 692-6). In order to facilitate detection of pentatope, tag sequences were added at the C-terminus of each pentatope, respectively Flag tag (DYKDDDDK; SEQ ID NO: 6) for pentatope 1 and c-myc tag (EQKLISEEDL; SEQ ID NO:11) for pentatope 2. The tagged pentatope 1 (SEQ ID NO: 12) was placed under the control of p11K7.5 promoter (SEQ ID NO: 8) while the tagged pentatope 2 (SEQ ID NO: 13) was placed under the control of pH5R promoter (SEQ ID NO: 14.).

MVATG19038 contains two expression cassettes encoding for the same pentatope fusions in which the rabies glycoprotein's signal peptide (SEQ ID NO: 9) was added at the N-terminus of pentatope 1 and the measles F glycoprotein's signal peptide (SEQ ID NO: 15) at the N-terminus of pentatope 2. The modified pentatope 1 (SEQ ID NO: 16) was placed under the control of p11K7.5 promoter (SEQ ID NO: 8), while the modified pentatope 2 (SEQ ID NO: 17) was placed under the control of pH5R promoter (SEQ ID NO: 14).

DNA fragments corresponding to the two expression cassettes separated by suitable restrictions sites and surrounded by around 30 bp of sequences homologous to the vaccinia transfer plasmid was generated by synthetic way. After restriction by SnaB1, the fragments were inserted by In-Fusion cloning (In-Fusion HD cloning kit, Clontech) in the vaccinia transfer plasmid pTG18626 digested by NotI and BglII, resulting respectively in pTG19030 and pTG19038.

Generation of MVATG19030 and MVATG19038 viruses were performed in CEF by homologous recombination as described above.

Generation of Human Neopeptide Construct: MVATG19111

MVATG19111 contains three expression cassettes encoding all together eighteen human neopeptides dispatched in three fusions: the first one containing 7 neopeptides (heptatope), the second 6 neopeptides (hexatope) and the third 5 neopeptides (pentatope). Most of the 18 encoded neopeptides were constituted of 29 amino acids with the mutation in central position, except four of them, respectively a 19 amino acid neopeptide having the mutation located at its N-terminus (NP1), a neopeptide containing 21 amino acids with the mutation located at its C-terminus (NP18), a neopeptide containing 26 amino acids having the mutation in the central position as defined herein but with a 3 amino acid deletion in the C-term flanking sequence (NP10) and a neopeptide of 76 amino acids arising from a frameshift mutation (NP15). In each fusion, the neopeptides were separated by a 5-amino acid linker for optimal processing of the fusion polypeptide and epitope presentation. Four different linkers were used: GSGSG, SGSGS, GSTSG and SGTGS. Linker sequence codons were degenerated to avoid repetition and limit recombination events during the poxvirus production process.

In order to facilitate detection of peptide fusions, tag sequences were added at the C-terminus of each fusion, respectively HA tag (YPYDVPDYA; SEQ ID NO: 18) for the heptatope, HSV tag (QPELAPEDPED; SEQ ID NO: 19) for the hexatope and VSV tag (YTDIEMNRLGK; SEQ ID NO:20) for the pentatope. A signal peptide was added at the N-terminus of each neopeptide fusion to enhance the processing through ER. Signal peptides obtained from the rabies glycoprotein (SEQ ID NO: 9) were added at the N-terminus of the heptatope and the pentatope, and one obtained from the measles F glycoprotein (SEQ ID NO: 15) at the N-terminus of the hexatope.

Various promoters were used to control expression of the neopeptide fusions, respectively the pH5R promoter (SEQ ID NO: 14) driving expression of the heptatope, the pB2R promoter (SEQ ID NO: 21) for expression of the hexatope and the p11K7.5 promoter (SEQ ID NO: 8), for the pentatope, DNA fragment corresponding to the three expression cassettes separated by suitable restrictions sites and surrounded by around 350 bp of sequences homologous to the vaccinia transfer plasmid was generated by synthetic way, leading to pTG19111.

Generation of MVATG19111 virus was performed in CEF by homologous recombination as described above.

Generation of Human Neopeptide Construct: pTG19247

A plasmid construct pTG19247 was generated containing three expression cassettes each encoding ten neopeptides. The pool of 30 neopeptides was selected based on their predicted immunogenicity from publicly available patient dataset (study PRJEB3132, Exome sequencing of human lung adenocarcinoma samples and their normal counterparts). For illustrative purpose, the amino acid sequence is given in SEQ ID NO: 60, 61 and 62. Each cassette comprises a signal sequence (obtained from rabies and measles F glycoproteins) and placed under the control of pH5R, pB2R and p11k7.5 promoters, respectively. To facilitate the construction of the fusions, no linkers were included between the selected neopeptides. Generation of the corresponding virus was performed in CEF by homologous recombination according to the process disclosed above. However, a low ratio of white plaques below 5% was obtained and PCR analysis of the white plaques revealed the absence of generation of recombinant MVA carrying the neopeptide fusions (the white plaques likely result from mutation in the mCherry sequence).

Expression of Neopeptides and Western Blot Analysis $4 \times 10^6$ CEF cells were infected at MOI 0.2 with the various MVA encoding for neopeptides fusions in 6-well plates. MVATGN33.1 empty vector was used as a negative control. After 24 hours, medium was discarded and cells were lysed with 300 µL/dish of Tris-Glycin-SDS 2× buffer (ref: LC2676; Novex) containing β-mercaptoethanol (5% V:V). The lysate was then sonicated and heated for 5 min at 95° C. Twenty microliters of cell lysates were submitted to electrophoresis in precasted 4-15% Criterion gel using the Criterion Precast gel system (Biorad). Following electrophoresis, proteins were transferred onto a PVDF membrane (Trans-Blot® Turbo™ Transfer System (#170-4155, Biorad)). Immunodetection was performed using HRP-anti-TAG antibodies. A 1/2000 dilution of each of the following antibody was applied to the membrane: monoclonal anti-FLAG M2, HRP antibody (Sigma, A8592), HA Tag monoclonal antibody, HRP (Thermofisher, 26183-HRP), VSV-G Tag polyclonal antibody, HRP (Thermofisher, PA1-26564), goat polyclonal anti-HSV tag antibody, HRP (Abcam, 19392) while a 1/5000 dilution of monoclonal anti-cMyc, HRP antibody (Novex 46-0709) was used. Immune-complexes were revealed using the Amersham ECL prime Western blotting reagent (GE Healthcare, RPN2236) and analysed using the Molecular Imager ChemiDOC™ XRS from BIO-RAD.

ELISpot Assay

Plate Preparation

Plates (Millipore, MSIPS4W10) were pre-treated 1 minute with Ethanol 35% (15 µl/well) and washed five times with sterile water (200 µl/well). Wells were coated with 100 µl of 15 µg/ml anti-mouse IFNγ antibody (Mabtech, AN18, 3321-3-1000; diluted in PBS) and incubated overnight or over week-end at +4° C. The day of the experiment, plates were washed five times with sterile PBS (200 µL/well) and saturated for at least 1 h at 37° C. with complete medium (CM) 200 µL/well.

Sample Preparation

Ex vivo Elispots were performed with fresh splenic lymphocytes. For each experiment, spleens from 5 animals of each group were collected and pooled. Spleens were collected in 4 mL of complete medium (CM: RPMI 10% FCS or X-Vivo if mice are bearing tumors) and then crushed with a syringe plunger through a 70 µm cell strainer in a 6-well plate. Splenocyte suspension obtained was diluted 2-fold in CM, laid over 4 mL of Lympholyte®-M separation cell media (Cedarlane, ref: CL5035) and centrifuged for 20 minutes at 1500 g at room temperature. The interphase containing lymphocytes was collected and washed twice in 10 mL of RPMI1640 medium (centrifugation 5 minutes at 400 g at room temperature). Lymphocytes were resuspended in 2 mL of RBC lysis buffer (BD PharmLyse, BD BioScience, ref 555899) and incubated for 5 to 15 minutes at room temperature to lyse red blood cells (RBC). After one wash step in CM (centrifugation minutes at 400 g at room temperature) lymphocytes were resuspended in 1 mL of CM and counted using the «Z2 Coulter particle count and size analyzer» of Beckman Coulter. Cell concentration was adjusted to $1 \times 10^7$ cells per mL with CM.

Assay

First, saturating medium was removed by emptying the plates and 50 µL CM was added in all wells. 50 µL of each peptide, or pool of peptide, at 4 µg/mL (i.e. for the pool, the concentration of each peptide was 0.4 µg/mL) in CM or 50 µL of CM (negative control) were added into the relevant wells (according to a previously defined pipetting scheme; each condition was tested in quadriplicate). As positive control, 50 µL of 20 µg/mL of Concanavalin A (ConA) were added. Secondly, 100 µL of each lymphocyte suspension ($1 \times 10^6$ cells) were added into the wells (with the exception of T8V wells where only $3 \times 10^5$ cells were added) and plates were incubated for 18 h to 20 h at 37° C. in 5% $CO_2$.

Cells were removed by emptying the plates, plates were washed 5 times with PBS (200 µL/well) and 100 µL biotinylated anti-mouse IFNγ monoclonal antibody (Mabtech, R4-6A2, 3321-6-1000; 1 µg/mL final concentration in PBS 0.5% FCS) was distributed in all wells. Plates were incubated for 2 hours at room temperature, then washed five times with PBS and Extravidin-Phosphatase alkaline (SIGMA, E236, 1/5000 e in PBS 0.5% FCS) was added in each well (100 µL/well). Plates were incubated 1 h at room temperature, washed five times with PBS and 100 µl of BCIP/NBT substrate solution (BCIP/NBT tablets, SIGMA, B5655; 0.45 µM filtered) were distributed in each well. Plates were incubated at room temperature, in darkness, until distinct spots were seen in positive wells (after about 5 to 10 minutes). Color development was stopped by emptying the plates and extensive washings with tap water. Plates were left in darkness without lid at room temperature, until they dried (at least 1 h).

Data Acquisition

Spots were counted with an ELISpot reader (CTL Immunospot reader, S5UV). A quality control was performed for each well to ensure that the counts provided by the ELISpot reader match with the reality of the picture. Results were expressed for each quadriplicate as the mean number of spot forming units (sfu) per $1 \times 10^6$ splenic lymphocytes. Positivity was determined as described in Moodie et al. (2006, J. Immunol Methods 315: 121-32) and Moodie et al. (2010, Cancer Immunol Immunother doi 10.1007/s00262-010-0875-4).

Example 1: Immunization with a Multipeptide Construct

Vector Construction and Production

As illustrated in FIG. 1, two MVA constructs, MVATG19022 and MVATG19023 were generated for the expression of a fusion of 5 peptides originating from various antigens separated from one another by 10-amino acid GS linkers for optimal processing of the fusion polypeptide and epitope presentation. Each peptide is a 27 mer and comprises a validated C57bl/6 T cell epitope. The pentatope encoding sequence is placed under the control of the p11k7.5 promoter (SEQ ID NO:8) and the cassette inserted into deletion III of the MVA genome. More specifically, the pentatope fusion comprises from 5' to 3' a FCU1-derived peptide (SEQ ID NO:1), a b-Gal-derived peptide (SEQ ID NO:2), a HPV-16 E1-derived peptide (SEQ ID NO:3), a HPV-16 E7-derived peptide (SEQ ID NO:4) and a MUC1-derived peptide (SEQ ID NO:5) with 10mer GS linkers preceding the FCU1 peptide, between the peptides and after the MUC1 peptide. A Flag tag (SEQ ID NO:6) is present at the C-terminus in order to facilitate expression evaluation. Moreover, MVATG19023 distinguishes from MVATG19022 by the presence of a signal peptide at its N-terminus. For illustrative purposes, the pentatope fusion comprises an amino acid sequence as set forth in SEQ ID NO:7 for MVATG19022 and as set forth in SEQ ID NO: 10 for MVATG19023 (with signal peptide).

Evaluation of the Peptide Expression

The expression of the peptide fusion was evaluated by Western blot in CEF infected with each vector using antibodies directed to the tag Flag peptide included in the expression cassette. Briefly, CEF were infected or not (Mock control) at MOI of 0.2 with MVATG19022 or MVATG19023 or with an empty (i.e. non-recombinant) MVA (TGN33.1 as negative control). Cells were harvested after 24 h and cell lysates analyzed by SDS-PAGE. Immunodetection of the expression products was detected with an anti-Flag antibody. The results show that a band was detected corresponding to the expected size for the pentatope fusions directed by MVATG19022 (19.7 kDa) and MVATG19023 (22.2 kDa). As expected no bands were detected in cell lysates obtained from cells infected with the empty MVA or the Mock buffer.

Moreover, higher expression levels were observed when the cassette is equipped with a peptide signal as evidenced by the more intense band obtained with MVATG19023 compared to that detected in cells infected with MVATG19022.

Immunogenicity Evaluation

The capacity of these two pentatope-expressing vectors to generate a T cell response was tested in C57bl/6 mice by ELIspot IFNγ and compared to the responses produced by MVA vectors encoding a full-length antigen, respectively MVATG9931 (MUC-1), MVATG15637 (FCU-1), MVATG18124 (β-Galactosidase), MVATG8042 (HPV-16 E7) and MVATG17409 (HPV-16 E1).

More specifically, MVATG9931 (TG4010 with its clinical name) is a recombinant MVA coding for MUC1 tumor-associated antigen and human interleukin 2 (IL-2). TG4010, in combination with first-line standard of care chemotherapy in advanced metastatic non-small-cell lung cancer (NSCLC), demonstrated efficacy in two different randomized and controlled phase 2b clinical trials (Quoix et al., 2011, The Lancet Oncol 12(12): 1125-33). MVATG15637 is a recombinant MVA encoding the yeast-originated FCU1, expressing yeast CDase and UPRTase enzymes that transform the prodrug fluorocytosine (5-FC) into cytotoxic 5-fluorouracil (5-FU) and -fluorouridine-'-monophosphate (5-FUMP), respectively (Husseini et al., 2017, Ann Oncol 28(1): 169-74). MVATG18124 contains the bacterial LacZ gene encoding the beta-galactosidase antigen under the control of poxvirus promoter pH5R. MVATG8042 (TG4001 with its clinical name) encodes the mutation-inactivated human papilloma virus (HPV) 16 E6 and E7 oncoproteins and human interleukin-2 (WO99/03885). MVATG17409 encodes HPV-16 E1 antigen modified to abolish the replicative function of the native polypeptide (WO2008/092854).

Briefly, five C57bl/6 mice per group were subcutaneously injected twice at one week interval (days 0 and 7) with the corresponding MVA. For each injection, $2,5 \times 10^7$ pfu of MVA (100 μL in the following buffer: Tris 10 mM [tris (hydroxymethyl)aminomethane/HCl], saccharose 5% (W/V), Sodium glutamate 10 mM, Sodium chloride 50 mM, pH 8) were administered in the flank of the animals. One week after the last injection (day 14), all mice were sacrificed by cervical dislocation. Spleens were collected for lymphocyte isolation and IFNγ-producing T cells were quantified by Elispot (cytokine-specific enzyme linked immunospot) assay as described In Material and Methods. Stimulation was performed with the following peptides specific for each expressed antigen/peptide

I8L (HPV16 E1):
(SEQ ID NO: 50)
IAYKYAQL

I8V (b-galactosidase):
(SEQ ID NO: 51)
ICPMYARV

R9F (E7 HPV16):
(SEQ ID NO: 52)
RAHYNIVTF

L15L-3 (MUC1):
(SEQ ID NO: 53)
LSYTNPAVAATSANL
and

EG-15 (FCU-1):
(SEQ ID NO: 54)
EKYHAAFPEVRIVTG

And as controls:

T8V (specific for MVA):
(SEQ ID NO: 55)
TSYKFESV (positive control)

-continued

K9i-3 (RMA, irrelevant):
(SEQ ID NO: 56)
KNGENAQAI

G15H (PyMT, irrelevant):
(SEQ ID NO: 57)
GICLMLFILIKRSRH

As illustrated in FIG. 2A-E, a strong cellular response was detected for 4 out 5 epitopes expressed by MVATG19022 and MVATG19023 (technical background problems hinder interpretation of the MUC-1 response). Except for anti-E1 response, MVATG19023 trends to provide a better response than MVATG19022. One may anticipate that the addressing of the peptide fusion to the endoplasmic reticulum is likely to protect the expressed fusion from degradation by the cellular proteasome and promote its accumulation in the infected cells that are phagocyted by professional antigen presenting cells such as DC.

Figure 2C:
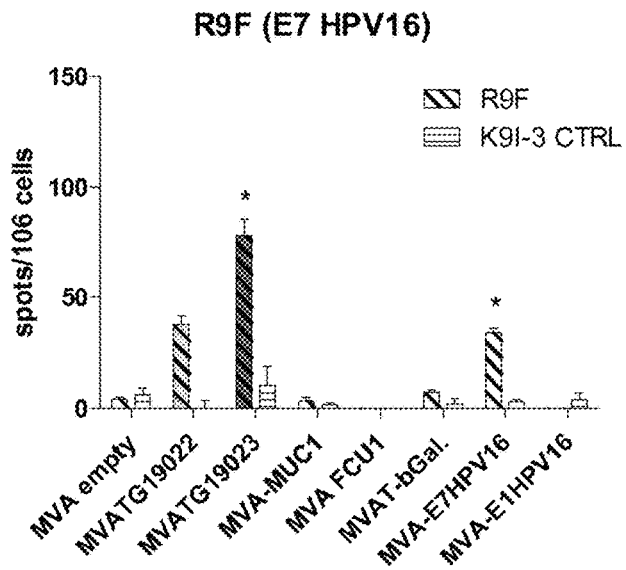
Figure 2D:
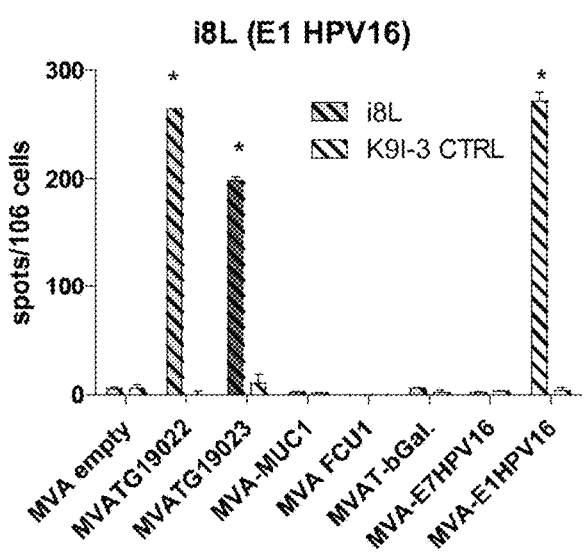
Figure 2E:
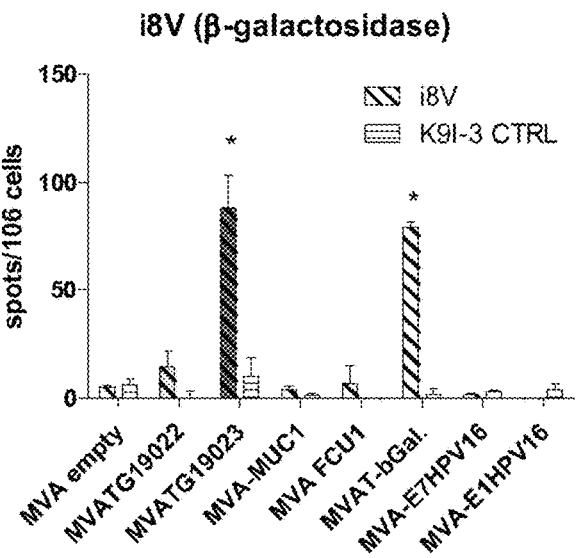

Importantly, the IFNγ response induced after immunization with MVATG19023 is at levels comparable to the one provided by the full-length antigen and even better for the anti E7 response (FIG. 2C). Hence, juxtaposition of peptides in a MVA backbone permits the development of a diversified immune response without observing immunodominance phenomenon curtailing these responses.

Example 2: Immunization with a CT26 Neopeptide Construct

Selection of CT26 Neopeptides

Ten CT26 mutated neopeptides were selected for expression in the MVA constructs (amino acid sequences are given in SEQ ID NO: 22-31) based on various criteria described in the art such as low score for MHC class I binding, the presence of CD8+ T cell epitopes (Kreiter et al., 2015, Nature 520 (7549): 692-6) and the presence of the single residue mutation in the genome of the respective CT26 tumor cell line. Each neopeptide is a 27 mer comprising the mutation at the central position (position 14) and separated from the following by a 10-amino acid GS linker for optimal processing and epitope presentation.

Vector Construction and Production

Two MVA constructs, MVATG19030 and MVATG19038 respectively, were generated for the expression of the above-described CT26 neopeptides arranged in two fusions (pentatopes). The first pentatope fusion is placed under the transcriptional control of the p11K7.5 promoter (SEQ ID NO: 8) and the second under pH5R control (SEQ ID NO: 14). Flag tag (SEQ ID NO: 6) is present at the C-terminus of the first pentatope fusion and c-MYC tag (SEQ ID NO: 11) at the end of the second fusion. MVATG19038 distinguishes from MVATG19030 by the presence of signal peptides originating from the rabies glycoprotein (SEQ ID NO: 9) at the N-terminus of the first pentatope fusion and from the measles F glycoprotein (SEQ ID NO: 15) at the N-terminus of the second pentatope fusion. The two neopeptide fusion cassettes were inserted into deletion III of the MVA genome. In MVATG19030, the first and second pentatope fusions comprise respectively the amino acid sequence as set forth in SEQ ID NO: 12 and SEQ ID NO: 13 (also illustrated in FIG. 3) while MVATG19038 comprise an amino acid sequence as set forth in SEQ ID NO: 16 and SEQ ID NO:17.

Evaluation of CT26 Neopeptide Expression

The expression of the CT26 neopeptide fusions was evaluated by Western blot in CEF infected with MVATG19030 and MVATG19038. Briefly, CEF were infected or not (Mock control) at MOI of 0.2 with MVATG19030 or MVATG19038 or with an empty (i.e. non-recombinant) MVA (TGN33.1 as negative control). Cells were harvested after 24 h and cell lysates analyzed by SDS-PAGE. Immunodetection of the expression products was detected using antibodies directed to the Flag and c-MYC tags included in the expression cassettes. Non-specific bands were highlighted with the anti-MYC antibody but also present in the negative controls. Whatever the background, the pentatopes were detected with both antibodies corresponding to the expected size for the neopeptide fusions directed by MVATG19030 (20.6 kDa for both pentatopes) and MVATG19038 (23.1 kDa for the first pentatope and 23.5 kDa for the second pentatope). As expected, no specific bands were detected in cell lysates obtained from cells infected with the empty MVA or the Mock buffer (although background bands were present in the samples treated with anti-cMYC as mentioned above).

Therefore, this study confirms the expression of the two neopeptide fusions in infected cells. As in Example 1, the presence of a peptide signal influenced positively the expression and higher levels were observed for the neopeptide fusions equipped with peptide signals as evidenced by the more intense bands obtained with MVATG19038 compared to those detected in cells infected with MVATG19030.

Immunogenicity Evaluation

The capacity of MVATG19030 and MVATG19038 to generate a T cell response against the encoded CT26 neopeptides was tested by ELIspot IFNγ in a CT26 tumoral model of Balb/c mice. Five animals per group were treated. One half of Balb/c mice were injected intravenously in the tail vein at day 0 with the tumoral CT-26 MUC1 cells ($2\times10^5$ cells in 100p1) (groups 1-5) while the remaining half of animals (groups 6-11) was left untreated. MVA injections were performed at day 2 and 9 by the intravenously route with $1\times10^7$ pfu in 100 μL of the previously described virus formulation buffer. Mice were sacrificed one week after the last MVA immunization (day 16). Spleens were collected for lymphocyte isolation and treated as detailed in Material and Methods. Stimulation was performed with either the mutated CT26 neopeptides (SEQ ID NO: 22 to 31) or their non-mutated homologues (wild-type peptides described in SEQ ID NO: 32 to 41) or with CD8+CT26 peptides either mutated (described in SEQ ID NO: 42 to 45) or wild-type (in SEQ ID NO: 46 to 49). The wild-type CT26 peptides were pooled in order to reduce the number of samples to handle whereas the mutated CT26 peptides were used either individually or in peptide pools.

Figure 4:
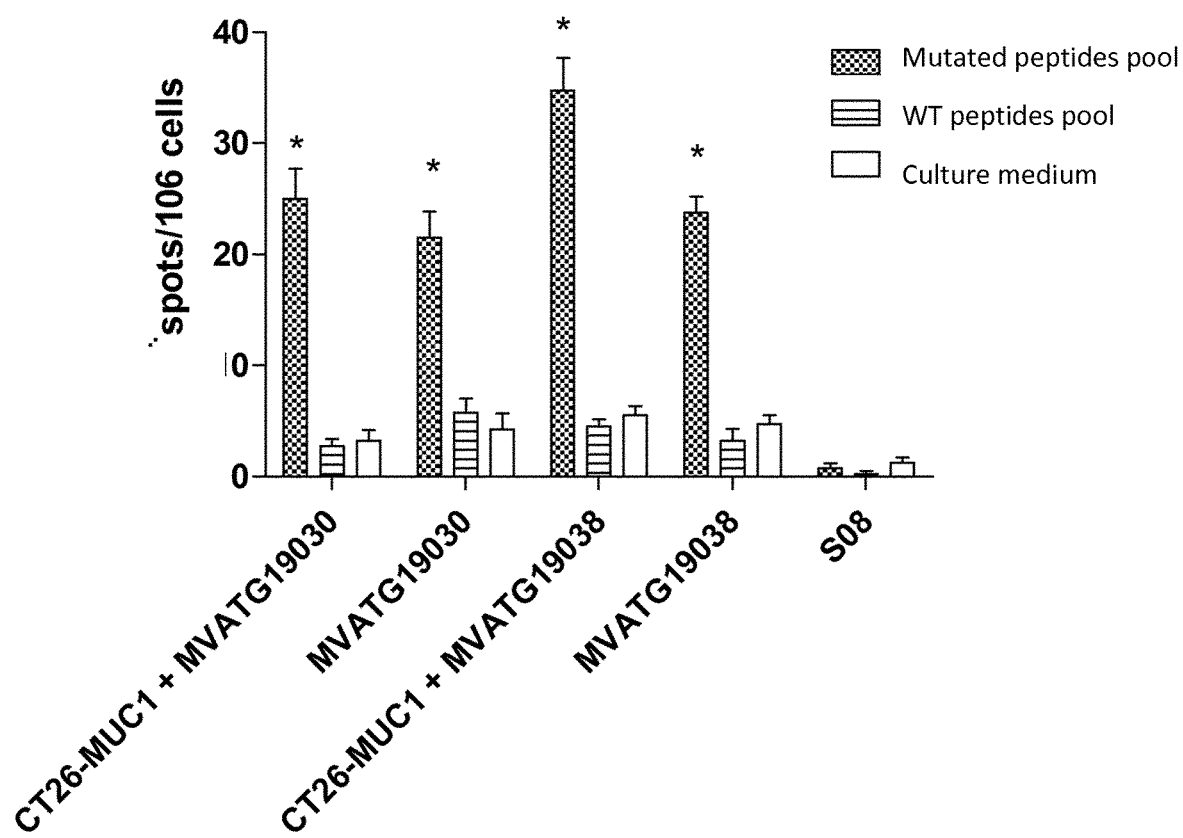
FIG. 4 illustrates ELISpot following immunization of Balb/c mice (5 mice per group) with MVATG19030 and MVATG19038 vectors. IFNγ response was evaluated after stimulation with either a pool of ten mutated CT26 peptides or a pool of CT26 wild-type peptides (i.e; which do not comprise the tumor-specific mutation) with or without CT26-MUC1 cells priming.

As illustrated in FIG. 4, following immunization with MVATG19030 and MVATG19038 vectors and stimulation with a pool gathered the ten mutated CT26 peptides, a high IFNγ response was generated whatever the vector injected and the animal model (primed with CT26-MUC1 cells or not). In contrast, stimulation with the pool of ten wild-type CT26 peptides does not produce any IFNγ production as well as with the medium negative control.

Figure 5:
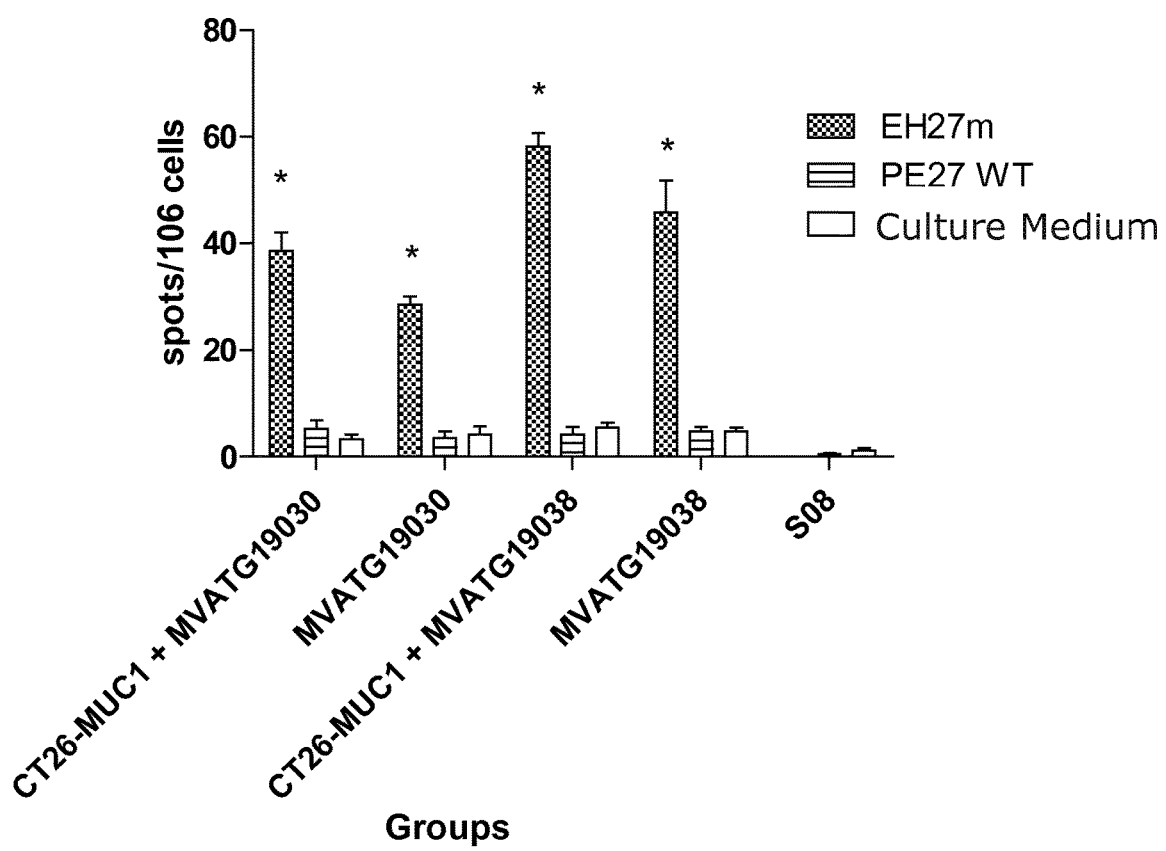
FIG. 5 illustrates the IFNγ response generated against a CT26 mutated peptide (EH27m) and a non-mutated CT26 peptide (PE27 wt) following immunization of Balb/c mice with MVATG19030 and MVATG19038 (or with the virus formulation buffer S08 as a negative control) both in the mouse model primed with CT26-MUC1 cells or not. Stimulation with culture medium is performed as a negative control.

FIG. 5 illustrates the IFNγ response generated against one of the mutated peptide (EH27m; SEQ ID NO: 30) following immunization with MVATG19030 and MVATG19038 both in the mouse model primed with CT26-MUC1 cells or not. In both cases (primed or not) a response varying from 30 to 60 spots is generated whereas, in contrast, stimulation with a wild-type peptide (PE27WT SEQ ID NO: 37) does not generate any IFNγ production (<5 spots). To be noted that the response generated with the signal peptide-equipped MVA vector (MVATG19038) is slightly higher than that obtained with the MVATG19030 which fusions do not incorporate any signal peptide. Here again no response (<5 spots) is detected with the medium negative control.

Figure 6:
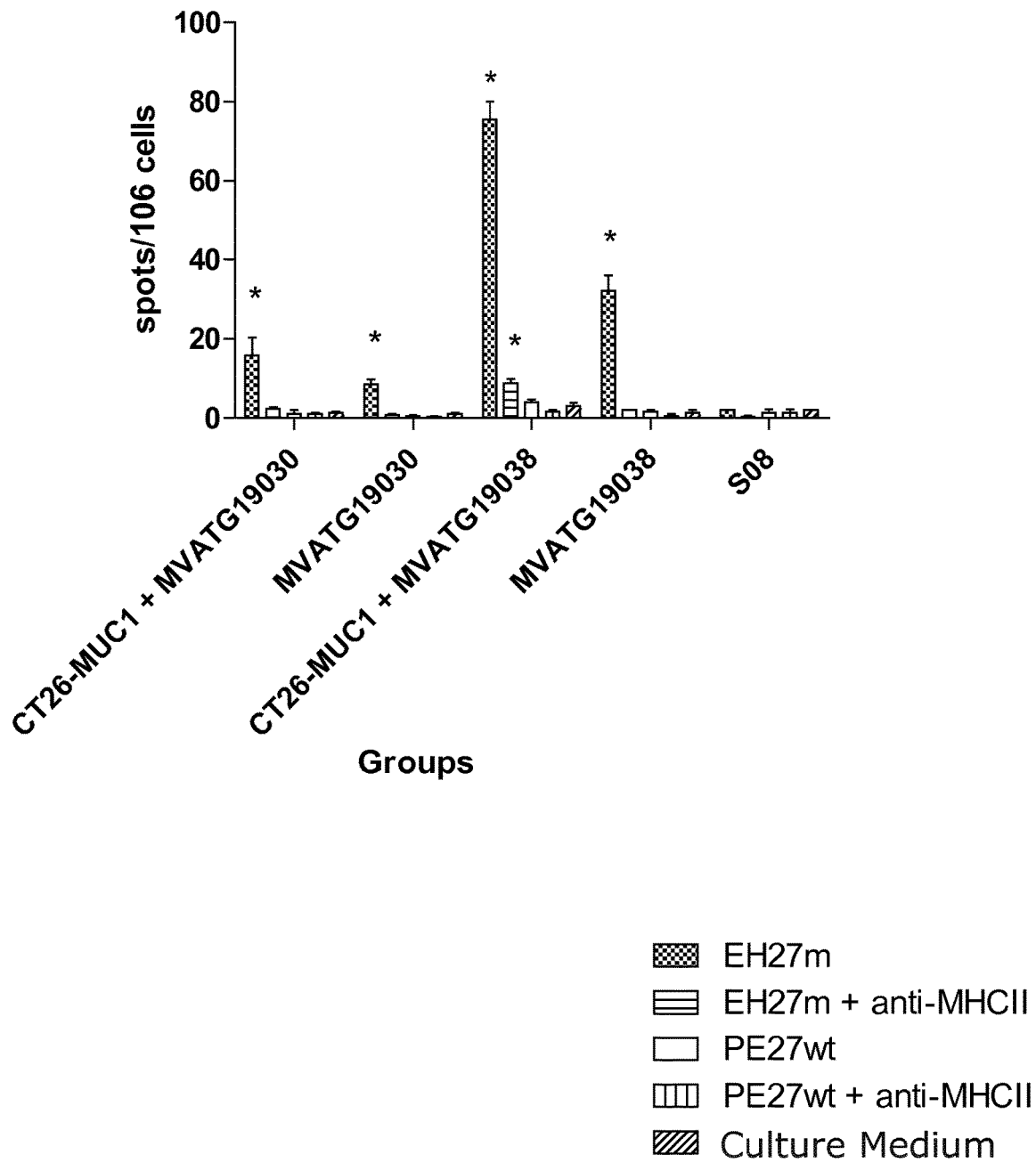
FIG. 6 illustrates the IFNγ response generated against a CT26 mutated peptide (EH27m) and a non-mutated CT26 peptide (PE27 wt) following immunization of Balb/c mice with MVATG19030 and MVATG19038 (or with the virus formulation buffer S08 as a negative control) both in the mouse model primed with CT26-MUC1 cells or not. The IFNγ response is evaluated in the presence (+anti-MHCII) or in the absence of anti-mouse MHCII antibodies. Stimulation with culture medium is performed as a negative control.

Moreover, the response against the mutated peptide (EH27m) is inhibited after blockage with anti-mouse MHCII antibodies as shown in FIG. 6 which might indicate that the response is CD4+-type.

In conclusion, these results support the feasibility of personalized cancer vaccine for human anti-cancer therapy.

Example 3: Human Neopeptide Construct

Identification and Selection of Neopeptides

Whole Exome Sequencing (WES) of tumor and germline samples of a patient suffering from NSCLC were performed in paired-end mode (2×150 bp) to identify tumor specific somatic mutations. For information, raw data are provided by sequencing facility into a standard file format, named FASTQ. Each sequencing run leads to the generation of a FASTQ file which provides short reads sequences and a per base quality score, the Phred score. It is based on an estimated error probability during the base calling step (Cock et al., 2010, Nucl. Acid Res. 38(6): 1767-71). In paired-end sequencing, two FASTQ files are generated, each corresponding to an end of the library fragment. The resulting files must thus remain paired during the quality filtering step, i.e. the two reads of a pair must have passed the filter. Criteria assessed during this filtering steps are mainly based on Phred scores, especially in the 3' end of the sequence, which often requires trimming to keep accurate information for the variant calling step (Edgar and Flyvbjerg, 2015, Bioinformatics 31(21): 3476-82).

Short reads are then aligned against a reference genome (Li et al., 2009, Bioinformatics 25(16): 2078-79). After this mapping step, variant calling algorithms are used to detect a variety of structural variations, such as single-nucleotide variants (SNVs including silent and non-silent missense mutations) or small insertions and deletions (indels) between the reference genome and the patient sequences (Danecek P. et al., 2011, Bioinformatics 27(15): 2156-58; Nielsen et al., 2011, Nature Reviews Genetics 12(6): 443-51). Samples from tumor and control tissue are processed at the same time to detect tumor-specific mutations.

The mutations are then evaluated at the protein level to design 17-mers mutation-centered peptides when possible, according to the position of the mutation. These candidate peptides are then evaluated at the expression level, with data from the tumor transcriptome (Hundal et al., 2016, Genome Medicine 8(1): 11). Tumor transcriptome was measured by RNA-Seq in paired-end mode (2×150 bp) to evaluate the expression of the neoantigens. Due to RNA-Seq sensitivity, a gene was considered expressed when a read coverage depth above 3× was reached. The quantification step starts after the mapping, by counting the number of reads mapped to a specific transcript adjusted by the library size in the total number of mapped reads per million (Wang et al., 2009, Nature Reviews Genetics 10(1): 57-63).

A total of 20 transcripts (corresponding to 18 unique genes) bearing at least one tumor-specific mutation has thus been identified. On this basis, 18 tumor-specific mutations have been selected and 18 neopeptides have been designed.

The 18 neopeptides have the features described in following Table 2:

TABLE 2

Features of the 18 neopeptides selected for a patient suffering from NSCLC

| Neo-peptide | Non-silent tumor-specific mutation type | Size (amino acids) | Position of mutation |
|---|---|---|---|
| NP1 | Missense | 19 | 4 |
| NP2 | Missense | 29 | 15 |
| NP3 | Missense | 29 | 15 |
| NP4 | Missense | 29 | 15 |
| NP5 | Missense | 29 | 15 |
| NP6 | Missense | 29 | 15 |
| NP7 | Missense | 29 | 15 |
| NP8 | Missense | 29 | 15 |
| NP9 | Missense | 29 | 15 |
| NP10 | Missense | 26 | 15 |
| NP11 | Missense | 29 | 15 |
| NP12 | Missense | 29 | 15 |
| NP13 | Missense | 29 | 15 |
| NP14 | Missense | 29 | 15 |
| NP15 | Frameshift | 76 | 15-76 |
| NP16 | Missense | 29 | 15 |
| NP17 | Missense | 29 | 15 |
| NP18 | Missense | 21 | 15 |

Of the 18 selected neopeptides:
  All have a size between 19 and 76.
  17/18 (94%) are based on a missense mutation resulting in changing one amino acid of the wild-type peptide and 1/18 (6%) has a frameshift mutation.
  Among the missense-bearing mutated neopeptides:
    they have a size between 19 and 29 amino acids,
    15/17 (88%) have a central mutation as defined herein, and
    14/17 (83%) have a size of 29 amino acids and a central mutation.

Vector Construction and Production

A search for transmembrane domain and signal peptide has been performed for each peptide using the Uniprot description of the corresponding gene as source of information. None of the neopeptides were known to be part of either a transmembrane or signal peptide in their respective protein. Using Uniprot, known functions associated with these peptides were searched. Peptides were either out of known domain or too short to form a functional domain. Three expression cassettes containing 7 neopeptides (heptatope), 6 neopeptides (hexatope) and 5 neopeptide (pentatope) were designed with the following rule:
  The 19 mer neopeptide NP1 that comprises a missense mutation positioned at the neoantigen N-terminus, was positioned at the N terminus of the heptatope expression cassette.
  On the same line, neopeptide NP18 that is naturally positioned at the neoantigen C-terminus, was positioned at the C-terminus of the expression cassette encoding the pentatope.
  Neopeptide NP10 was shortened of its last 3 residues due to their potential involvement in disulfide bond formation and placed in the middle of the hexatope cassette to disfavor any fold.
  Finally, neopeptide NP13 was predicted to form a potential transmembrane helix by the Geneious software and therefore was placed at the end of cassette encoding for the hexatope.

The neopeptides were separated by a 5-amino acid spacer for optimal processing of the fusion polypeptide and epitope presentation. Four different spacers were used: GSGSG, SGSGS, GSTSG and SGTGS. The amino acid sequences as well as the codon sequences were varied in order to decrease the percentage of nucleotide identity between the different linkers to reduce the risk of homologous recombination between the 17 linkers used in this construction. Signal peptides were fused to the N-terminus of each fusion of neopeptide to address the polypeptide to the RE. Signal peptides obtained from the rabies glycoprotein were added at the N-terminus of the heptatope and the pentatope, while a signal peptide derived for the measles F glycoprotein was added at the N-terminus of the hexatope.

In order to detect the expression of these three cassettes, tags from viral origins (i.e. HA (SEQ ID NO: 18), HSV (SEQ ID NO: 19) and VSV (SEQ ID NO: 20) tags for heptatope, hexatope and pentatope respectively) were added at the C-terminus of each construct.

The three neopeptide fusion cassettes were inserted into deletion III of the MVA genome giving rise to MVATG19111. More specifically, the first cassette encoded a heptatope fusion of 255 residues, the second cassette a hexatope fusion of 239 residues and the third cassette a pentatope fusion of 243 residues. MVATG19111 was produced by homologous recombination in CEF according to the process described in Material and Methods. This optimized protocol allowed to generate the recombinant MVA in only three weeks and to produce a purified bulk with an additional week.

Evaluation of Expression

The expression of the patient's neopeptide fusions was evaluated by Western blot in CEF infected with MVATG19111. Briefly, CEF were infected or not (Mock control) at MOI of 0.2 with MVATG19111 or with an empty (i.e. non-recombinant) MVA (TGN33.1 as negative control). Cells were harvested after 24 h and cell lysates analyzed by SDS-PAGE. Immunodetection of the expression products was detected using antibodies directed to the HA, HSV and VSV tags included in the expression cassettes. The results show that a specific band was detected for each neopeptide fusions directed by MVATG19111. The apparent sizes of the bands were slightly higher than the expected sizes for each fusion: about 38 kDa for the heptatope (expected size: 28.2 kDa), about 30 kDa for the hexatope (expected size: 25.5 kDa) and about 36 kDa for the pentatope (expected size: 25.9 kDa). The difference could be due to post-translational modifications. As expected no specific bands were detected in cell lysates obtained from cells infected with the empty MVA or the Mock buffer.

Evaluation of Immunogenicity

By design, MVATG19111 targets human antigens derived from tumor specific mutations. To evaluate immunogenicity of this vaccine it is therefore required to use a humanized murine model. The Human Leukocyte Antigen (HLA)-A2.1 transgenic mice (HHD) murine model offers the possibility to generate immune responses specific to the human HLA A02*01 haplotype (Firat et al. 1999, European Journal of Immunology 29(10): 3112-21). Additionally, expression of murine HLA molecule is disrupted in this mouse, preventing the development of a murine specific immune response. HHD mice were used to evaluate immunogenicity of the vaccine. Mice received $1.10^7$ pfu of MVATG19111 vaccine or MVA TGN33.1 in 200 µl of phosphate buffered saline (PBS) by intravenous injection at day 1 and day 7. Animals were sacrificed at D14 and splenocytes collected and frozen until analysis. The number of IFN-γ producing cells was determined in an IFN-γ ELISpot.

Briefly, single cell suspensions of spleens from mice vaccinated with MVATG19111 or control virus MVATGN33.1 were cultured on ELISPOT plates at $5\times10^5$ cells/well in 200 µl complete medium for 48 hours in different stimulation conditions. Stimulation conditions included a positive control (a mix of MVA peptides), a negative control (5 µg/ml of unrelated peptide), individual peptides, or one of 18 peptide pools each related to one of the antigens expressed in the vaccines (5 µg/ml of overlapping 20-mer peptides) or overlapping peptides corresponding to the non-mutated human protein. After incubation, plates were washed and the IFN-γ producing cells were detected using a colorimetric method and spots counted using a commercially available automated software. Immune responses were considered positive when the number of spot was statistically different from the analytical background.

In animal receiving the MVATG19111 vaccine, 7 out of 18 conditions yielded positive immune responses. More specifically, 4 conditions were highly immunogenic and induced detectable T cell responses in all animals while 3 others were immunogenic in some animals only. Differences in immunogenicity may be related to sensitivity of the assay or variability in immune phenotypes. Responses were restricted to the mutated protein and the vaccine did not elicit immunization against the non-mutated protein. In the control animal receiving the control virus MVATGN33.1, no response was observed.

Additionally, ELISPOT were conducted for highly immunogenic peptides in presence of an anti-class II MHC or after depletion of CD8 cells using anti-CD8 depleting beads as previously described (Puliaev et al., 2004, J. Immunol. 173(2): 910-9) in order to characterize the phenotype of reacting T cells. Responses were observed both after CD8 depletion and MHC II blockade, demonstrating that MVATG19111 was able to induce both Class I (CD8) and Class II (CD4) mediated responses.

Production and Therapeutic Use

The produced MVATG19111 bulk may be distributed in individual doses of approximately $10^8$ pfu that are stored at −80 or −20° C. before being administered to the patient from which the tumor was obtained.

Example 4: Role of the Linkers in the Neoepitope Fusions 4.1 Effect of the Linkers on Immunogenicity The effect of the linkers was first studied starting from the MVATG19023 vector described in Example 1, by varying the length and the sequence of the linkers. MVATG19023 encodes a fusion of 5 antigenic peptides originating from FCU1, β-Galactosidase, HPV-16 E1, HPV-16 E7 and MUC1 (from N to C-terminus of the fusion). Each peptide was a 27-mer comprising a validated C57bl/6 (b haplotype) T cell epitope positioned in the centre of the 27-mer except for Muc1 which epitope corresponds to the 15 last C-terminus residues of the antigen (see Table 3). Ten residue-long (5-times GS) linkers were present at the N and C termini of each peptide as well as a rabies signal peptide at the fusion N-terminus and a Flag tag at its C-terminus. The fusion was placed under the control of the p11k7.5 promoter and inserted in MVA's deletion III.

TABLE 3 primary structure of each 27mer with the encoded epitope highlighted (bold, italic and underlined)

| Antigen | 27mer sequence (epitope) | Name of epitope |
|---|---|---|
| FCU1 | CSKEGI_EKYHAAFPEVRIVTG_ALDRGL (SEQ ID NO: 1) | EG-15 (SEQ ID NO: 54) |
| β-gal | GGADTTATDI_ICPMYARV_DEDQPFPAV (SEQ ID NO: 2) | I8V (SEQ ID NO: 51) |
| E1 HPV16 | YDNDIVDDSE_IAYKYAQI_ADTNSNASA (SEQ ID NO: 3) | I8L (SEQ ID NO: 50) |
| E7 HPV16 | GPAGQAEPD_RAHYNIVTF_CCKCDSTLR (SEQ ID NO: 4) | R9F (SEQ ID NO: 52) |
| MUC1 | YEKVSAGNGGS_SLSYTNPAVAATSANL_ (SEQ ID NO: 5) | L15L-3 (SEQ ID NO: 53) |

In MVATG19023, the same 10 residue linker was present before and after each epitope. To circumvent homologous recombination events that may generate, and lead to partial or total cassette deletion, it is advisable to degenerate each linker DNA sequence by taking advantage of the genetic code degeneracy. However, this sequence degeneration is limited by the number, the nature and length of the linkers. In case of a large number of epitopes to be vectorized (e.g. 10 or above), the genetic code does not allow to create sufficient DNA diversity to avoid homologous recombination with a 5-times GS linker. Therefore, the possibility to use smaller linkers (GSG), other residues than serine (GAS or GTS) and eventually no linker at all, was investigated. Viruses were produced on CEP. After clarification, the viruses were purified by tangential flow filtration (TFF). This leads to the generation of MVATG190158, MVATG190159 and MVATG190157 illustrated in Table 4.

TABLE 4

Features of the recombinant MVA generated for this study.

| MVA | Signal peptide | Linker |
|---|---|---|
| MVATG19023 | Rabies | GSGSGSGSGS |
| MVATG19157 | Rabies | None |
| MVATG19158 | Rabies | GSG |
| MVATG19159 | Rabies | GAS or GTS |

The immunogenicity induced by these 3 constructs was evaluated by ELISPOT and compared to the one given by MVATG19023 in the same conditions of immunization as described previously.

The ELISPOT results show that immune responses were roughly similar for MVATG19023, MVATG19158, MVATG19159 and MVATG19157 for 4 epitopes out of 5 (L15L3, I8L, I8V and R9F) whereas the response to EG15 trended to be slightly higher for MVATG19023 containing the 10-residue linker.

These results show that the presence, the nature, the length of linkers at the N and C termini of the various antigenic peptides to be expressed have no major effect for the immunogenicity of such peptides.

4.2 Effect of the Linkers on the Generation of Recombinant Poxvirus

The presence or absence of linkers was also tested for the ability of the constructs to generate recombinant poxviruses in the context of the pTG19111 vector (described in Example 3). An additional plasmid was generated comprising the same neopeptide fusions as pTG19111 but without any linkers, giving pTG19264. The obtention of recombinant MVA viruses was compared between the no linker (pTG19264) and the 5aa linker (pTG19111) constructs in transfected CEF cells as described herein, white plaques corroborating with potential recombinant MVA and red plaques with parental (not recombinant) virus.

As shown in Table 5, although both constructs led to the obtention of white plaques, their proportion was nevertheless higher with the linker-containing pTG19111 vector.

TABLE 5

Effect of the presence or absence of linkers on the generation

| Construct | Fusion | 1 | 2 | 3 | Linker | % white plaques |
|---|---|---|---|---|---|---|
| TG19111 | Neopeptide number | 7 | 6 | 5 | 5 aa | 21.7% |
| TG19264 | Neopeptide number | 7 | 6 | 5 | no | 1.5% |

All together these results indicate that the absence of linkers does not have a major impact on immunogenicity although altering negatively the proportion of white plaques generated in CEF cells and thus the generation of recombinant MVA. Therefore, if needed, linkers may be omitted to facilitate the design of vector constructs and thus reduce the risk of deleterious homologous recombination events, especially in constructs where expression of more than 10 neopeptides is considered but with the risk of reducing the proportion of recombinant poxviruses generated.

Example 5: Hydrophobicity Analysis 5.1 Prediction of TM Segments

The presence of intra or inter TM segment was tested in the context of pTG19247 plasmid. As mentioned above, pTG19247 carries three expression cassettes each encoding ten neopeptides (which amino acid sequences are described in SEQ ID NO: 60, 61 and 62) originating from human lung adenocarcinoma (study PRJEB3132) with a signal sequence at the N-terminus of each fusion. To facilitate the construction, no linkers were included between the selected neopeptides. Generation of the corresponding MVA was assayed in CEF by homologous recombination according to the process disclosed above and the number of white versus red plaques was numbered. A low ratio of white plaques below % was obtained and PCR analysis of the white plaques revealed the absence of recombinant MVA carrying the neopeptide fusions.

Prediction of TM sequences in each neopeptide fusion was carried out using the TMHMM prediction algorithm. No TM sequence could be predicted in fusion 1. However, two potential interpeptide TM segments were identified in fusion 2, respectively at the junction of neopeptide 1 and neopeptide 2 and of neopeptide 7 and neopeptide 8. On the other hand, three intrapeptide TM segments were identified in fusion 3, more specifically within neopeptides 2, 4 and 5.

A no TM construct named pTG19258 was then generated comprising the same neopeptide fusion 1 as pTG19247, a fusion 2 as illustrated in SEQ ID NO: 63 where neopeptides 1 and 2 were inversed as well as neopeptides 7 and 8 allowing suppression of these inter peptide TM segments (this new fusion 2 thus comprises from N to C neopeptide 2, neopeptide 1, neopeptide 3, neopeptide 4, neopeptide 6, neopeptide 8, neopeptide 7, neopeptide 9 and neopeptide 10) and a fusion 3 as illustrated in SEQ ID NO: 64 where neopeptides 2, 4 and 5 were eliminated. Moreover, the promoter p11K7.5 used to drive fusion 3 in pTG19247 was replaced by p7.5K promoter in pTG19258. A higher percentage of white plaque was obtained upon transfection of CEF cells. However, after isolation and amplification of 20 white plaques, only 6 white plaques remained, and PCR analysis revealed that all correspond to parental virus mutated in mCherry (none of them corresponded to a recombinant virus).

The influence of hydrophobicity was further investigated by determining hydrophobicity and hydropathy scores for each neopeptide and fusion.

5.2 Hydrophobicity Analysis

Hydrophobicity analysis was carried out to determine the hydrophobicity and hydropathy scores of all neopeptides encoded by the construct MVATG19111, pTG19247 and pTG19258 using the Kyte and Doolittle method. The results for the 3 fusions encoded by MVATG19111 are reported in the following Table 6.

TABLE 6 hydrophobicity and hydropathy scores detected for each neopeptide and fusion thereof carried by MVATG19111.

| Neopeptide | Hydrophobicity score | Hydropathy score |
|---|---|---|
| NP1 | −10.3 | −0.51 |
| NP2 | −8.8 | −0.30 |
| NP3 | −1.1 | −0.038 |
| NP4 | −24.5 | −0.845 |
| NP5 | −61.3 | −2.114 |
| NP6 | −38.8 | −1.338 |
| NP7 | −6.2 | −0.214 |
| Total Fusion 1 | −151 | −0.778 |
| Total Fusion 1 + linkers | −170.3 | −0.76 |
| NP8 | −12.8 | −0.44 |
| NP9 | −31.1 | −1.07 |
| NP10 | −9.6 | −0.33 |
| NP11 | −32.2 | −1.11 |
| NP12 | 14.5 | 0.5 |
| NP13 | −2.7 | −0.104 |
| Total Fusion 2 | −73.9 | −0.42 |
| Total Fusion 2 + linkers | −92 | −0.45 |
| NP14 | −20 | −0.690 |
| NP15 | −8.7 | −0.3 |
| NP16 | −27.2 | −0.938 |
| NP17 | −3.7 | −0.176 |
| NP18 | −4.4 | −0.058 |
| Total Fusion 3 | −64 | −0.34 |
| Total Fusion 3 + linkers | −79.5 | −0.38 |

These results show that 17 out of the 18 neopeptides encoded by MVATG19111 display satisfactory hydrophobicity and hydropathy scores (negative values and below 0.1, respectively). Only neopeptide 12 comprised in the second fusion scored positively reflecting a hydrophobic nature of this particular peptide. Nevertheless, fusion 2 remained hydrophilic as reflected by its negative hydrophobicity (−74) and hydropathy (−0.42) scores.

The same prediction study was carried out for neopeptides and fusions encoded by pTG19247 and pTG19258 and the scores are reported in Tables 7 and 8, respectively.

TABLE 7 hydrophobicity and hydropathy scores detected for each neopeptide and fusions thereof carried by pTG19247.

| Neopeptide | Hydrophobicity score | Hydropathy score |
|---|---|---|
| NP1 fusion 1 | −7.7 | −0.28 |
| NP2 fusion 1 | −15.2 | −0.56 |
| NP3 fusion 1 | −22.3 | −0.82 |
| NP4 fusion 1 | 3 | 0.11 |
| NP5 fusion 1 | 7.3 | 0.27 |
| NP6 fusion 1 | −19.6 | −0.72 |
| NP7 fusion 1 | −24.6 | −0.91 |
| NP8 fusion 1 | −18.1 | −0.67 |
| NP9 fusion 1 | 23.1 | 0.85 |
| NP10 fusion 1 | −24.7 | −0.91 |
| Total Fusion 1 | −98.8 | −0.36 |
| NP1 fusion 2 | −3.6 | −0.13 |
| NP2 fusion 2 | 23.3 | 0.86 |
| NP3 fusion 2 | −11.2 | −0.41 |
| NP4 fusion 2 | 18.2 | 0.67 |
| NP5 fusion 2 | 0.3 | 0.011 |
| NP6 fusion 2 | −28.4 | −1.05 |
| NP7 fusion 2 | −3.2 | −0.119 |
| NP8 fusion 2 | −8.3 | −0.346 |
| NP9 fusion 2 | −23.0 | −0.85 |
| NP10 fusion 2 | 15.6 | 0.578 |
| Total Fusion 2 | −20.3 | −0.076 |
| NP1 fusion 3 | −1.9 | −0.07 |
| NP2 fusion 3 | 46.4 | 1.72 |
| NP3 fusion 3 | 1.2 | 0.044 |
| NP4 fusion 3 | 21 | 0.778 |
| NP5 fusion 3 | 37.6 | 1.393 |
| NP6 fusion 3 | 14.2 | 0.526 |
| NP7 fusion 3 | 4.9 | 0.181 |
| NP8 fusion 3 | −13.0 | −0.48 |
| NP9 fusion 3 | −13.2 | −0.49 |
| NP10 fusion 3 | 36.3 | 1.34 |
| Total Fusion 3 | 133.5 | 0.494 |

The results highlight the highly hydrophobic nature of fusion 3 as evidenced by a positive hydrophobicity (133.5) and hydropathy (0.494) scores.

The same investigation was made in the context of pTG19258 which corresponds to the TM-deleted version of pTG19247 as described above. Hydrophobicity and hydropathy scores of fusions 1 and 2 are the same as those reported in Table 7 (same fusion carried by both vectors and fusion 2 comprising the same neopeptides with inversed order of neopeptides 1 and 2 and 7 and 8 in pTG19258 to eliminate interpeptide TM-segments). Table 8 provides the hydrophobicity and hydropathy scores for fusion 3 of pTG19258 (fusion of 7 neopeptides which was deleted of TM-containing neopeptides 2, 4 and 5 with respect to its pTG19247 counterpart).

TABLE 8 hydrophobicity and hydropathy scores detected for each neopeptide and fusion 3 carried by pTG19258

| Neopeptide | Hydrophobicity score | Hydropathy score |
|---|---|---|
| NP1 | −1.9 | −0.07 |
| NP3 | 1.2 | 0.044 |
| NP6 | 14.2 | 0.526 |
| NP7 | 4.9 | 0.181 |
| NP8 | −13.0 | −0.48 |
| NP9 | −13.2 | −0.49 |
| NP10 | 36.3 | 1.34 |
| Total Fusion 3 | 28.5 | 0.151 |

Although elimination of highly hydrophobic and TM-containing neopeptides 2, 4 and 5, the global scoring of pTG19258 fusion 3 translates in hydrophobic nature.

Therefore, additional constructs were generated, respectively

A version of pTG19258 deleted of fusion 3 (named pTG19288)

A version of pTG19258 including 3 amino acid linkers at the N terminus of the first neopeptide and between each neopeptide comprised in the three fusions (pTG19267)

Elimination of the third fusion in pTG19267 (pTG19293)

Replacement in pTG19258 of the third fusion with another one containing 10 other neopeptides selected from the public lung adenocarcinoma data bank and predicted hydrophilic (negative hydrophobic score), without no linkers (pTG19290; SEQ ID NO: 65) or with 3 amino acid linkers at the N and C termini of each neopeptide (pTG19291).

Elimination of fusion 1 in pTG19291 (pTG19298).

The obtention of recombinant MVA viruses was assayed in transfected CEF cells by these new plasmid constructs as described herein and compared to the parental plasmid pTG19258. Red plaques correlate with parental (not recombinant) virus while white plaques is an indication of potential recombinant MVA. But additional PCR analyses are required on a panel of white and red plaques to discriminate between not recombinant (i.e. parental) and recombinant viruses (mCherry negative or mCherry positive, the latter reflecting a contamination of recombinant plaques with parental). The results are summarized in FIG. 8.

As shown in FIG. 8, pTG19258 did not lead to the generation of any recombinant MVA virus. Although white plaques were generated, no fusion-bearing viruses could be detected by PCR analysis although no TM segments could be identified in this construct (nevertheless fusion 3 scores positively reflecting its hydrophobic nature). The white plaques were due to parental virus mutated in the mCherry marker gene.

Adding linkers between neopeptides in each fusion cassette permitted to reduce hydrophobic feature of fusion 3 (hydropathy score was reduced to a value below 0.1 from 0.151 to 0.0.08). This modification was translated in a higher percentage of white plaque (13.3%) generated in CEF cells giving 7 recombinant viruses confirmed by PCR analyses.

Replacing the hydrophobic fusion 3 in pTG19258 by another one made of 10 hydrophilic neopeptides (hydropathy scoring of −0.52) was also beneficial for recombinant MVA virus generation whatever the presence (pTG19291) or the absence (pTG19290) of linkers in the neopeptide fusions, giving respectively 7 and 6 recombinants viruses generated.

Elimination of fusions to remain with only 2 fusions of 10 neopeptides each scoring negatively for hydrophobicity, enhanced the percentage of white plaques to 16% and the recovery of recombinant viruses (10 and 11 recombinants identified by PCR).

All together, these results point out optimal design of neopeptide fusions as summarized hereinafter:

Elimination of potential TM-segments (intra or inter peptides);

Selection of rather hydrophilic neopeptides (scoring negatively for hydrophobicity) or reduction of the number of hydrophobic neopeptides (scoring negatively for hydrophobicity), e.g. to less than 40%;

Arrangement of neopeptides in fusion(s);

Presence of a signal peptide at the N-terminus of each fusion recommended

Presence of 3 amino acid linkers between neopeptides and at the N-term of the first neopeptide (e.g. GTS, GSG or GAS as exemplified in FIG. 7)

Incorporation in the viral genome of 1 to 3 fusions of 6 to 10 neopeptides.

BIBLIOGRAPHIC REFERENCES

Acres and Bonnefoy, 2008, Expert Review of Vaccines 7, 889-93;
Altschul et al., 1990, J. Mol. Biol. 215(3):403-10;
Anderson and Schrijver, 2010, Genes 1(1): 38-69;
Andreatta et al., 2015, Immunogenetics 67(11-12): 641-50;
Antoine et al., 1998, Virol. 244: 365-96;
Bainbridge et al., 2010, Genome Biol. 11:R62;
Boegel et al., 2015, Methods Mol Biol 1310: 247-51;
Caroll et al., 1997, Virology 238: 198-211;
Carpentier et al., 2003, Frontiers in Bioscience 8, e115-127;
Carpentier et al., 2006, Neuro-Oncology 8(1): 60-6;
Chakrabarti et al. 1997, Biotechniques 23: 1094-7;
Chu and Corey, 2012, Nucleic Acid Ther. 22: 271-4;
Claudepierre et al., 2014, J. Virol. 88(10): 5242-55;
Cock et al., 2010, Nucl. Acid Res. 38(6): 1767-71;
Danecek P. et al., 2011, Bioinformatics 27(15): 2156-58;
Edgar and Flyvbjerg, 2015, Bioinformatics 31(21): 3476-82;
EP 1 162 982;
EP 463 756;
Erbs et al., 2008, Cancer Gene Ther. 15(1): 18-28;
Farsaci et al., 2011, In Cancer Vaccines: From Research to Clinical Practice, Ed Bot; CRC Press, pp 56-77;
Fend et al., 2014, Cancer Immunol. Res. 2, 1163-74;
Firat et al. 1999, European Journal of Immunology 29(10): 3112-21;
Gulley et al., 2008, Clin Cancer Res 14(10): 3060-9;
Guse et al., 2011, Expert Opinion Biol. Ther. 11(5):595-608;
Hammond et al, 1997, J. Virol Methods 66: 135-8;
Hundal et al., 2016, Genome Medicine 8(1): 11;
Husseini et al., 2017, Ann Oncol 28(1): 169-74;
Kallol et al., 2003, J. Chromat. 1000: 637-55;
Kern et al., 1990, Gene 88: 149-57;
Kreiter et al. 2015, Nature, 520: 692-6;
Krogh et al., 2001, J. Mol. Biol. 305: 567-80;
Kumar and Boyle, 1990, Virology 179: 151-8;
Kyte and Doolittle, 1982, J. Mol. Biol. 157: 105-32;
Li et al., 2009, Bioinformatics 25(16): 2078-79;
Maniatis et al. 1989, Laboratory Manual, Cold Spring Harbor Laboratory Press, Cold Spring Harbor N.Y.;
Mayr et al., 1975, Infection 3: 6-14;
Meyer et al., 1991, J. Gen. Virol. 72: 1031-8;
Moodie et al. 2006, J. Immunol Methods 315: 121-32;
Moodie et al. 2010, Cancer Immunol Immunother doi 10.1007/s00262-010-0875-4;
Ng S. B. et al, 2009, Nature 461: 272-6;
Nielsen et al., 2010, Immunology 130(3): 319-28;
Nielsen et al., 2011, Nature Reviews Genetics 12(6): 443-51;
Olivier et al., 2010, mAbs 2(4): 405-15;
Plotkin, 2008, Clin Infect Dis. 47(3):401-9;
Quoix et al., 2011, The Lancet Oncology 12(12): 1125-33;
Relman, 2008, J Infect Dis. 198(1):4-5;
Rock et al., 2010, J. Immunol. 184(1): 9-15;
Rose et al., 1993, Ann. Rev. Biomol. Struc. 22: 381-415;
Sutter and Moss, 1992, Proc. Natl. Acad. Sci. USA 89: 10847-51;
Sweet et al., 1983, J. Mol. Biol. 171: 479-88;
U.S. Pat. No. 5,250,534;
U.S. Pat. No. 5,972,597;
U.S. Pat. No. 6,440,422;
U.S. Pat. No. 6,469,012;
U.S. Pat. No. 6,998,252;

U.S. Pat. No. 7,108,844;
U.S. Pat. No. 7,700,569;
U.S. Pat. No. 5,879,924;
Wang et al., 2009, Nature Reviews Genetics 10(1): 57-63;
WO03/008533;
WO03/053463;
WO2005/007840;
WO2005/042728;
WO2006/0850082;
WO2007/056847;
WO2007/077256;
WO2007/147528;
WO2008/092854;
WO2008/114021;
WO2008/129058;
WO2008/138533,
WO2009/004016;
WO2009/065546;
WO2009/065547;
WO2009/100521;
WO2010/130753;
WO2010/130756;
WO2012/001075;
WO2012/159754;
WO2013/022764;
WO2014/053571;
WO2015/175334;
WO2015/175340;
WO2016/187508;
WO2016/191545;
WO2016/207859;
WO97/02355;
WO99/03885;
Yuan et al., 2015, J. Virol 89, 5176-9, doi:10.1128;
Yuan et al., 2016, Viruses 8, 72, doi:10.3390;

The invention claimed is:

1. A process for preparing a recombinant poxvirus comprising a heterologous nucleic acid sequence encoding a neopeptide fusion comprising 2 to 15 neopeptides, said process comprising:
   (a) identifying a plurality of selected neopeptides, wherein the identification step comprises the following sub-steps i) to v):
      i) extracting nucleic acids from a tumor sample and a non-tumor sample;
      ii) sequencing corresponding regions from the extracted nucleic acids from the tumor sample and the non-tumor sample;
      iii) comparing the nucleic acid sequences obtained from the tumor and non-tumor samples to identify a plurality of tumor specific mutations;
      iv) determining the tumor specific mutations that are expressed at the mRNA expression and/or protein translation level in the tumor sample to identify one or more neoantigens, wherein the one or more neoantigens comprise a plurality of potential neopeptides; and
      v) identifying and selecting from the plurality of potential neopeptides those that are not present in the proteome of the non-tumor sample to obtain the plurality of selected neopeptides;
   (b) generating amino acid sequences for a plurality of potential neopeptide fusions, wherein each potential neopeptide fusion comprises the amino acid sequences of 2 to 15 of the selected neopeptides, optionally comprising intervening linker sequences of 2 to 15 amino acids between one or more of the selected neopeptide sequences, wherein at least 60% of the selected neopeptides in each potential neopeptide fusion comprise a missense or a frameshift mutation;
   (c) determining the degree of hydrophobicity of each of said potential neopeptide fusions and selecting a neopeptide fusion that has a negative hydrophobicity score and/or a hydropathy score equal or below 0.1;
   (d) generating a nucleic acid fusion sequence for said selected neopeptide fusion; and
   (e) generating a recombinant poxvirus by inserting a nucleic acid molecule comprising said nucleic acid fusion sequence into the genome of a parental recombinant poxvirusi wherein the poxvirus is a vaccinia virus.

2. The process according to claim 1, wherein said tumor sample is a tumor biopsy and wherein said non-tumor sample is a biological fluid, a cytological material or a biopsy.

3. The process according to claim 1, wherein the nucleic acid molecule is arranged in-an expression cassette under the control of regulatory elements.

4. The process according to claim 1, wherein said parental recombinant poxvirus comprises a fluorescent reporter gene cloned at the site of insertion that is selected for the nucleic acid molecule or the expression cassette.

5. The process according to claim 4, wherein said fluorescent reporter is selected from the group consisting of GFP (Green Fluorescent Protein), eGFP (Enhanced Green Fluorescent Protein), AmCyan 1 fluorescent protein and m Cherry.

6. The process according to claim 5, wherein said step of generating said recombinant poxvirus comprises a further step of cleavage by an endonuclease able to generate at least one double strand break in said fluorescent reporter nucleotide sequence but in which said endonuclease does not cleave the poxviral genome.

7. The process according to claim 6, wherein said endonuclease is selected from the group consisting of zinc finger nucleases (ZFNs), transcription activator-like effector nucleases (TALENs), clustered regularly interspaced short palindromic repeats (CRISPR)/Cas9 nucleases and restriction enzymes with unique cleavage site within the fluorescent reporter gene.

8. The process according to claim 1, wherein said process further comprises a manufacturing step, wherein said manufacturing step comprises an amplification step in a producer cell, a step of recovery of the produced recombinant poxvirus from the cell culture and an optional step of purification of the recovered recombinant poxvirus.

9. The process according to claim 8, wherein said producer cell is chicken embryo fibroblasts (CEF).

10. The process according to claim 8, wherein said step of recovery of the produced recombinant poxvirus comprises a lysis step wherein the producer cell membrane is disrupted by using a high-speed homogenizer.

11. The process according to claim 8, wherein said purification step comprises a tangential flow filtration (TFF) step.

12. The process according to claim 8, wherein said manufacturing step reaches the production of at least $10^9$ pfu.

13. The process according to claim 1, wherein said recombinant poxvirus is a Modified Vaccinia Ankara (MVA) virus.

14. The process according to claim 1, wherein said selected neopeptides comprising a missense mutation have a length from 18 to 29 residues and said selected neopeptides comprising a frameshift mutation have a length from 30 to 80 amino acid residues.

15. The process according to claim 1, wherein the recombinant poxvirus comprising a heterologous nucleic acid sequence encodes 2 or 3 fusions, wherein:
    each fusion comprises 5 to 10 neopeptides;
    each fusion comprises linkers at the N-terminus of the first neopeptide, and between each neopeptide;
    each fusion comprises a signal peptide at the N terminus of said fusion;
    and each fusion has a negative hydrophobicity score and/or a hydropathy score equal or below 0.1.

16. The process according to claim 3, wherein the recombinant poxvirus comprises two or three expression cassettes.

17. The process according to claim 3, wherein said nucleic acid fusion sequence is codon optimized for expression in mammalian cells.

18. The process according to claim 1, wherein said selected neopeptide fusion does not contain a predicted transmembrane segment.

* * * * *

SEQUENCE LISTING

```
<160> NUMBER OF SEQ ID NOS: 70

<210> SEQ ID NO 1
<211> LENGTH: 27
<212> TYPE: PRT
<213> ORGANISM: artificial sequence
<220> FEATURE:
<223> OTHER INFORMATION: FCU1 peptide

<400> SEQUENCE: 1

Cys Ser Lys Glu Gly Ile Glu Lys Tyr His Ala Ala Phe Pro Glu Val
1               5                   10                  15

Arg Ile Val Thr Gly Ala Leu Asp Arg Gly Leu
            20                  25

<210> SEQ ID NO 2
<211> LENGTH: 27
<212> TYPE: PRT
<213> ORGANISM: artificial sequence
<220> FEATURE:
<223> OTHER INFORMATION: peptide obtained from beta galatosidase antigen

<400> SEQUENCE: 2

Gly Gly Ala Asp Thr Thr Ala Thr Asp Ile Ile Cys Pro Met Tyr Ala
1               5                   10                  15

Arg Val Asp Glu Asp Gln Pro Phe Pro Ala Val
            20                  25

<210> SEQ ID NO 3
<211> LENGTH: 27
<212> TYPE: PRT
<213> ORGANISM: artificial sequence
<220> FEATURE:
<223> OTHER INFORMATION: peptide obtained from HPV-16 E1 antigen

<400> SEQUENCE: 3

Tyr Asp Asn Asp Ile Val Asp Asp Ser Glu Ile Ala Tyr Lys Tyr Ala
1               5                   10                  15

Gln Leu Ala Asp Thr Asn Ser Asn Ala Ser Ala
            20                  25

<210> SEQ ID NO 4
<211> LENGTH: 27
<212> TYPE: PRT
<213> ORGANISM: artificial sequence
<220> FEATURE:
```

<223> OTHER INFORMATION: peptide obtained from HPV-16 E7 antigen

<400> SEQUENCE: 4

Gly Pro Ala Gly Gln Ala Glu Pro Asp Arg Ala His Tyr Asn Ile Val
1               5                   10                  15

Thr Phe Cys Cys Lys Cys Asp Ser Thr Leu Arg
            20                  25

<210> SEQ ID NO 5
<211> LENGTH: 27
<212> TYPE: PRT
<213> ORGANISM: artificial sequence
<220> FEATURE:
<223> OTHER INFORMATION: peptide obtained from MUC1 antigen

<400> SEQUENCE: 5

Tyr Glu Lys Val Ser Ala Gly Asn Gly Gly Ser Ser Leu Ser Tyr Thr
1               5                   10                  15

Asn Pro Ala Val Ala Ala Thr Ser Ala Asn Leu
            20                  25

<210> SEQ ID NO 6
<211> LENGTH: 8
<212> TYPE: PRT
<213> ORGANISM: artificial sequence
<220> FEATURE:
<223> OTHER INFORMATION: Flag tag

<400> SEQUENCE: 6

Asp Tyr Lys Asp Asp Asp Asp Lys
1               5

<210> SEQ ID NO 7
<211> LENGTH: 204
<212> TYPE: PRT
<213> ORGANISM: artificial sequence
<220> FEATURE:
<223> OTHER INFORMATION: fusion of 5 peptides expressed by MVATG19022

<400> SEQUENCE: 7

Met Gly Ser Gly Ser Gly Ser Gly Ser Cys Ser Lys Glu Gly
1               5                   10                  15

Ile Glu Lys Tyr His Ala Ala Phe Pro Glu Val Arg Ile Val Thr Gly
                20                  25                  30

Ala Leu Asp Arg Gly Leu Gly Ser Gly Ser Gly Ser Gly Ser
            35                  40                  45

Gly Gly Ala Asp Thr Thr Ala Thr Asp Ile Ile Cys Pro Met Tyr Ala
    50                  55                  60

Arg Val Asp Glu Asp Gln Pro Phe Pro Ala Val Gly Ser Gly Ser Gly
65                  70                  75                  80

Ser Gly Ser Gly Ser Tyr Asp Asn Asp Ile Val Asp Ser Glu Ile
                85                  90                  95

Ala Tyr Lys Tyr Ala Gln Leu Ala Asp Thr Asn Ser Asn Ala Ser Ala
            100                 105                 110

Gly Ser Gly Ser Gly Ser Gly Ser Gly Ser Pro Ala Gly Gln Ala
            115                 120                 125

Glu Pro Asp Arg Ala His Tyr Asn Ile Val Thr Phe Cys Cys Lys Cys
        130                 135                 140

Asp Ser Thr Leu Arg Gly Ser Gly Ser Gly Ser Gly Ser Tyr
145                 150                 155                 160

```
Glu Lys Val Ser Ala Gly Asn Gly Gly Ser Ser Leu Ser Tyr Thr Asn
                165                 170                 175

Pro Ala Val Ala Ala Thr Ser Ala Asn Leu Gly Ser Gly Ser Gly Ser
            180                 185                 190

Gly Ser Gly Ser Asp Tyr Lys Asp Asp Asp Lys
        195                 200

<210> SEQ ID NO 8
<211> LENGTH: 112
<212> TYPE: DNA
<213> ORGANISM: artificial sequence
<220> FEATURE:
<223> OTHER INFORMATION: fragment of vaccinia promoter p11k7.5

<400> SEQUENCE: 8
ataaaaatat agtagaattt cattttgttt ttttctatgc tataaatagg atccgataaa     60
gtgaaaaata attctaattt attgcacggt aaggaagtag aatcataaag aa           112

<210> SEQ ID NO 9
<211> LENGTH: 23
<212> TYPE: PRT
<213> ORGANISM: artificial sequence
<220> FEATURE:
<223> OTHER INFORMATION: fragment of rabbies glycoprotein (signal
      peptide)

<400> SEQUENCE: 9

Met Val Pro Gln Ala Leu Leu Phe Val Pro Leu Leu Val Phe Pro Leu
1               5                   10                  15

Cys Phe Gly Lys Phe Pro Ile
            20

<210> SEQ ID NO 10
<211> LENGTH: 226
<212> TYPE: PRT
<213> ORGANISM: artificial sequence
<220> FEATURE:
<223> OTHER INFORMATION: fusion of 5 peptides encoded by MVATG19023
      (+ signal peptide)

<400> SEQUENCE: 10

Met Val Pro Gln Ala Leu Leu Phe Val Pro Leu Leu Val Phe Pro Leu
1               5                   10                  15

Cys Phe Gly Lys Phe Pro Ile Gly Ser Gly Ser Gly Ser Gly Ser Gly
            20                  25                  30

Ser Cys Ser Lys Glu Gly Ile Glu Lys Tyr His Ala Ala Phe Pro Glu
        35                  40                  45

Val Arg Ile Val Thr Gly Ala Leu Asp Arg Gly Leu Gly Ser Gly Ser
    50                  55                  60

Gly Ser Gly Ser Gly Ser Gly Ala Asp Thr Thr Ala Thr Asp Ile
65                  70                  75                  80

Ile Cys Pro Met Tyr Ala Arg Val Asp Glu Asp Gln Pro Phe Pro Ala
                85                  90                  95

Val Gly Ser Gly Ser Gly Ser Gly Ser Tyr Asp Asn Asp Ile
            100                 105                 110

Val Asp Asp Ser Glu Ile Ala Tyr Lys Tyr Ala Gln Leu Ala Asp Thr
        115                 120                 125

Asn Ser Asn Ala Ser Ala Gly Ser Gly Ser Gly Ser Gly Ser
    130                 135                 140

Gly Pro Ala Gly Gln Ala Glu Pro Asp Arg Ala His Tyr Asn Ile Val
```

```
                    145                 150                 155                 160

Thr Phe Cys Cys Lys Cys Asp Ser Thr Leu Arg Gly Ser Gly Ser Gly
                165                 170                 175

Ser Gly Ser Gly Ser Tyr Glu Lys Val Ser Ala Gly Asn Gly Gly Ser
                180                 185                 190

Ser Leu Ser Tyr Thr Asn Pro Ala Val Ala Ala Thr Ser Ala Asn Leu
                195                 200                 205

Gly Ser Gly Ser Gly Ser Gly Ser Asp Tyr Lys Asp Asp Asp
    210                 215                 220

Asp Lys
225

<210> SEQ ID NO 11
<211> LENGTH: 10
<212> TYPE: PRT
<213> ORGANISM: artificial sequence
<220> FEATURE:
<223> OTHER INFORMATION: cMYC tag

<400> SEQUENCE: 11

Glu Gln Lys Leu Ile Ser Glu Glu Asp Leu
1               5                   10

<210> SEQ ID NO 12
<211> LENGTH: 204
<212> TYPE: PRT
<213> ORGANISM: artificial sequence
<220> FEATURE:
<223> OTHER INFORMATION: fusion of 5 CT26 neopeptides (pentatope 1)

<400> SEQUENCE: 12

Met Gly Ser Gly Ser Gly Ser Gly Ser Tyr Arg Gly Ala Asn
1               5                   10                  15

Leu His Leu Glu Glu Thr Leu Ala Gly Phe Trp Ala Arg Leu Leu Glu
                20                  25                  30

Arg Leu Phe Lys Gln Leu Gly Ser Gly Ser Gly Ser Gly Ser Gly Ser
                35                  40                  45

Gly Tyr Ile Ser Arg Val Thr Ala Gly Lys Asp Ser Tyr Ile Ala Leu
    50                  55                  60

Val Asp Lys Asn Ile Met Gly Tyr Ile Ala Ser Gly Ser Gly Ser Gly
65                  70                  75                  80

Ser Gly Ser Gly Ser Ala Gly Thr Gln Cys Glu Tyr Trp Ala Ser Arg
                85                  90                  95

Ala Leu Asp Ser Glu His Ser Ile Gly Ser Met Ile Gln Leu Pro Gln
                100                 105                 110

Gly Ser Gly Ser Gly Ser Gly Ser Glu Gly Asp Pro Cys Leu
                115                 120                 125

Arg Ser Ser Asp Cys Ile Asp Glu Phe Cys Cys Ala Arg His Phe Trp
    130                 135                 140

Thr Lys Ile Cys Lys Gly Ser Gly Ser Gly Ser Gly Ser Gly Ser Val
145                 150                 155                 160

Thr Ser Ile Pro Ser Val Ser Asn Ala Leu Asn Trp Lys Glu Phe Ser
                165                 170                 175

Phe Ile Gln Ser Thr Leu Gly Tyr Val Ala Gly Ser Gly Ser Gly Ser
                180                 185                 190

Gly Ser Gly Ser Asp Tyr Lys Asp Asp Asp Asp Lys
    195                 200
```

<210> SEQ ID NO 13
<211> LENGTH: 206
<212> TYPE: PRT
<213> ORGANISM: artificial sequence
<220> FEATURE:
<223> OTHER INFORMATION: fusion of 5 CT26 neopeptides (pentatope 2)
      encoded by MVATG19030

<400> SEQUENCE: 13

Met Gly Ser Gly Ser Gly Ser Gly Ser Gly Ser Pro Leu Leu Pro Phe
1               5                   10                  15

Tyr Pro Pro Asp Glu Ala Leu Glu Ile Gly Leu Glu Leu Asn Ser Ser
            20                  25                  30

Ala Leu Pro Pro Thr Glu Gly Ser Gly Ser Gly Ser Gly Ser Gly Ser
        35                  40                  45

Val Ile Leu Pro Gln Ala Pro Ser Gly Pro Ser Tyr Ala Thr Tyr Leu
    50                  55                  60

Gln Pro Ala Gln Ala Gln Met Leu Thr Pro Pro Gly Ser Gly Ser Gly
65                  70                  75                  80

Ser Gly Ser Gly Ser Asp Lys Pro Leu Arg Arg Asn Asn Ser Tyr Thr
                85                  90                  95

Ser Tyr Ile Met Ala Ile Cys Gly Met Pro Leu Asp Ser Phe Arg Ala
            100                 105                 110

Gly Ser Gly Ser Gly Ser Gly Ser Gly Ser Glu Val Ile Gln Thr Ser
        115                 120                 125

Lys Tyr Tyr Met Arg Asp Val Ile Ala Ile Glu Ser Ala Trp Leu Leu
    130                 135                 140

Glu Leu Ala Pro His Gly Ser Gly Ser Gly Ser Gly Ser Gly Ser Glu
145                 150                 155                 160

His Ile His Arg Ala Gly Gly Leu Phe Val Ala Asp Ala Ile Gln Val
                165                 170                 175

Gly Phe Gly Arg Ile Gly Lys His Phe Trp Gly Ser Gly Ser Gly Ser
            180                 185                 190

Gly Ser Gly Ser Glu Gln Lys Leu Ile Ser Glu Glu Asp Leu
        195                 200                 205

<210> SEQ ID NO 14
<211> LENGTH: 114
<212> TYPE: DNA
<213> ORGANISM: artificial sequence
<220> FEATURE:
<223> OTHER INFORMATION: fragment of vaccinia promoter pH5R

<400> SEQUENCE: 14
tttattctat acttaaaaaa tgaaaataaa tacaaaggtt cttgagggtt gtgttaaatt      60
gaaagcgaga aataatcata aattatttca ttatcgcgat atccgttaag tttg          114

<210> SEQ ID NO 15
<211> LENGTH: 28
<212> TYPE: PRT
<213> ORGANISM: artificial sequence
<220> FEATURE:
<223> OTHER INFORMATION: fragment of measles F glycoprotein (signal
      peptide)

<400> SEQUENCE: 15

Met Gly Leu Lys Val Asn Val Ser Ala Ile Phe Met Ala Val Leu Leu
1               5                   10                  15

Thr Leu Gln Thr Pro Thr Gly Gln Ile His

```
                20                  25

<210> SEQ ID NO 16
<211> LENGTH: 226
<212> TYPE: PRT
<213> ORGANISM: artificial sequence
<220> FEATURE:
<223> OTHER INFORMATION: fusion of 5 CT26 neopeptides encoded by
      MVATG19038 (pentatope 1)

<400> SEQUENCE: 16

Met Val Pro Gln Ala Leu Leu Phe Val Pro Leu Leu Val Phe Pro Leu
1               5                   10                  15

Cys Phe Gly Lys Phe Pro Ile Gly Ser Gly Ser Gly Ser Gly Ser Gly
            20                  25                  30

Ser Tyr Arg Gly Ala Asn Leu His Leu Glu Glu Thr Leu Ala Gly Phe
        35                  40                  45

Trp Ala Arg Leu Leu Glu Arg Leu Phe Lys Gln Leu Gly Ser Gly Ser
    50                  55                  60

Gly Ser Gly Ser Gly Ser Gly Tyr Ile Ser Arg Val Thr Ala Gly Lys
65                  70                  75                  80

Asp Ser Tyr Ile Ala Leu Val Asp Lys Asn Ile Met Gly Tyr Ile Ala
                85                  90                  95

Ser Gly Ser Gly Ser Gly Ser Gly Ser Ala Gly Thr Gln Cys
            100                 105                 110

Glu Tyr Trp Ala Ser Arg Ala Leu Asp Ser Glu His Ser Ile Gly Ser
        115                 120                 125

Met Ile Gln Leu Pro Gln Gly Ser Gly Ser Gly Ser Gly Ser Gly Ser
    130                 135                 140

Glu Gly Asp Pro Cys Leu Arg Ser Ser Asp Cys Ile Asp Glu Phe Cys
145                 150                 155                 160

Cys Ala Arg His Phe Trp Thr Lys Ile Cys Lys Gly Ser Gly Ser Gly
                165                 170                 175

Ser Gly Ser Gly Ser Val Thr Ser Ile Pro Ser Val Ser Asn Ala Leu
            180                 185                 190

Asn Trp Lys Glu Phe Ser Phe Ile Gln Ser Thr Leu Gly Tyr Val Ala
        195                 200                 205

Gly Ser Gly Ser Gly Ser Gly Ser Asp Tyr Lys Asp Asp Asp
    210                 215                 220

Asp Lys
225

<210> SEQ ID NO 17
<211> LENGTH: 232
<212> TYPE: PRT
<213> ORGANISM: artificial sequence
<220> FEATURE:
<223> OTHER INFORMATION: fusion of 5 CT26 neopeptides encoded by
      MVATG19038 (pentatope 2)

<400> SEQUENCE: 17

Met Gly Leu Lys Val Asn Val Ser Ala Ile Phe Met Ala Val Leu Leu
1               5                   10                  15

Thr Leu Gln Thr Pro Thr Gly Gln Ile His Trp Gly Ser Gly Ser Gly
            20                  25                  30

Ser Gly Ser Gly Ser Pro Leu Leu Pro Phe Tyr Pro Pro Asp Glu Ala
        35                  40                  45

Leu Glu Ile Gly Leu Glu Leu Asn Ser Ser Ala Leu Pro Pro Thr Glu
```

Gly Ser Gly Ser Gly Ser Gly Ser Val Ile Leu Pro Gln Ala
65                  70                  75                  80

Pro Ser Gly Pro Ser Tyr Ala Thr Tyr Leu Gln Pro Ala Gln Ala Gln
                85                  90                  95

Met Leu Thr Pro Pro Gly Ser Gly Ser Gly Ser Gly Ser Asp
            100                 105                 110

Lys Pro Leu Arg Arg Asn Asn Ser Tyr Thr Ser Tyr Ile Met Ala Ile
        115                 120                 125

Cys Gly Met Pro Leu Asp Ser Phe Arg Ala Gly Ser Gly Ser Gly Ser
    130                 135                 140

Gly Ser Gly Ser Glu Val Ile Gln Thr Ser Lys Tyr Tyr Met Arg Asp
145                 150                 155                 160

Val Ile Ala Ile Glu Ser Ala Trp Leu Leu Glu Leu Ala Pro His Gly
                165                 170                 175

Ser Gly Ser Gly Ser Gly Ser Gly Ser Glu His Ile His Arg Ala Gly
            180                 185                 190

Gly Leu Phe Val Ala Asp Ala Ile Gln Val Gly Phe Gly Arg Ile Gly
        195                 200                 205

Lys His Phe Trp Gly Ser Gly Ser Gly Ser Gly Ser Gly Ser Glu Gln
    210                 215                 220

Lys Leu Ile Ser Glu Glu Asp Leu
225                 230

<210> SEQ ID NO 18
<211> LENGTH: 9
<212> TYPE: PRT
<213> ORGANISM: artificial sequence
<220> FEATURE:
<223> OTHER INFORMATION: HA tag

<400> SEQUENCE: 18

Tyr Pro Tyr Asp Val Pro Asp Tyr Ala
1               5

<210> SEQ ID NO 19
<211> LENGTH: 11
<212> TYPE: PRT
<213> ORGANISM: artificial sequence
<220> FEATURE:
<223> OTHER INFORMATION: HSV tag

<400> SEQUENCE: 19

Gln Pro Glu Leu Ala Pro Glu Asp Pro Glu Asp
1               5                   10

<210> SEQ ID NO 20
<211> LENGTH: 11
<212> TYPE: PRT
<213> ORGANISM: artificial sequence
<220> FEATURE:
<223> OTHER INFORMATION: VSV tag

<400> SEQUENCE: 20

Tyr Thr Asp Ile Glu Met Asn Arg Leu Gly Lys
1               5                   10

<210> SEQ ID NO 21
<211> LENGTH: 100
<212> TYPE: DNA
<213> ORGANISM: artificial sequence
<220> FEATURE:
<223> OTHER INFORMATION: fragment of vaccinia pB2R promoter

<400> SEQUENCE: 21
tatattatta agtgtggtgt ttggtcgatg taaaattttt gtcgataaaa attaaaaaat      60
aacttaattt attattgatc tcgtgtgtac aaccgaaatc                          100

<210> SEQ ID NO 22
<211> LENGTH: 27
<212> TYPE: PRT
<213> ORGANISM: artificial sequence
<220> FEATURE:
<223> OTHER INFORMATION: CT26 peptide 1

<400> SEQUENCE: 22

Tyr Arg Gly Ala Asn Leu His Leu Glu Glu Thr Leu Ala Gly Phe Trp
1               5                   10                  15

Ala Arg Leu Leu Glu Arg Leu Phe Lys Gln Leu
            20                  25

<210> SEQ ID NO 23
<211> LENGTH: 27
<212> TYPE: PRT
<213> ORGANISM: artificial sequence
<220> FEATURE:
<223> OTHER INFORMATION: CT26 peptide 2

<400> SEQUENCE: 23

Gly Tyr Ile Ser Arg Val Thr Ala Gly Lys Asp Ser Tyr Ile Ala Leu
1               5                   10                  15

Val Asp Lys Asn Ile Met Gly Tyr Ile Ala Ser
            20                  25

<210> SEQ ID NO 24
<211> LENGTH: 27
<212> TYPE: PRT
<213> ORGANISM: artificial sequence
<220> FEATURE:
<223> OTHER INFORMATION: CT26 peptide 3

<400> SEQUENCE: 24

Ala Gly Thr Gln Cys Glu Tyr Trp Ala Ser Arg Ala Leu Asp Ser Glu
1               5                   10                  15

His Ser Ile Gly Ser Met Ile Gln Leu Pro Gln
            20                  25

<210> SEQ ID NO 25
<211> LENGTH: 27
<212> TYPE: PRT
<213> ORGANISM: artificial sequence
<220> FEATURE:
<223> OTHER INFORMATION: CT26 neopeptide 4

<400> SEQUENCE: 25

Glu Gly Asp Pro Cys Leu Arg Ser Ser Asp Cys Ile Asp Glu Phe Cys
1               5                   10                  15

Cys Ala Arg His Phe Trp Thr Lys Ile Cys Lys
            20                  25

<210> SEQ ID NO 26
<211> LENGTH: 27
<212> TYPE: PRT
<213> ORGANISM: artificial sequence
<220> FEATURE:

<223> OTHER INFORMATION: CT26 neopeptide 5

<400> SEQUENCE: 26

Val Thr Ser Ile Pro Ser Val Ser Asn Ala Leu Asn Trp Lys Glu Phe
1               5                   10                  15

Ser Phe Ile Gln Ser Thr Leu Gly Tyr Val Ala
            20                  25

<210> SEQ ID NO 27
<211> LENGTH: 27
<212> TYPE: PRT
<213> ORGANISM: artificial sequence
<220> FEATURE:
<223> OTHER INFORMATION: CT26 neopeptide 6

<400> SEQUENCE: 27

Pro Leu Leu Pro Phe Tyr Pro Pro Asp Glu Ala Leu Glu Ile Gly Leu
1               5                   10                  15

Glu Leu Asn Ser Ser Ala Leu Pro Pro Thr Glu
            20                  25

<210> SEQ ID NO 28
<211> LENGTH: 27
<212> TYPE: PRT
<213> ORGANISM: artificial sequence
<220> FEATURE:
<223> OTHER INFORMATION: CT26 neopeptide 7

<400> SEQUENCE: 28

Val Ile Leu Pro Gln Ala Pro Ser Gly Pro Ser Tyr Ala Thr Tyr Leu
1               5                   10                  15

Gln Pro Ala Gln Ala Gln Met Leu Thr Pro Pro
            20                  25

<210> SEQ ID NO 29
<211> LENGTH: 27
<212> TYPE: PRT
<213> ORGANISM: artificial sequence
<220> FEATURE:
<223> OTHER INFORMATION: CT26 neopeptide 8

<400> SEQUENCE: 29

Asp Lys Pro Leu Arg Arg Asn Asn Ser Tyr Thr Ser Tyr Ile Met Ala
1               5                   10                  15

Ile Cys Gly Met Pro Leu Asp Ser Phe Arg Ala
            20                  25

<210> SEQ ID NO 30
<211> LENGTH: 27
<212> TYPE: PRT
<213> ORGANISM: artificial sequence
<220> FEATURE:
<223> OTHER INFORMATION: CT26 neopeptide 9

<400> SEQUENCE: 30

Glu Val Ile Gln Thr Ser Lys Tyr Tyr Met Arg Asp Val Ile Ala Ile
1               5                   10                  15

Glu Ser Ala Trp Leu Leu Glu Leu Ala Pro His
            20                  25

<210> SEQ ID NO 31
<211> LENGTH: 27
<212> TYPE: PRT
<213> ORGANISM: artificial sequence
<220> FEATURE:
<223> OTHER INFORMATION: CT26 neopeptide 10

<400> SEQUENCE: 31

Glu His Ile His Arg Ala Gly Gly Leu Phe Val Ala Asp Ala Ile Gln
1               5                   10                  15

Val Gly Phe Gly Arg Ile Gly Lys His Phe Trp
            20                  25

<210> SEQ ID NO 32
<211> LENGTH: 27
<212> TYPE: PRT
<213> ORGANISM: artificial sequence
<220> FEATURE:
<223> OTHER INFORMATION: non mutated CT26 peptide 1

<400> SEQUENCE: 32

Tyr Arg Gly Ala Asn Leu His Leu Glu Glu Thr Leu Ala Glu Phe Trp
1               5                   10                  15

Ala Arg Leu Leu Glu Arg Leu Phe Lys Gln Leu
            20                  25

<210> SEQ ID NO 33
<211> LENGTH: 27
<212> TYPE: PRT
<213> ORGANISM: artificial sequence
<220> FEATURE:
<223> OTHER INFORMATION: non mutated CT26 peptide 2

<400> SEQUENCE: 33

Gly Tyr Ile Ser Arg Val Thr Ala Gly Lys Asp Ser Tyr Leu Ala Leu
1               5                   10                  15

Val Asp Lys Asn Ile Met Gly Tyr Ile Ala Ser
            20                  25

<210> SEQ ID NO 34
<211> LENGTH: 27
<212> TYPE: PRT
<213> ORGANISM: artificial sequence
<220> FEATURE:
<223> OTHER INFORMATION: non mutated CT26 peptide 3

<400> SEQUENCE: 34

Ala Gly Thr Gln Cys Glu Tyr Trp Ala Ser Arg Ala Leu Gly Ser Glu
1               5                   10                  15

His Ser Ile Gly Ser Met Ile Gln Leu Pro Gln
            20                  25

<210> SEQ ID NO 35
<211> LENGTH: 27
<212> TYPE: PRT
<213> ORGANISM: artificial sequence
<220> FEATURE:
<223> OTHER INFORMATION: non mutated CT26 peptide 4

<400> SEQUENCE: 35

Glu Gly Asp Pro Cys Leu Arg Ser Ser Asp Cys Ile Asp Gly Phe Cys
1               5                   10                  15

Cys Ala Arg His Phe Trp Thr Lys Ile Cys Lys
            20                  25

<210> SEQ ID NO 36
<211> LENGTH: 27
<212> TYPE: PRT

-continued

```
<213> ORGANISM: artificial sequence
<220> FEATURE:
<223> OTHER INFORMATION: non mutated CT26 peptide 5

<400> SEQUENCE: 36

Val Thr Ser Ile Pro Ser Val Ser Asn Ala Leu Asn Trp Arg Glu Phe
1               5                   10                  15

Ser Phe Ile Gln Ser Thr Leu Gly Tyr Val Ala
            20                  25

<210> SEQ ID NO 37
<211> LENGTH: 27
<212> TYPE: PRT
<213> ORGANISM: artificial sequence
<220> FEATURE:
<223> OTHER INFORMATION: non mutated CT26 peptide 6

<400> SEQUENCE: 37

Pro Leu Leu Pro Phe Tyr Pro Pro Asp Glu Ala Leu Glu Thr Gly Leu
1               5                   10                  15

Glu Leu Asn Ser Ser Ala Leu Pro Pro Thr Glu
            20                  25

<210> SEQ ID NO 38
<211> LENGTH: 27
<212> TYPE: PRT
<213> ORGANISM: artificial sequence
<220> FEATURE:
<223> OTHER INFORMATION: non mutated CT26 peptide 7

<400> SEQUENCE: 38

Val Ile Leu Pro Gln Ala Pro Ser Gly Pro Ser Tyr Ala Ile Tyr Leu
1               5                   10                  15

Gln Pro Ala Gln Ala Gln Met Leu Thr Pro Pro
            20                  25

<210> SEQ ID NO 39
<211> LENGTH: 27
<212> TYPE: PRT
<213> ORGANISM: artificial sequence
<220> FEATURE:
<223> OTHER INFORMATION: non mutated CT26 peptide 8

<400> SEQUENCE: 39

Asp Lys Pro Leu Arg Arg Asn Asn Ser Tyr Thr Ser Tyr Thr Met Ala
1               5                   10                  15

Ile Cys Gly Met Pro Leu Asp Ser Phe Arg Ala
            20                  25

<210> SEQ ID NO 40
<211> LENGTH: 27
<212> TYPE: PRT
<213> ORGANISM: artificial sequence
<220> FEATURE:
<223> OTHER INFORMATION: non mutated CT26 peptide 9

<400> SEQUENCE: 40

Glu Val Ile Gln Thr Ser Lys Tyr Tyr Met Arg Asp Val Thr Ala Ile
1               5                   10                  15

Glu Ser Ala Trp Leu Leu Glu Leu Ala Pro His
            20                  25

<210> SEQ ID NO 41
<211> LENGTH: 27
```

```
<212> TYPE: PRT
<213> ORGANISM: artificial sequence
<220> FEATURE:
<223> OTHER INFORMATION: non mutated CT26 peptide 10

<400> SEQUENCE: 41

Glu His Ile His Arg Ala Gly Gly Leu Phe Val Ala Asp Glu Ile Gln
1               5                   10                  15

Val Gly Phe Gly Arg Ile Gly Lys His Phe Trp
            20                  25

<210> SEQ ID NO 42
<211> LENGTH: 9
<212> TYPE: PRT
<213> ORGANISM: artificial sequence
<220> FEATURE:
<223> OTHER INFORMATION: CD8 CT26 epitope 7M1

<400> SEQUENCE: 42

Pro Ser Tyr Ala Thr Tyr Leu Gln Pro
1               5

<210> SEQ ID NO 43
<211> LENGTH: 9
<212> TYPE: PRT
<213> ORGANISM: artificial sequence
<220> FEATURE:
<223> OTHER INFORMATION: CD8 CT26 epitope 7M2

<400> SEQUENCE: 43

Tyr Ala Thr Tyr Leu Gln Pro Ala Gln
1               5

<210> SEQ ID NO 44
<211> LENGTH: 9
<212> TYPE: PRT
<213> ORGANISM: artificial sequence
<220> FEATURE:
<223> OTHER INFORMATION: CD8 CT26 epitope 7M3

<400> SEQUENCE: 44

Thr Tyr Leu Gln Pro Ala Gln Ala Gln
1               5

<210> SEQ ID NO 45
<211> LENGTH: 9
<212> TYPE: PRT
<213> ORGANISM: artificial sequence
<220> FEATURE:
<223> OTHER INFORMATION: CD8 CT26 epitope 2M

<400> SEQUENCE: 45

Ile Ala Leu Val Asp Lys Asn Ile Met
1               5

<210> SEQ ID NO 46
<211> LENGTH: 9
<212> TYPE: PRT
<213> ORGANISM: artificial sequence
<220> FEATURE:
<223> OTHER INFORMATION: CD8 CT26 epitope 7WT1

<400> SEQUENCE: 46

Pro Ser Tyr Ala Ile Tyr Leu Gln Pro
1               5
```

```
<210> SEQ ID NO 47
<211> LENGTH: 9
<212> TYPE: PRT
<213> ORGANISM: artificial sequence
<220> FEATURE:
<223> OTHER INFORMATION: CD8 CT26 epitope 7WT2

<400> SEQUENCE: 47

Tyr Ala Ile Tyr Leu Gln Pro Ala Gln
1               5

<210> SEQ ID NO 48
<211> LENGTH: 9
<212> TYPE: PRT
<213> ORGANISM: artificial sequence
<220> FEATURE:
<223> OTHER INFORMATION: CD8 CT26 epitope 7WT3

<400> SEQUENCE: 48

Ile Tyr Leu Gln Pro Ala Gln Ala Gln
1               5

<210> SEQ ID NO 49
<211> LENGTH: 9
<212> TYPE: PRT
<213> ORGANISM: artificial sequence
<220> FEATURE:
<223> OTHER INFORMATION: CD8 CTe- epitope 2 WT

<400> SEQUENCE: 49

Leu Ala Leu Val Asp Lys Asn Ile Met
1               5

<210> SEQ ID NO 50
<211> LENGTH: 8
<212> TYPE: PRT
<213> ORGANISM: artificial sequence
<220> FEATURE:
<223> OTHER INFORMATION: stimulating peptide

<400> SEQUENCE: 50

Ile Ala Tyr Lys Tyr Ala Gln Leu
1               5

<210> SEQ ID NO 51
<211> LENGTH: 8
<212> TYPE: PRT
<213> ORGANISM: artificial sequence
<220> FEATURE:
<223> OTHER INFORMATION: stimulating peptide

<400> SEQUENCE: 51

Ile Cys Pro Met Tyr Ala Arg Val
1               5

<210> SEQ ID NO 52
<211> LENGTH: 9
<212> TYPE: PRT
<213> ORGANISM: artificial sequence
<220> FEATURE:
<223> OTHER INFORMATION: stimulating peptide

<400> SEQUENCE: 52

Arg Ala His Tyr Asn Ile Val Thr Phe
1               5

<210> SEQ ID NO 53
```

```
<211> LENGTH: 15
<212> TYPE: PRT
<213> ORGANISM: artificial sequence
<220> FEATURE:
<223> OTHER INFORMATION: stimulating peptide

<400> SEQUENCE: 53

Leu Ser Tyr Thr Asn Pro Ala Val Ala Ala Thr Ser Ala Asn Leu
1               5                   10                  15

<210> SEQ ID NO 54
<211> LENGTH: 15
<212> TYPE: PRT
<213> ORGANISM: artificial sequence
<220> FEATURE:
<223> OTHER INFORMATION: stimulating peptide

<400> SEQUENCE: 54

Glu Lys Tyr His Ala Ala Phe Pro Glu Val Arg Ile Val Thr Gly
1               5                   10                  15

<210> SEQ ID NO 55
<211> LENGTH: 8
<212> TYPE: PRT
<213> ORGANISM: artificial sequence
<220> FEATURE:
<223> OTHER INFORMATION: stimulating peptide

<400> SEQUENCE: 55

Thr Ser Tyr Lys Phe Glu Ser Val
1               5

<210> SEQ ID NO 56
<211> LENGTH: 9
<212> TYPE: PRT
<213> ORGANISM: artificial sequence
<220> FEATURE:
<223> OTHER INFORMATION: irrelevant peptide

<400> SEQUENCE: 56

Lys Asn Gly Glu Asn Ala Gln Ala Ile
1               5

<210> SEQ ID NO 57
<211> LENGTH: 15
<212> TYPE: PRT
<213> ORGANISM: artificial sequence
<220> FEATURE:
<223> OTHER INFORMATION: irrelevant peptide

<400> SEQUENCE: 57

Gly Ile Cys Leu Met Leu Phe Ile Leu Ile Lys Arg Ser Arg His
1               5                   10                  15

<210> SEQ ID NO 58
<211> LENGTH: 27
<212> TYPE: PRT
<213> ORGANISM: artificial sequence
<220> FEATURE:
<223> OTHER INFORMATION: example of a lung adenocarcinoma neopeptide
      which dispays negative hydrobobicity and hydropathy scores

<400> SEQUENCE: 58

Gly Gln Ser Leu Pro Met Thr His Ser Leu Lys Leu Ser Lys Thr Asn
1               5                   10                  15

Arg Thr Leu Phe Leu Leu Gly Val Thr Lys Tyr
            20                  25
```

<210> SEQ ID NO 59
<211> LENGTH: 27
<212> TYPE: PRT
<213> ORGANISM: artificial sequence
<220> FEATURE:
<223> OTHER INFORMATION: Example of a lung adenocarcinoma neopeptide
      which dispaly positive hydrophobicity and hydropathy scores

<400> SEQUENCE: 59

Gly Leu Met Gly Ile Val Val Gly Thr Val Phe Ile Ile Arg Gly Leu
1               5                   10                  15

Arg Ser Val Gly Ala Ser Arg His Gln Gly Leu
            20                  25

<210> SEQ ID NO 60
<211> LENGTH: 270
<212> TYPE: PRT
<213> ORGANISM: artificial sequence
<220> FEATURE:
<223> OTHER INFORMATION: fusion 1 of ten neopeptides encoded by pTG19247

<400> SEQUENCE: 60

Lys Glu His Gly Thr His Gln Gln Leu Leu Ala Gln Lys Val Ile Tyr
1               5                   10                  15

Phe Ser Met Val Ser Val Gln Ala Gly Thr Lys Ala Trp Glu Ser Trp
            20                  25                  30

Arg Ser Glu Val Gly Lys Gln Leu Met Pro Leu Tyr Glu Glu Tyr Val
        35                  40                  45

Val Leu Lys Asn Glu Met Asp Val Ser Lys Glu Asn Glu Asn Ser Met
50                  55                  60

Val Pro Gln Arg Ala Pro Val Gly Ser Leu Ser Val Lys Asn Lys Ala
65                  70                  75                  80

His Gln Met Lys Ala Arg Leu Thr Gln Glu Leu Gln Gln Ala Asn Asn
                85                  90                  95

Met His Asn Val Leu Gln Ala Glu Leu Asp Lys Leu His Leu His Tyr
            100                 105                 110

Pro Ile Glu Arg Gly Leu Val Thr Gly Cys Asp Asp Met Glu Lys Leu
        115                 120                 125

Trp Lys His Leu Phe Glu Arg Ala Val Pro Tyr Met Ala Lys Phe Val
130                 135                 140

Ile Phe Ala Lys Ile Asn Asp Pro Arg Glu Gly Arg Leu Arg Cys Tyr
145                 150                 155                 160

Cys Met Lys Thr Val Val Met Leu Gln Asn Val Val Pro Ala Lys
                165                 170                 175

Val Ser Leu Val Cys Val Val Lys Pro Asp Glu Phe Trp Ser Gly Val
            180                 185                 190

Lys Val Ser Val Tyr Ala Val Pro Asp Lys Met Asn Gln Ala Asp Tyr
        195                 200                 205

Ala Leu Asp Ala Ala Val Thr Leu Trp Asn Asn Gly Arg Asn His Leu
    210                 215                 220

Ile Phe Asn Leu Tyr Phe Gly Thr Trp Pro Asp Tyr Thr Glu Asp Val
225                 230                 235                 240

Gly Phe Asp Ile Arg Gln Pro Pro Gly Lys Ala Leu Glu Trp Leu Ala
                245                 250                 255

His Ile Tyr Trp Asp Asp Asp Lys Arg Tyr Ser Pro Ser Leu
            260                 265                 270

```
<210> SEQ ID NO 61
<211> LENGTH: 267
<212> TYPE: PRT
<213> ORGANISM: artificial sequence
<220> FEATURE:
<223> OTHER INFORMATION: fusion 2 of 10 neopeptides encoded by pTG19247

<400> SEQUENCE: 61

Gly Gln Ser Leu Pro Met Thr His Ser Leu Lys Leu Ser Lys Thr Asn
1               5                   10                  15

Arg Thr Leu Phe Leu Leu Gly Val Thr Lys Tyr Gly Leu Met Gly Ile
            20                  25                  30

Val Val Gly Thr Val Phe Ile Ile Arg Gly Leu Arg Ser Val Gly Ala
        35                  40                  45

Ser Arg His Gln Gly Leu Trp Tyr Val Arg Met Asn Arg Arg Arg Leu
    50                  55                  60

Lys Gly Glu Thr Gly Met Glu Asp Cys Val Met Ala Leu Glu Thr Leu
65                  70                  75                  80

Phe Thr Ala Ile Pro Leu Glu Ile Phe Ile Val Thr Met Glu Asn Asp
                85                  90                  95

Phe Pro Gly Gly Val Ile Gly Lys Ile His Ala Thr Gly Arg Gly Arg
            100                 105                 110

Ser Lys Leu Lys Ser Gly Ile Gly Ala Leu Val Leu Pro Gly Val Ser
        115                 120                 125

Thr Ala Asp Ile Ser Ser Asn His Gln Arg Glu Asn Ser Gly His Arg
    130                 135                 140

Arg Asp Gln Ile Thr Glu Lys Asp Ala Ala Leu Cys Val Leu Ile Asp
145                 150                 155                 160

Glu Met His Asn Tyr Met Tyr Trp Tyr Arg Gln Asp Pro Gly Met Val
                165                 170                 175

Leu Lys Leu Ile Tyr Tyr Ser Val Gly Ala Gly Ile Thr Gly Trp Met
            180                 185                 190

Tyr Gly Thr Val Gln Arg Thr Gly Arg Thr Arg Met Leu Pro Ala Asn
        195                 200                 205

Tyr Val Glu Ala Ile Glu Glu Trp Glu Cys Leu Asp Ser Ala Gln Gln
    210                 215                 220

Arg Leu His Arg Asp Val Met Leu Glu Asn Tyr Gly Asn Leu Phe Ser
225                 230                 235                 240

Leu Phe Thr Val Ser Pro Thr Leu Tyr Phe Leu His Ser Val Ser Leu
                245                 250                 255

Pro Ala Leu Asp Leu Lys Pro Gly Glu Gly Ala
            260                 265

<210> SEQ ID NO 62
<211> LENGTH: 270
<212> TYPE: PRT
<213> ORGANISM: artificial sequence
<220> FEATURE:
<223> OTHER INFORMATION: fusion 3 of 10 neopeptides encoded by pTG19247

<400> SEQUENCE: 62

Val Val Gly Trp Arg Ser Gly Val Glu Lys Asp Leu Asp Lys Val Leu
1               5                   10                  15

Gln Thr His Ser Val Phe Val Asn Val Ser Lys Lys Gly Ile Arg Thr
            20                  25                  30

Leu Leu Phe Ala Leu Met Met Ser Phe Pro Ala Leu Phe Asn Ile Gly
        35                  40                  45
```

```
Leu Leu Leu Phe Leu Val Glu Ala Thr Asn Ala Ser Val Phe Lys Tyr
        50                  55                  60

Tyr Ile His Gly Leu Ser Asp Leu Ile Asp Cys Cys Asp Leu Gly Tyr
65                  70                  75                  80

His Ser Ile Phe Tyr Leu Leu Lys Ile Ala Asn Phe Ser Asn Leu Ile
                85                  90                  95

Phe Leu His Leu Lys Arg Arg Val Lys Ser Val Ile Val His His Arg
                100                 105                 110

Ile Val Gly Cys Ser Leu Ala Val Ile Cys Gly Val Leu Tyr Gly Ser
                115                 120                 125

Thr Phe Val Pro Ile Ile Tyr Phe Leu Val Ile Ala Leu Lys Asn Ala
                130                 135                 140

Val Glu Ile Tyr Val Trp Ala Pro Lys Pro Tyr His Lys Phe Met Ala
145                 150                 155                 160

Phe Lys Pro Gly Leu Asp Arg Glu Gln Leu Tyr Trp Glu Leu Ser Lys
                165                 170                 175

Leu Thr His Ser Ile Thr Glu Leu Gly Pro Tyr Thr Leu Leu Leu Gln
                180                 185                 190

Ile Ser Asn Trp Phe Ile Asn Ala Arg Arg Cys Ile Leu Pro Asp Met
                195                 200                 205

Leu Gln Gln Arg Arg Asn Asp Pro Thr Ile Ser Leu Ser Gly Cys Ala
                210                 215                 220

Val Gln Met Phe Leu Ser Leu Ala Met Gly Thr Thr Glu Cys Val Leu
225                 230                 235                 240

Leu Gly Met Gln Ile Leu Ser Lys Leu Leu Asp Leu Ser Cys Glu
                245                 250                 255

Phe Ser Leu Leu Lys Ser Glu Cys His Arg Val Lys Met Gln
                260                 265                 270

<210> SEQ ID NO 63
<211> LENGTH: 267
<212> TYPE: PRT
<213> ORGANISM: artificial sequence
<220> FEATURE:
<223> OTHER INFORMATION: no TM fusion 2 with inversion of neopeptides 1
      and 2 and 7 and 8

<400> SEQUENCE: 63

Gly Leu Met Gly Ile Val Val Gly Thr Val Phe Ile Ile Arg Gly Leu
1               5                   10                  15

Arg Ser Val Gly Ala Ser Arg His Gln Gly Leu Gly Gln Ser Leu Pro
                20                  25                  30

Met Thr His Ser Leu Lys Leu Ser Lys Thr Asn Arg Thr Leu Phe Leu
                35                  40                  45

Leu Gly Val Thr Lys Tyr Trp Tyr Val Arg Met Asn Arg Arg Arg Leu
        50                  55                  60

Lys Gly Glu Thr Gly Met Glu Asp Cys Val Met Ala Leu Glu Thr Leu
65                  70                  75                  80

Phe Thr Ala Ile Pro Leu Glu Ile Phe Ile Val Thr Met Glu Asn Asp
                85                  90                  95

Phe Pro Gly Gly Val Ile Gly Lys Ile His Ala Thr Gly Arg Gly Arg
                100                 105                 110

Ser Lys Leu Lys Ser Gly Ile Gly Ala Leu Val Leu Pro Gly Val Ser
                115                 120                 125

Thr Ala Asp Ile Ser Ser Asn His Gln Arg Glu Asn Ser Gly His Arg
```

```
                130             135             140
Arg Asp Gln Ile Thr Glu Lys Asp Ala Ala Leu Cys Val Leu Ile Asp
145                 150                 155                 160

Glu Met Gly Trp Met Tyr Gly Thr Val Gln Arg Thr Gly Arg Thr Arg
                165                 170                 175

Met Leu Pro Ala Asn Tyr Val Glu Ala Ile His Asn Tyr Met Tyr Trp
            180                 185                 190

Tyr Arg Gln Asp Pro Gly Met Val Leu Lys Leu Ile Tyr Tyr Ser Val
        195                 200                 205

Gly Ala Gly Ile Thr Glu Glu Trp Glu Cys Leu Asp Ser Ala Gln Gln
    210                 215                 220

Arg Leu His Arg Asp Val Met Leu Glu Asn Tyr Gly Asn Leu Phe Ser
225                 230                 235                 240

Leu Phe Thr Val Ser Pro Thr Leu Tyr Phe Leu His Ser Val Ser Leu
                245                 250                 255

Pro Ala Leu Asp Leu Lys Pro Gly Glu Gly Ala
            260                 265

<210> SEQ ID NO 64
<211> LENGTH: 189
<212> TYPE: PRT
<213> ORGANISM: artificial sequence
<220> FEATURE:
<223> OTHER INFORMATION: no TM fusion 3 by suppression of neopeptides 2,
      4 and 5

<400> SEQUENCE: 64

Val Val Gly Trp Arg Ser Gly Val Glu Lys Asp Leu Asp Lys Val Leu
1               5                   10                  15

Gln Thr His Ser Val Phe Val Asn Val Ser Lys Glu Ala Thr Asn Ala
            20                  25                  30

Ser Val Phe Lys Tyr Tyr Ile His Gly Leu Ser Asp Leu Ile Asp Cys
        35                  40                  45

Cys Asp Leu Gly Tyr His Phe Leu Val Ile Ala Leu Lys Asn Ala Val
    50                  55                  60

Glu Ile Tyr Val Trp Ala Pro Lys Pro Tyr His Lys Phe Met Ala Phe
65                  70                  75                  80

Lys Pro Gly Leu Asp Arg Glu Gln Leu Tyr Trp Glu Leu Ser Lys Leu
                85                  90                  95

Thr His Ser Ile Thr Glu Leu Gly Pro Tyr Thr Leu Leu Gln Ile
            100                 105                 110

Ser Asn Trp Phe Ile Asn Ala Arg Arg Cys Ile Leu Pro Asp Met Leu
        115                 120                 125

Gln Gln Arg Arg Asn Asp Pro Thr Ile Ser Leu Ser Gly Cys Ala Val
    130                 135                 140

Gln Met Phe Leu Ser Leu Ala Met Gly Thr Thr Glu Cys Val Leu Leu
145                 150                 155                 160

Gly Met Gln Ile Leu Ser Lys Leu Leu Asp Leu Ser Cys Glu Phe
                165                 170                 175

Ser Leu Leu Lys Ser Glu Cys His Arg Val Lys Met Gln
            180                 185

<210> SEQ ID NO 65
<211> LENGTH: 270
<212> TYPE: PRT
<213> ORGANISM: artificial sequence
<220> FEATURE:
```

<223> OTHER INFORMATION: fusion 3 encoded by pTG19290

<400> SEQUENCE: 65

Ser Ser Thr Ile Met Asp Val Asp Ser Thr Ile Ser Ser Trp Arg Ser
1               5                   10                  15

Thr Pro Ala Met Met Asn Gly Gln Gly Ser Thr Lys Ser Lys Lys Val
            20                  25                  30

Ser Asp Ile Lys Glu Glu Val Leu Ser Ala Ala Cys His Pro Val Gln
        35                  40                  45

His Ser Lys Val Glu Tyr Tyr His Ile Glu Val Met Lys Lys Lys Met
    50                  55                  60

Tyr Ile Phe Trp Gly Lys Met Ser Arg Arg Thr Leu Leu Pro Ile Pro
65                  70                  75                  80

Thr Ser Trp Tyr Leu Glu Asn Ile Tyr Pro Asp Ser Gln Ile Thr Arg
                85                  90                  95

Arg Tyr Tyr Ser Leu Gly Glu Ile Arg Asn Val Glu Ser Pro Phe Asn
            100                 105                 110

Val Val Ala Trp His Gly Asn Tyr Thr Leu Tyr Lys Tyr Asn Leu Lys
        115                 120                 125

Asn Phe Met Val Ile Asn Ser Asp Tyr Glu Leu Ala Glu Val His Lys
    130                 135                 140

Ala Leu Leu Asp Asn Lys Asn Lys Val Leu Glu Val Lys Lys Pro Pro
145                 150                 155                 160

Arg Phe Glu Lys Gly Pro Leu Pro Gly Glu Asp Trp Thr Ile Phe Lys
                165                 170                 175

Tyr Asn His Ser Thr Tyr Gln Pro Val Leu Leu Thr Glu Asp Arg Trp
            180                 185                 190

Val Arg Asn Gln Ala Asn Leu Asp Lys Glu His Val Pro Leu Leu Lys
        195                 200                 205

Ile Glu Glu Pro Pro Ser Thr Ala Leu Asp Thr Glu Glu Glu Glu Asp
    210                 215                 220

Asp Thr Ile His Met Trp Asn Ala Ile Met Thr Phe Tyr Ser Ala Leu
225                 230                 235                 240

Ile Asp Leu Ser Thr Val Glu Lys His Cys Gly Lys Val Pro Tyr Pro
                245                 250                 255

Leu Ser Tyr Val Pro Ala Val Leu Ser Glu Leu Thr Asp Gln
            260                 265                 270

<210> SEQ ID NO 66
<211> LENGTH: 5
<212> TYPE: PRT
<213> ORGANISM: artificial sequence
<220> FEATURE:
<223> OTHER INFORMATION: linker 5aa

<400> SEQUENCE: 66

Gly Ser Gly Ser Gly
1               5

<210> SEQ ID NO 67
<211> LENGTH: 5
<212> TYPE: PRT
<213> ORGANISM: artificial sequence
<220> FEATURE:
<223> OTHER INFORMATION: linker of 5aa

<400> SEQUENCE: 67

Ser Gly Ser Gly Ser

```
<210> SEQ ID NO 68
<211> LENGTH: 10
<212> TYPE: PRT
<213> ORGANISM: artificial sequence
<220> FEATURE:
<223> OTHER INFORMATION: linker of 10aa

<400> SEQUENCE: 68

Gly Ser Gly Ser Gly Ser Gly Ser Gly Ser
1               5                   10

<210> SEQ ID NO 69
<211> LENGTH: 5
<212> TYPE: PRT
<213> ORGANISM: artificial sequence
<220> FEATURE:
<223> OTHER INFORMATION: linker of 5aa

<400> SEQUENCE: 69

Gly Ser Thr Ser Gly
1               5

<210> SEQ ID NO 70
<211> LENGTH: 5
<212> TYPE: PRT
<213> ORGANISM: artificial sequence
<220> FEATURE:
<223> OTHER INFORMATION: linker of 5 aa

<400> SEQUENCE: 70

Ser Gly Thr Gly Ser
1               5
```